United States Patent [19]

Greenfield et al.

[11] Patent Number: 5,122,368

[45] Date of Patent: Jun. 16, 1992

[54] ANTHRACYCLINE CONJUGATES HAVING A NOVEL LINKER AND METHODS FOR THEIR PRODUCTION

[75] Inventors: Robert S. Greenfield, Wallingford; Gary R. Braslawsky, Glastonbury, both of Conn.; Lee J. Olech, Richmond, Calif.; Takushi Kaneko, Guilford; Peter A, Kiener, Killingworth, both of Conn.

[73] Assignee: Bristol-Myers Squibb Company, New York, N.Y.

[21] Appl. No.: 353,729

[22] Filed: May 17, 1989

Related U.S. Application Data

[63] Continuation-in-part of Ser. No. 270,509, Nov. 16, 1988, abandoned, which is a continuation-in-part of Ser. No. 155,181, Feb. 11, 1988, abandoned.

[51] Int. Cl.$^5$ .............. A61K 37/26; A61K 37/43; A61K 37/66; A61K 39/44; C07K 7/08; C07K 7/30; C07K 7/40; C07K 17/06

[52] U.S. Cl. .................. 530/327; 424/85.2; 424/85.4; 424/85.5; 424/85.6; 424/85.7; 424/85.91; 514/2; 514/3; 514/4; 514/8; 514/14; 514/21; 514/23; 514/34; 530/303; 530/328; 530/351; 530/394; 530/399; 530/402; 530/404; 530/405; 530/408; 530/409; 530/391.9; 536/1.1; 536/6.4

[58] Field of Search .............. 424/85.91, 85.1, 14 85.7; 530/390, 391, 394, 399, 402, 327, 328, 404, 405, 408, 409, 351, 303; 536/1.1, 6.4; 514/8, 14, 21, 23, 34, 2, 3, 4

[56] References Cited

U.S. PATENT DOCUMENTS

| | | | |
|---|---|---|---|
| 4,112,217 | 9/1978 | Henry et al. | 536/6.4 |
| 4,263,428 | 4/1981 | Apple et al. | 536/6.4 |
| 4,284,625 | 8/1981 | Jolles | 536/6.4 |
| 4,522,750 | 6/1985 | Ades et al. | 530/397 |
| 4,542,225 | 9/1985 | Blattler et al. | 548/473 |
| 4,545,985 | 10/1985 | Pastan et al. | 424/85.91 |
| 4,560,512 | 12/1985 | Firestone | 536/6.4 |
| 4,590,001 | 5/1986 | Stjernholm | 530/394 |
| 4,618,492 | 10/1986 | Blattler et al. | 424/85.91 |
| 4,671,958 | 6/1987 | Rodwell et al. | 424/85.91 |
| 4,675,382 | 6/1987 | Murphy | 530/350 |
| 4,699,784 | 10/1987 | Shih et al. | 424/85.91 |

FOREIGN PATENT DOCUMENTS

| | | |
|---|---|---|
| 0004467 | 10/1979 | European Pat. Off. . |
| 0294294 | 12/1988 | European Pat. Off. . |
| 0306943 | 3/1989 | European Pat. Off. . |
| 0318948 | 6/1989 | European Pat. Off. . |
| 0155334 | 7/1986 | Japan . |
| 0057569 | 3/1988 | Japan . |
| WO8705031 | 8/1987 | PCT Int'l Appl. . |
| WO8800837 | 2/1988 | PCT Int'l Appl. . |
| WO8809823 | 12/1988 | PCT Int'l Appl. . |
| 2116979A | 10/1983 | United Kingdom . |

Primary Examiner—Christine Nucker
Assistant Examiner—Kay K. Kim
Attorney, Agent, or Firm—Deborah Barnett; Mollie M. Yang

[57] ABSTRACT

The invention relates to anthracycline conjugates comprising at least one anthracycline molecule linked to a molecule that is reactive with a cell population to be eliminated such as antibody, bombesin, EGF and transferrin. Each anthracycline molecule, having a keto group at the C-13 position, is conjugated to the antibody via a linker arm and is bound to that linker arm via an acid-sensitive acylhydrazone bond at the 13-keto position of the anthracycline. The linker additionally contains a disulfide or thioether linkage as part of the antibody or ligand attachment to the immunoconjugate. The novel anthracycline acylhydrazone derivatives are useful in the preparation of the conjugates of this invention. The acid-sensitive hydrazone bond of the conjugates of this invention allows the release of free anthracycline from the conjugates in the acidic external or internal environment of the target cell. The conjugates and methods of the invention are therefore useful in antibody- or ligand-mediated drug delivery systems for the preferential killing of a selected cell population in the treatment of diseases such as cancers and other tumors, non-cytocidal viral or other pathogenic infections, and autoimmune disorders.

12 Claims, 35 Drawing Sheets

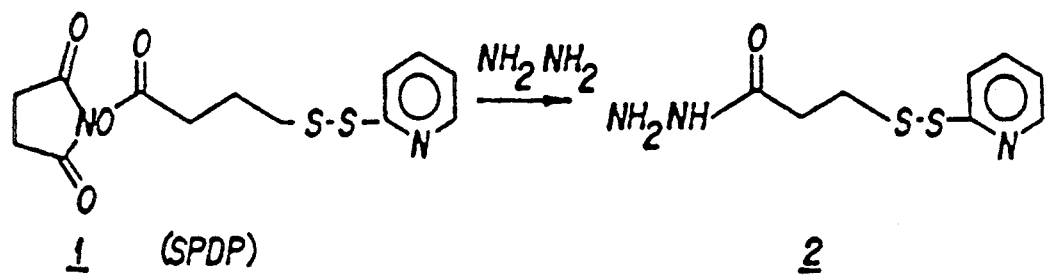
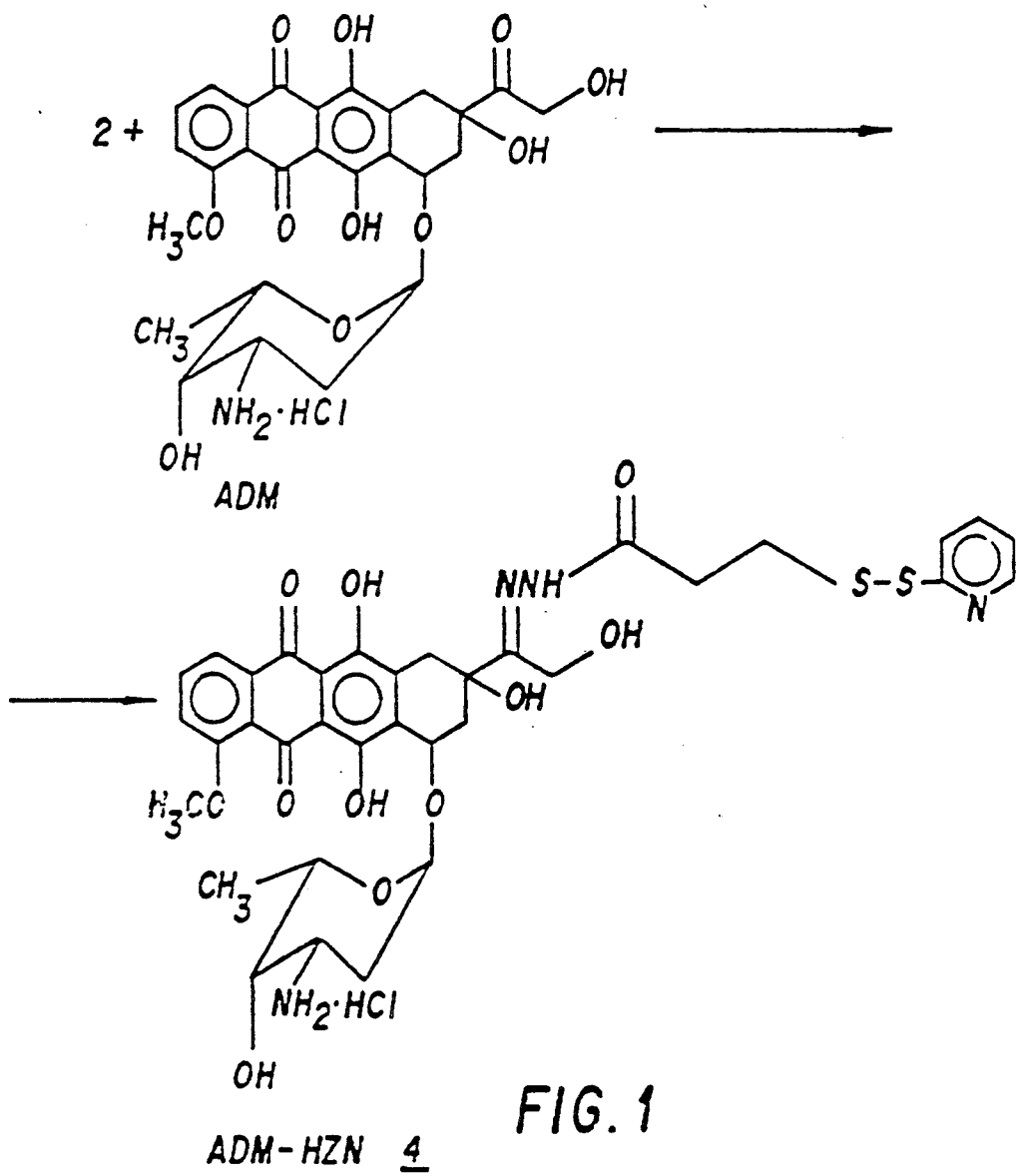
FIG.1

□ 5E9 IMMUNOCONJUGATES } ANTIBODIES THIOLATED WITH 2-IT
● 3A1 IMMUNOCONJUGATES

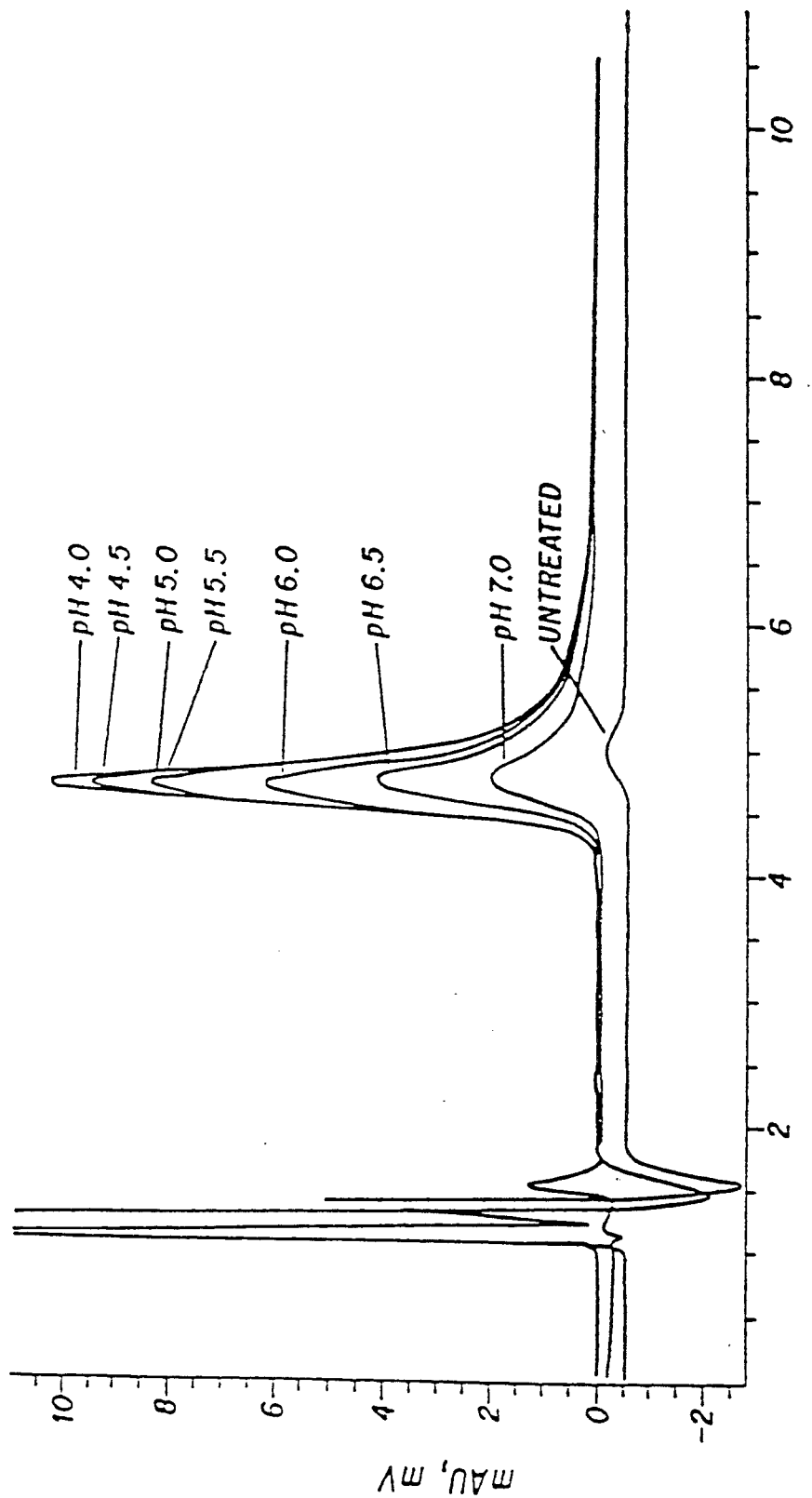

ANTI-TUMOR ACTIVITY OF ADM-HCl ON RAMOS TUMOR XENOGRAFTS

| SCHEDULE[a] | DOSE (mg/kg)[a] per inj | DOSE (mg/kg)[a] cum | TUMOR INHIBITION[b] T-C | TUMOR INHIBITION[b] CR | TUMOR INHIBITION[b] CURES | TDD | TOXICITY[c] D/T | TOXICITY[c] (%) |
|---|---|---|---|---|---|---|---|---|
| IV ROUTE | | | | | | | | |
| Q1Dx1 | 20 | 20 | — | — | — | — | 7/9 | (78) |
|  | 20 | 20 | 7.0 | 0 | 0 | 0.5 | 2/7 | (29) |
|  | 18 | 18 | — | — | — | — | 4/6 | (67) |
|  | 18 | 18 | — | — | — | — | 6/9 | (66) |
|  | 18 | 18 | 7.5 | 0 | 0 | 0.6 | 4/9 | (44) |
|  | 18 | 18 | 8.0 | 1 | 0 | 0.6 | 0/8 | (0) |
|  | 16 | 16 | 0 | 0 | 0 | 0 | 1/8 | (12) |
|  | 16 | 16 | 5.5 | 0 | 0 | 0.4 | 1/9 | (11) |
|  | 16 | 16 |  |  |  |  | 1/6 | (16) |
| Q2Dx2 | 18 | 36 | — | — | — | — | 7/7 | (100) |
|  | 15 | 30 | — | — | — | — | 7/7 | (100) |
|  | 12 | 24 | — | — | — | — | 5/7 | (71) |
|  | 12 | 24 | — | — | — | — | 5/5 | (100) |
|  | 10 | 20 | — | — | — | — | 3/5 | (60) |
|  | 8 | 16 | 1.5 | 0 | 0 | 0 | 1/5 | (20) |
| Q3Dx2 | 16 | 32 | — | — | — | — | 8/8 | (100) |
|  | 14 | 28 | — | — | — | — | 7/8 | (88) |
|  | 12 | 24 | — | — | — | — | 6/8 | (75) |
| Q4Dx2 | 14 | 28 | — | — | — | — | 6/7 | (86) |
|  | 12 | 24 | 10.5 | — | — | 1.0 | 3/7 | (43) |
| Q4Dx3 | 10 | 30 | 0 | 0 | 0 | 0 | 0/8 |  |
| Q7Dx3 | 11 | 33 | 1 | 0 | 0 | 0 |  |  |
|  | 10 | 30 | 0 | 0 | 0 | 0 |  |  |
|  | 10 | 30 | 0 | 0 | 0 | 0 |  |  |

\* See Table 2 for Legend

FIG. 24

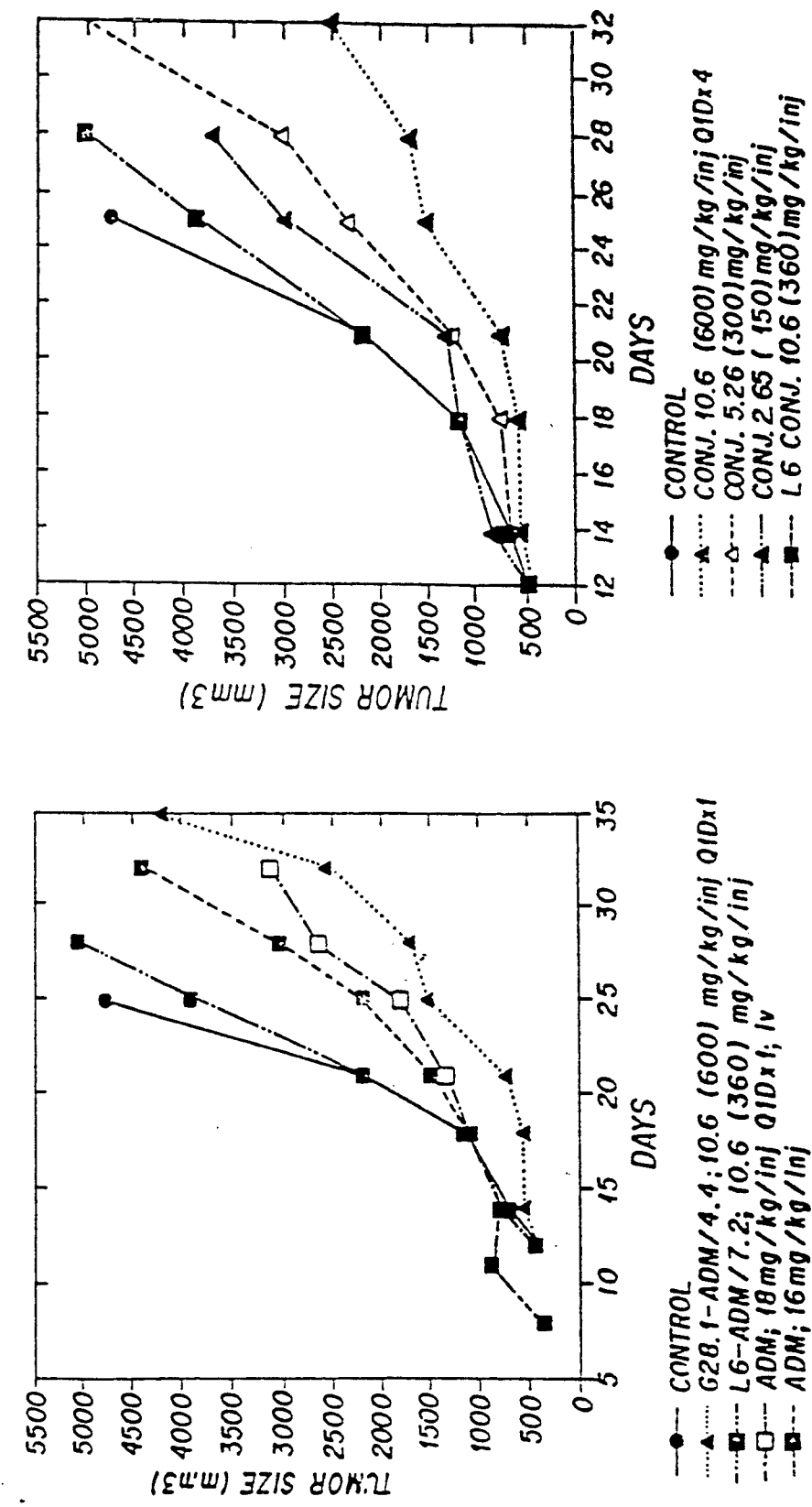

REVERSE PHASE C18

ION EXCHANGE CX-300

HPLC ANALYSIS OF EGF-ADM CONJUGATE

ANTHRACYCLINE CONJUGATES HAVING A NOVEL LINKER AND METHODS FOR THEIR PRODUCTION

This application is a continuation-in-part of copending U.S. patent application, Ser. No. 270,509, filed on Nov. 16, 1988, now abandoned, which is a continuation-in-part of copending U.S. patent application, Ser. No. 155,181, filed on Feb. 11, 1988 in the United States Patent and Trademark Office, now abandoned, which applications are incorporated by reference herein in their entirety.

TECHNICAL FIELD Of THE INVENTION

The present invention relates to novel anthracycline conjugates and methods for their production. More particularly, the invention relates to conjugates comprising at least one anthracycline molecule linked to a second molecule that is reactive with a selected cell population to be eliminated, the anthracycline being linked to the cell-reactive molecule via a 13-keto acylhydrazone bond.

Thus, according to one embodiment of the present invention, the conjugate is comprised of an antibody reactive with a selected cell population to be eliminated, the antibody having a number of cytotoxic anthracycline molecules covalently linked to its structure. Each anthracycline molecule is conjugated to the antibody via a linker arm, the anthracycline being bound to that linker via an acid-sensitive acylhydrazone bond at the 13-keto position of the anthracycline. A preferred embodiment of the invention relates to an adriamycin immunoconjugate wherein adriamycin is attached to the linker arm through an acylhydrazone bond at the 13-keto position. The linker additionally contains a disulfide or thioether linkage as part of the antibody attachment to the immunoconjugate.

According to another embodiment of the invention, the anthracycline molecule is conjugated via a linker arm to a ligand such as epidermal growth factor (EGF) or bombesin, the anthracycline being bound to the linker via an acid-sensitive acylhydrazone bond at the 13-keto position of the anthracycline. The linker may additionally contain a disulfide or thioether bond within its structure. In addition, according to this invention, new acylhydrazone derivatives of anthracyclines are synthesized and used in the preparation of the conjugates of this invention.

The acid-sensitive acylhydrazone bond of the conjugates of this invention allows for the release of anthracycline from the conjugate in the acidic external or internal environment of the target cell. The conjugates and methods of the invention are therefore useful in antibody or ligand-mediated drug delivery systems for the preferential killing of a selected population of cells in the treatment of diseases such as cancers and other tumors, non-cytocidal viral or other pathogenic infections, and autoimmune disorders.

BACKGROUND OF THE INVENTION

Anthracyclines are antibiotic compounds that exhibit cytotoxic activity. Studies have indicated that anthracyclines may operate to kill cells by a number of different mechanisms including: 1) intercalation of the drug molecules into the DNA of a cell thereby inhibiting DNA-dependent nucleic acid synthesis; 2) production by the drug of free radicals which then react with cellular macromolecules to cause damage to the cells or 3) interactions of the drug molecules with the cell membrane [see, e.g., C. Peterson et al., "Transport And Storage Of Anthracyclines In Experimental Systems And Human Leukemia", in *Anthracycline Antibiotics In Cancer Therapy*, F. M. Muggia et al. (ed.s), p. 132 (Martinus Nijhoff Publishers 1982); see also, N. R. Bachur, "Free Radical Damage", id. at pp. 97–102]. Because of their cytotoxic potential, anthracyclines have been used in the treatment of numerous cancers such as leukemia, breast carcinoma, lung carcinoma, ovarian adenocarcinoma, and sarcomas [see, e.g., P. H. Wiernik, "Current Status Of Adriamycin And Daunomycin In Cancer Treatment", in *Anthracyclines: Current Status And New Developments*. S. T. Crooke et al. (eds.), pp. 273–94 (Academic Press 1980)]. Commonly used anthracyclines include adriamycin and daunomycin.

Although these compounds may be useful in the treatment of neoplasms and other disease states wherein a selected cell population is sought to be eliminated, their therapeutic efficacy is often limited by the dose-dependent toxicity associated with their administration. For example, in the treatment of tumors, typical adverse side effects include myelosuppression and cardiotoxicity [see S. T. Crooke, "Goals For Anthracycline Analog Development At Bristol Laboratories", *Anthracyclines: Current Status And New Developments*, supra, at p. 11]. Attempts have therefore been made in the treatment of tumors to improve the therapeutic effects of these compounds by linking the anthracycline to antibodies directed against tumor-associated antigens. In this way, the drug can be delivered or "targeted" to the tumor site and its toxic side effects on normal cells in the body may be diminished. Immunoconjugates comprised of the anthracyclines, adriamycin (ADM) or daunomycin (DAU), linked to polyclonal or monoclonal antibodies to tumor-associated antigens are known in the art [see, e.g., J. Gallego et al., "Preparation Of Four Daunomycin-Monoclonal Antibody 791T/36 Conjugates With Anti-Tumour Activity", *Int. J. Cancer* 33, pp. 737–44 (1984) and R. Arnon et al., "In Vitro And In Vivo Efficacy Of Conjugates Of Daunomycin With Anti-Tumor Antibodies", *Immunological Rev.*, 62, pp. 5–27 (1982)].

The most frequently used approaches for the attachment of an anthracycline to an antibody have utilized a linkage at the amino sugar moiety of the anthracycline. For example, the amino sugar has been oxidized by sodium periodate treatment and directly attached to lysine residues on the antibody via Schiff base formation [see, e.g., E. Hurwitz et al., "The Covalent Binding Of Daunomycin And Adriamycin To Antibodies, With Retention Of Both Drug And Antibody Activities", *Cancer Res.*, 35, pp. 1182–86 (1975)]. Alternatively, anthracyclines have been linked to antibodies through carbodiimide-mediated linkage of the amino sugar of the anthracycline to carboxyl groups on the antibody [see, e.g., E. Hurwitz et al., supra]. And, anthracyclines have also been linked to antibodies by cross-linking the amino sugar of the drug and amino groups on the antibody with glutaraldehyde [see, e.g., M. Belles-Isles et al., "In Vitro Activity Of Daunomycin-Anti-AlphaFetoprotein Conjugate On Mouse Hepatoma Cells", *Br. J. Cancer*, 41, pp 841–42 (1980)]. However, studies with immunoconjugates in which the amino sugar portion of the anthracycline molecule was modified by linkage to the antibody indicate a loss of cytotoxic activity of the conjugated drug [see, e.g., R.

Arnon et al., supra, at pp. 7–8. In addition, studies of anthracycline analogs indicate that modifications of anthracyclines at their amino sugars result in a decrease in the cytotoxic activity of the drug analog relative to the parent drug [see, e.g., K. Yamamoto et al., "Antitumor Activity Of Some Derivatives Of Daunomycin At The Amino And Methyl Ketone Functions", *J. Med. Chem.*, 15, pp. 872–75 (1972)].

Still other immunoconjugates have been prepared wherein the anthracycline, daunomycin, has been linked directly to an antibody at the 14-carbon (C-14) position of the drug. However, the selective cytotoxic activity of these immunoconjugates toward tumor cells was not easily reproducible and was revealed consistently only at a concentration of 20 µg/ml [see J. Gallego et al., supra].

Japanese patent application 274658 discloses the conjugation of an anthracycline to an antibody via a 13-keto acylhydrazone linkage. This conjugation was accomplished using methods that involve derivatization of the antibody and subsequent reaction of that derivative with anthracycline. These methods are disfavored because derivatization of the antibody involves undesirable non-specific reactions and very low anthracycline:antibody ratios are obtained.

According to the first method, the antibody was treated with carbodiimide in the presence of hydrazine to yield a hydrazido antibody derivative which was then reacted with the anthracycline such that the anthracycline was linked directly to the antibody structure. The resulting immunoconjugates, however, are prone to aggregation of the antibody molecules. Furthermore, because this method requires carboxylic acid groups on the antibody molecule which are limited in number, these immunoconjugates have low anthracycline:antibody ratios (approximately 1.1–1.3).

The second method involves reacting the antibody with succinic anhydride to yield an amide acid derivative of the antibody. This derivative was next reacted with hydrazine to yield an antibody hydrazid derivative which was then reacted with the anthracycline, daunomycin. This second approach is flawed in that the reaction of the antibody derivative with hydrazine is non-specific, leading to the production of a mixture of different antibody derivatives in addition to the desired hydrazid derivative. Thus, as indicated in the 274658 application, the molar ratio of anthracycline to antibody was very low (approximately 1, see Japanese application, page 264, column 1). See also, European patent application, Publication No. 294294, which discloses the conjugation of a C-13 hydrazone derivative of an anthracycline to the carbohydrate moiety of an antibody.

Finally, other anthracycline hydrazones are disclosed in G. L. Tong et al., *J. Med. Chem.*, 21, pp. 732–37 (1978); T. Smith et al., *J. Med. Chem.*, 21, pp. 280–33 (1978); and R. T. C. Brownlee et al., *J. Chem. Soc.*, pp. 659–61 (1986). See also U.S. Pat. No. 4,112,217, which discloses bis-hydrazones of daunomycin and adriamycin.

In other studies, anthracyclines have been linked to high molecular weight carriers, such as dextran or polyglutamic acid, in order to potentiate the cytotoxic activity and reduce the toxicity of the drug [see, e.g., R. Arnon et al., supra, at p. 5 and E. Hurwitz et al., "Soluble Macromolecules As Carriers For Daunorubicin", *J. Appl. Biochem.*, 2, pp. 25–35 (1980)]. These carrier-linked anthracyclines have also been covalently bound to antibodies directed against tumor-associated antigens to form immunoconjugates for targeting of the cytotoxic drug specifically to tumor cells For example, adriamycin has been linked to such an "anti-tumor" antibody via a carboxymethyl-dextran hydrazide bridge wherein the adriamycin molecule was linked to a hydrazine derivative of carboxymethyl dextran at the C-13 carbonyl side chain of the tetracycline ring of the adriamycin to form a hydrazone. The antibody was then linked to the dextran hydrazide derivative with glutaraldehyde to form an adriamycin-dexantibody conjugate [see R. Arnon et al., "Monoclonal Antibodies As Carriers For Immunotargeting Of Drugs", in *Monoclonal Antibodies For Cancer Detection And Therapy*, R. W. Baldwin et al. (eds.), pp. 365–83 (1985) and E. Hurwitz et al., "A Conjugate Of Adriamycin And Monoclonal Antibodies To Thy-1 Antigen Inhibits Human Neuroblastoma Cells In Vitro", *Ann. N.Y. Acad. Sci.*, 417, pp. 125–36 (1983)].

However, the use of carriers entails certain disadvantages. For example, carrier-containing immunoconjugates are quite large in size and are removed rapidly by the reticuloendothelial system in vivo [see, e.g , R. O. Dillman et al., "Preclinical Trials With Combinations And Conjugates Of T101 Monoclonal Antibody And Doxorubicin", *Cancer Res.*, 46, pp. 4886–91 (1986)]. This rapid removal of the carrier-containing immunoconjugates may not be advantageous for therapy because the conjugated drug may never reach its intended site of action, i.e., the selected group of cells to be killed. In addition, the presence of the high molecular weight carrier may negatively affect the stability of the immunoconjugate and has been shown to reduce the binding activity of the antibody of the conjugate [see, e.g., M. J. Embleton et al., "Antibody Targeting Of Anti-Cancer Agents", in *Monoclonal Antibodies For Cancer Detection And Therapy*. R. W. Baldwin et al. (eds.), pp. 323–24 (1985)]. Furthermore, in studies with tumor cells, there is no evidence that high molecular weight carrier-containing immunoconjugates are able to localize to the tumor cells in vivo. Compare C. H. J. Ford et al., "Localization And Toxicity Study Of A Vindesine-Anti-CEA Conjugate In Patients With Advanced Cancer", *Br. J. Cancer*, 47, 35–42 (1983), which demonstrates localization of directly-conjugated drug-antibody conjugates to tumor cells in vivo.

Thus, the conjugation of anthracyclines to antibodies by the use of specific linkages and carriers has been disclosed. As outlined above, the use of these immunoconjugates entails distinct disadvantages depending upon the specific linkage or carrier used.

Certain ligand-toxin conjugates have also been disclosed. For example, U.S. Pat. No. 4,545,985, issued to I. Pastan, discloses an exotoxin conjugate wherein Pseudomonas exotoxin (PE) is linked to EGF in a ratio of 1:2 for use against cells having large numbers of EGF receptors. EGF-ricin A and EGF-diphtheria toxin conjugates have also been made [see, e.g., D. B. Cawley et al., "Epidermal Growth Factor-Toxin A Chain Conjugates: EGF-Ricin A Is A Potent Toxin While EGF-Diphtheria Fragment A Is Nontoxic", *Cell*, 22, pp. 563–70 (1980) and N. Shimizu et al., "A Cytotoxic Epidermal Growth Factor Cross-Linked To Diphtheria Toxin A-Fragment", *FEBS Letters*, 118 (No. 2), pp. 274–78 (1980)]. Furthermore, Pseudomonas exotoxin fusion proteins have been prepared using proteins, polypeptides and growth factors such as TGF-α, IL-2, IL-6 and CD4 [see, e.g., I. Pastan et al., "Novel Cytotoxic Agents Created By The fusion Of Growth Factor And Toxin Genes", *Fourth Internatl. Conference On Monoclonal Antibody Immunoconjugates For Cancer*, p.36 (Mar. 30-Apr. 1, 1989); H. Lorberboum et al., *Proc. Natl. Acad. Sci. USA*, 85, pp. 1922–26 (1988); V. K. Chaudhary et al., *Proc. Natl. Acad. Sci. USA*, 84, pp. 4538–42 (1987); C. B. Siegall et al., *Proc. Natl. Acad. Sci. USA*, 85, pp. 9738–42 (1988); and V. K. Chaudhary et al., *Nature*, 335, pp. 369–72 (1988)]. And a diphtheria toxin-α-melanocyte-stimulating hormone fusion protein has been made [see J. R. Murphy et al., "Genetic Construction, Expression And Melanoma-Selective Cytotoxicity Of A Diphtheria Toxin-Related α-Melanocyte-Stimulating Hormone Fusion Protein", *Proc. Natl. Acad. Sci. USA*, 83, pp 8258–62 (1986) and U.S. Pat. No. 4,675,382, issued to J. R. Murphy]. Ligand conjugates comprising protein toxins, however, may prove to be immunogenic in xenogeneic hosts.

In addition, anthracyclines such as ADM or DAU have been chemically linked to certain protein or polypeptide ligands such as transferrin [see United Kingdom patent application, GB 2116979 A] and melanotropin [see J. M. Varga et al., "Melanotropin-Daunomycin Conjugate Shows Receptor-Mediated Cytotoxicity For Cultured Murine Melanoma Cells", *Nature*, 267, pp. 56–58 (1977)]. See, also, PCT patent application WO 88/00837 (EGF linked via a polymeric carrier to a cytotoxic substance such as dauromycin) and U.S. Pat. Nos. 4,522,750 and 4,590,001 (transferrin linked to vinca alkaloid and platinum, respectively).

SUMMARY OF THE INVENTION

The present invention provides a novel chemistry for linking cytotoxic anthracycline molecules via a linker arm to a molecule capable of reacting with a selected target cell population to be killed. This cell-reactive molecule can be a protein such as an antibody or a ligand such as bombesin or EGF.

According to one embodiment of this invention, a number of anthracycline molecules are linked to an antibody reactive with a selected target cell population. Each anthracycline is linked to the antibody via a linker arm, the anthracycline being bound to that linker through an acylhydrazone bond at the 13-keto position of the anthracycline, to form the novel immunoconjugates of the invention. For example, a preferred embodiment of the invention involves the synthesis of a novel adriamycin hydrazone derivative (ADM-HZN) that was then condensed with a thiolated antibody, resulting in the attachment of the anthracycline to the antibody via a linker arm. An acylhydrazone bond formed at the C-13 position of the ADM serves as the site of attachment of the ADM to the linker. Additionally, a disulfide bond is present within the linker as the site of attachment of the antibody. According to another preferred embodiment, the ADM-HZN was reduced to generate a sulfhydryl group and the resulting novel hydrazone derivative was condensed with a maleimide-derivatized antibody. This led to the formation of a linker arm having an acylhydrazone bond as the site of the linker attachment to the C-13 position of ADM and a thioether bond within the linker as part of the linker attachment to the antibody.

According to yet another preferred embodiment of the invention, the novel ADM-HZN intermediate was covalently linked to thiolated ligands, such as bombesin, transferrin or EGF, resulting in the attachment of the anthracycline to the ligand via a linker arm. As in the other embodiments described above, the anthracyline is attached to the linker via an acylhydrazone bond formed at the C-13 position of the anthracycline. Additionally, a disulfide or thioether bond may be present within the linker structure. As is evident from these embodiments, the present invention provides novel acylhydrazone derivatives of anthracyclines useful in the preparation of the conjugates of this invention.

The immunoconjugates of the present invention have anthracycline:antibody molar ratios of approximately 4–10 and retain both antibody and cytotoxic drug activity for the killing of selected target cells. The anthracycline-ligand conjugates described herein may have an anthracycline:ligand ratio of at least 1, and retain both receptor binding activity and cytotoxic drug activity. The acid-sensitive hydrazone bond that is present at the site of attachment of the anthracycline to the linker arm of these conjugates, and additionally the disulfide or thioether linkages within the linker arm of the preferred embodiments of this invention, are ideally suited for the release of active drug under reducing and acidic conditions such as those typically encountered within a cell, e.g., in lysosomal vesicles.

The conjugates of this invention may be used in pharmaceutical compositions, such as those comprising a pharmaceutically effective amount of at least one conjugate of the invention and a pharmaceutically acceptable carrier. The present invention also encompasses methods for the selective delivery of cytotoxic drugs to a selected population of target cells desired to be eliminated, as well as methods for treating a mammal in a pharmaceutically acceptable manner with a pharmaceutically effective amount of the compositions of the invention.

Advantageously, the conjugates, pharmaceutical compositions, and methods disclosed herein provide a useful approach to the targeting of cytotoxic anthracycline drugs to a selected population of cells for the preferential killing of those target cells in the treatment of diseases such as cancers and other tumors, non-cytocidal viral or other pathogenic infections, and autoimmune disorders.

BRIEF DESCRIPTION OF THE DRAWINGS

FIG. 1 depicts in schematic form the synthesis of the novel ADM-HZN hydrazone derivative used in the preparation of the immunoconjugates of this invention.

FIG. 9 is an HPLC chromatograph depicting the stability of an immunoconjugate of this invention over the pH range of 4-7. This chromatograph demonstrates the acid-sensitivity of the acylhydrazone bond of the invention as indicated by the increased release of free ADM from the immunoconjugate as the pH became more acidic

FIG. 24 depicts in table form the in vivo anti-tumor activity of ADM on human Ramos tumor xenografts in mice using i.v. administration but varying the treatment schedules and dosages.

FIG. 26A depicts in graph form the in vivo anti-tumor activity of an immunoconjugate of this invention on human Ramos tumor xenografts in mice compared to the anti-tumor activity of optimized free ADM (given i.v. on a Q1Dx1 treatment schedule at 16-18 mg/kg/inj). The immunoconjugate showed a greater anti-tumor activity than the free ADM. FIG. 26B depicts the in vivo anti-tumor activity of the immunoconjugate over time at different dosages of the conjugate, demonstrating the dosage-dependent nature of the conjugate's anti-tumor effect. The dosages of the immunoconjugates tested in FIGS. 26A and B are given as the input of conjugated anthracycline, with the antibody input given in parenthesis.

DETAILED DESCRIPTION OF THE INVENTION

Figure 2:
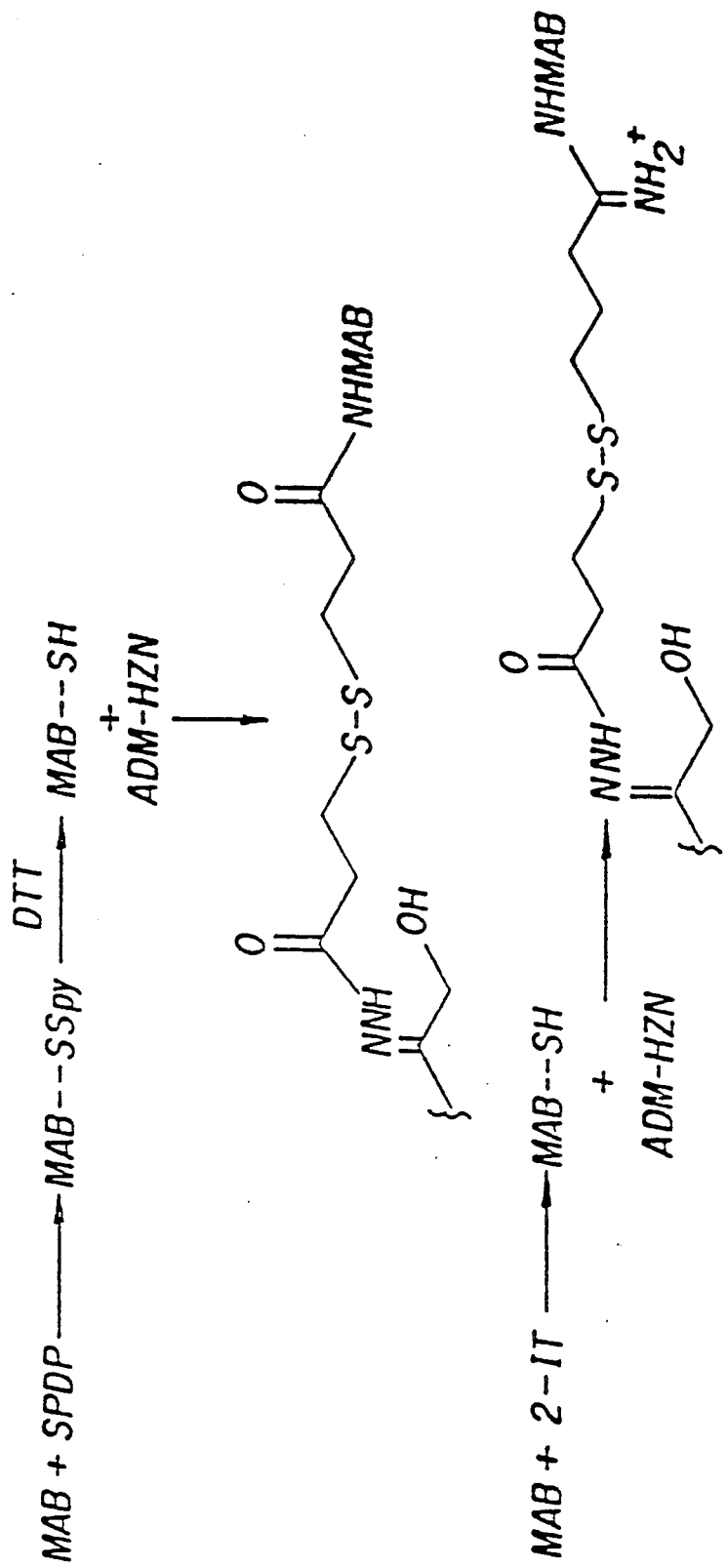
FIG. 2 depicts in schematic form the synthesis of the immunoconjugates of one embodiment of this invention wherein a monoclonal antibody (MAB) was first thiolated using either SPDP (N-succinimidyl-3-(2-pyridyldithio)propionate) or 2-IT (2-iminothiolane) and the thiolated antibody was then reacted with ADM-HZN to form an immunoconjugate of the invention, with a hydrazone bond at the 13-keto position of the ADM and a disulfide bond within the linker arm.

In order that the invention herein disclosed may be more fully understood, the following detailed description is set forth.

The present invention relates to novel anthracycline conjugates, novel anthracycline acylhydrazone derivatives, methods for their production, pharmaceutical compositions and methods for delivering cytotoxic anthracyclines to a selected population of cells desired to be eliminated, in the treatment of diseases such as cancers and other tumors, non-cytocidal viral or other pathogenic infections, and autoimmune disorders. More particularly, the invention relates to anthracycline conjugates comprising at least one anthracycline molecule linked to a molecule that is reactive with a selected cell population sought to be eliminated, the anthracycline being linked to the cell-reactive molecule via a 13-keto acylhydrazone bond. The cell-reactive molecule can be a protein such as an antibody or a ligand such as bombesin or EGF.

Thus, according to one preferred embodiment, the invention relates to immunoconjugates comprised of an antibody directed against a selected cell population, the antibody having a number of anthracycline molecules linked to its structure. The anthracycline molecules are covalently bound to the antibody such that a linker arm is formed between each drug molecule and the antibody, the linker being attached to the anthracycline by an acylhydrazone bond at the 13-keto position of the anthracycline. According to another preferred embodiment, the invention encompasses anthracycline-ligand conjugates comprised of a ligand, such as a polypeptide or peptide ligand, that reacts With one or more receptors associated with the cell surface of a selected cell population, the ligand having at least one anthracycline molecule linked to its structure. The anthracycline is covalently bound to the peptide by a linker arm that is attached to the anthracycline at the 13-keto position of the anthracycline via an acylhydrazone bond.

The conjugates of this invention can be prepared in a stepwise fashion by the initial formation of a novel anthracycline-hydrazone derivative which is then reacted with a protein or ligand of the appropriate specificity [see, e.g., R. R. Hardy, "Purification And Coupling Of Fluorescent Proteins For Use In Flow Cytometry", in *Handbook Of Experimental Immunology*, Volume 1: Immunochemistry, D. M. Weir et al. (eds.), pp. 31.4–31.12 (4th Ed. 1986) for a discussion of conventional antibody coupling techniques and J. M. Varga et al., supra, for the preparation of ligand conjugates]. The length of the linker arm that connects the anthracycline with the cell-reactive component of the conjugates may vary as long as the point of attachment of the linker to the anthracycline is in the form of an acylhydrazone at the C-13 position of the anthracycline. The linker arm may additionally contain another bond, such as a disulfide, thioether, amide, carbamate, ether or ester bond, along its length between the points of attachment from the drug to the cell-reactive molecule.

The anthracyclines that comprise the conjugates of this invention may be any anthracycline containing a keto group at the 13-carbon (C-13) position. Such anthracyclines include, but are not limited to, adriamycin, daunomycin, detorubicin, carminomycin, idarubicin, epirubicin, esorubicin, 4'-THP-adriamycin, AD-32, and 3'-deamino-3'-(3-cyano-4-morpholinyl)-doxorubicin [see A. M. Casazza, "Experimental Studies On New Anthracyclines" in *Adriamycin: Its Expanding Role In Cancer Treatment*, M. Ogawa et al. eds.), pp. 439–52 (Excerpta Medica 1984)].

It is to be understood that the cell-reactive molecule to which the anthracycline is linked in the conjugate, can be any molecule that binds to or reacts with the cell population sought to be eliminated. Such molecules include, but are not limited to, large molecular weight proteins (generally, greater than 10,000 daltons) such as antibodies, smaller molecular weight proteins (generally, less than 10,000 daltons), polypeptide or peptide ligands, and non-peptidyl ligands.

Thus, antibodies that comprise the immunoconjugates of this invention may be any antibody reactive with a specific cell population desired to be eliminated or killed. Examples of such antibodies include, but are not limited to, antibodies that bind to tumor-associated antigens such as antigens found on carcinomas, melanomas, lymphomas, bone or soft tissue sarcomas, as well as other tumors, antibodies that bind to virus- or other pathogen-associated antigens, and antibodies that bind to abnormal cell surface antigens. These antibodies may be polyclonal or preferably, monoclonal and can be produced using techniques well established in the art [see, e.g., R. A. DeWeger et al., "Eradication Of Murine Lymphoma And Melanoma Cells By Chlorambucil-Antibody Complexes", *Immunological Rev.*, 62, pp. 29–45 (1982) (tumor-specific polyclonal antibodies produced and used in conjugates) and M. Yeh et al., "Cell Surface Antigens Of Human Melanoma Identified By Monoclonal Antibody," *Proc. Natl Acad. Sci.*, 76, pp. 2927–31 (1979) and J. P. Brown et al., "Structural Characterization Of Human Melanoma-Associated Antigen p97 With Monoclonal Antibodies," *J. Immunol.*, 127 (No.2), pp. 539–46 (1981) (tumor-specific monoclonal antibodies produced)]. For example, the monoclonal antibody, L6, specific for human lung carcinoma cells or the monoclonal antibody, 791T/36, specific for osteogenic sarcoma cells, can be used. Furthermore, non-internalizing or preferably, internalizing antibodies may be used. The term "antibody" as used in this application includes intact antibody molecules or fragments containing the active binding region of the antibody molecule, e.g., Fab or F(ab')$_2$. If monoclonal antibodies are used, the antibodies may be of, but are not limited to, mouse or human origin or chimeric antibodies.

It is also to be understood the the term "ligand" as used herein includes any molecule that binds specifically to a receptor associated with the cell surface of a selected target cell population. Preferred ligands that can be used to form the anthracycline-ligand conjugates of this invention include, but are not limited to, protein, polypeptide, or peptide ligands such as transferrin, EGF, bombesin, gastrin, gastrin-releasing peptide, platelet-derived growth factor, IL-2, IL-6, TGF-$\alpha$, VGF, TGF-$\beta$, insulin and insulin-like growth factors I and II. Other non-peptidyl ligands include steroids, carbohydrates and lectins.

Thus, the cell-reactive molecule, e.g., antibody or ligand, of the conjugates of this invention acts to deliver the anthracycline molecules to the particular cell population with which the antibody or ligand is reactive. For example, an antibody directed against an antigen found on the surface of tumor cells will bind to and deliver its anthracyclines to those tumor cells or an antibody directed against a protein of the Human Immunodeficiency Virus (HIV) that causes AIDS will deliver its cytotoxic anthracyclines to HIV-infected cells. Similarly, because tumor cells, such as carcinomas, preferentially express certain receptors at high density, such as the EGF receptor, a ligand such as EGF will bind to and deliver its anthracycline to carcinoma cells.

Release of the drug within or at the site of the particular cell population with which the antibody or ligand reacts results in the preferential killing of those particular cells. Thus, it is apparent that the conjugates of this invention are useful in the treatment of any disease wherein a specific cell population is sought to be eliminated, the cell population having a cell surface antigen or receptor which allows binding of the conjugate. Diseases for which the present conjugates are useful include, but are not limited to, cancers and other tumors, non-cytocidal viral or other pathogenic infections such as AIDS, herpes, CMV (cytomegalovirus), EBV (Epstein Barr Virus), and SSPE (subacute schlerosis panencephalitis), and rheumatoid arthritis.

Without being bound by theory, it is believed that the antibody- or ligand-linked anthracycline molecules, i.e., in the form of the conjugate of the invention, ere delivered to the target cells to be killed via the antibody or ligand specificity and may then enter the cell via the same endocytic pathway that leads to internalization of membrane-bound unconjugated antibodies and ligands [see, e.g., I. Pastan et al., "Pathway Of Endocytosis", in *Endocytosis,* I. Pastan et al. (eds.), pp. 1–44 (Plenum Press 1985)]. Once inside the cell, the endocytic vesicles containing the conjugate fuse with primary lysosomes to form secondary lysosomes [see, e.g., M. J. Embleton et al., supra, at p. 334]. Because the anthracycline molecules are bound to the antibody or ligand component of the conjugate via acid-sensitive acylhydrazone bonds, exposure of the conjugate to the acid environment of the endocytic vesicles and lysosomes results in the release of the anthracycline from the conjugate. Furthermore, the anthracycline released is believed to be a relatively unmodified drug capable of full cytotoxic activity. Thus, the acid-sensitive hydrazone bond of the conjugate is highly advantageous for the release of the cytotoxic drug within target cells, enhancing the cytotoxicity of the conjugate toward those cells. Alternatively, the hydrazone bond may be cleaved under acidic and reducing conditions in the immediate environment external to or surrounding the target cells, e.g., at the site of a tumor, and the released drug may be taken up by the tumor cells.

Immunoconjugates of the invention and the methods for their production are exemplified by preferred embodiments in which the anthracycline, adriamycin, was conjugated to various antibodies.

First, a novel adriamycin hydrazone derivative was synthesized in a two-step reaction. The heterobifunctional reagent SPDP (N-succinimidyl-3-(2-pyridyldithio)propionate) was allowed to react with hydrazine to form a 3-(2-pyridyldithio) propionyl hydrazide and the hydrazide was then reacted with adriamycin hydrochloride (ADM-HCl) to form a novel acylhydrazone derivative of ADM, containing a pyridyl-protected disulfide moiety. An acid catalyst such as trifluoroacetic acid may be employed to facilitate the formation of hydrazone. The derivative formed was designated adriamycin 13-{3-(2-pyridyldithio) propionyl}hydrazone hydrochloride (ADM-HZN) (see FIG. 1).

This novel ADM-hydrazone derivative was then reacted with a monoclonal antibody that had been previously thiolated with SPDP and then reduced or thiolated with 2-IT (2-iminothiolane) (see FIG. 2). The resulting immunoconjugate was comprised of ADM molecules conjugated to the monoclonal antibody by means of a linker arm attached to the C-13 position of each ADM through an acylhydrazone bond, the linker arm additionally containing a disulfide bond through which it was attached to the antibody (see FIG. 2).

Figure 17:
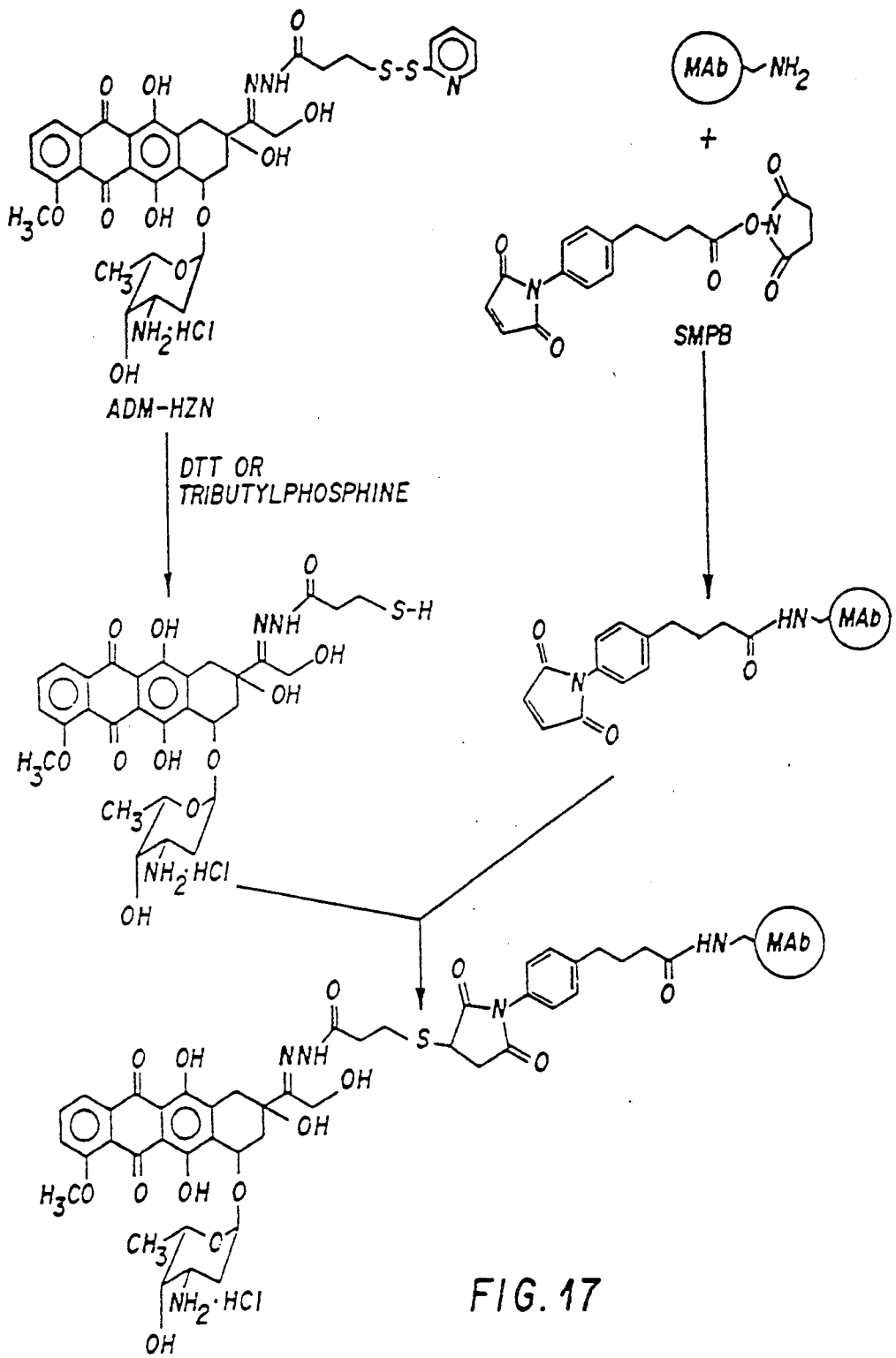
FIG. 17 depicts in schematic form the synthesis of an immunoconjugate of this invention wherein the novel ADM-HZN derivative of this invention is reduced and then reacted with a SMPB (succinimidyl-4-(p-maleimidophenyl)butyrate)-treated antibody to form an immunoconjugate having a linker arm with a thioether linkage within its structure.

Another embodiment of the invention involved the synthesis of another novel adriamycin hydrazone derivative wherein the ADM-HZN described above was further treated with the reducing agents, DTT (dithiotreitol) or tributylphosphine, to produce 13-{3-(mercaptopropionyl)}adriamycin hydrazone (see FIG. 17). This derivative was then reacted with a monoclonal antibody to which maleimide groups had been attached, for example, by reaction of the antibody with SMPB (succinimidyl-4-(p-maleimidophenyl)butyrate). As shown in FIG. 17, an immunoconjugate was formed having a linker arm attached by a hydrazone bond to the C-13 position of each ADM and also having a thioether linkage as part of its attachment to the antibody. Thus, it is apparent that the linker arm connecting the drug and antibody may be comprised of a number of constituents and linkages as long as these linkages include the acid-sensitive hydrazone bond at the 13-keto position of the anthracycline.

According to another embodiment, the novel ADM-HZN derivative of the invention was reacted with either of the ligands, bombesin, EGF or transferrin, the ligand having been first derivatized to possess thiol groups. In the case of bombesin, a cysteine residue was introduced onto the amino terminus of the peptide to provide a reactive sulfhydryl group for conjugation with ADM-HZN. In the case of murine EGF, the polypeptide was reacted with SPDP to introduce a reactive sulfhydryl group at the amino terminus of the molecule for conjugation with ADM-HZN. In the case of transferrin, the protein was first reacted with 2-IT to introduce reactive thiol groups onto the protein structure. In each case, the thiolated ligand was then reacted with ADM-HZN to form an anthracycline-ligand conjugate of the invention having a linker between the ligand and the drug, the linker being attached to the C-13 position of each anthracycline through an acylhydrazone bond. Additionally, the linker contained a disulfide bond within its structure (see FIG. 27). Alternatively, ADM-HZN can be reduced with DTT (as described above for the preparation of immunoconjugates) and then reacted with a ligand to which maleimide groups have been attached, also as described above. An ADM-ligand conjugate would thus be produced having a linker arm attached by a hydrazone bond to the C-13 position of the ADM, the linker arm also containing a thioether bond within its structure.

It is also apparent that the present invention provides novel acylhydrazone derivatives of 13-keto-containing anthracyclines having formulae I, II or III:

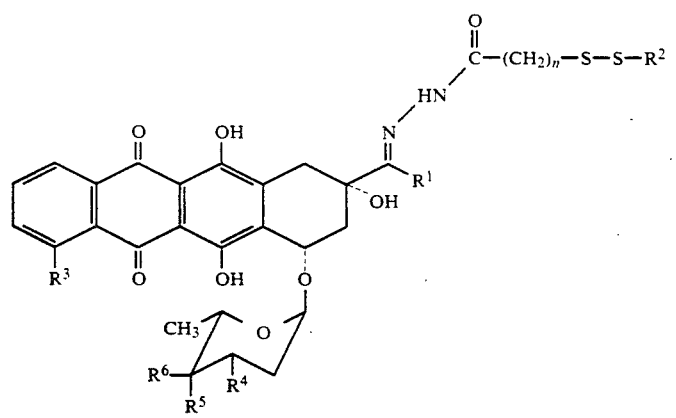

Formula I wherein:
$R^1$ is $CH_3$, $CH_2OH$, $CH_2OCO(CH_2)_3CH_3$, $CH_2OCOCH(OC_2H_5)_2$;
$R^2$ is

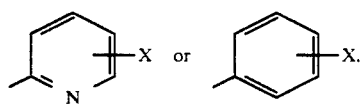

-continued wherein
X = H, $NO_2$ or halogen
$R^3$ is $OCH_3$, OH or hydrogen;
$R^4$ is $NH_2$, $NHCOCF_3$, 4-morpholinyl, 3-cyano-4-morpholinyl, 1-piperidinyl, 4-methoxy-1-piperdinyl, benzyl amine, dibenzyl amine, cyanomethyl amine or 1-cyano-2-methoxyethyl amine;
$R^5$ is OH, O-THP or hydrogen;
$R^6$ is OH or hydrogen, provided that $R^6$ is not OH when $R^5$ is OH or O-THP; and
n is an integer from 1 to 10, inclusive;

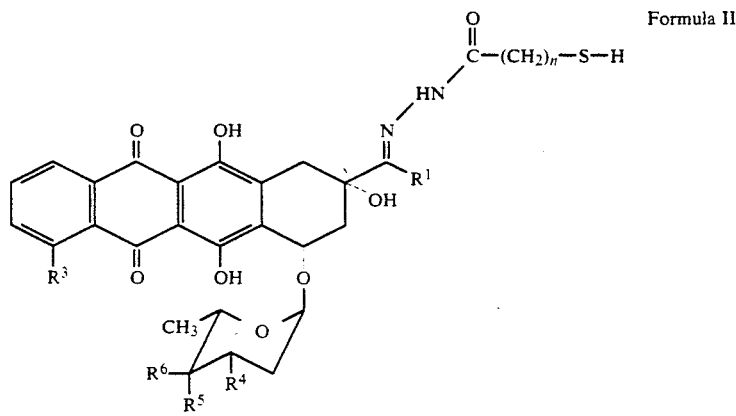

Formula II wherein:
$R^1$ is $CH_3$, $CH_2OH$, $CH_2OCO(CH_2)_3CH_3$, $CH_2OCOCH(OC_2H_5)_2$;
$R^3$ is $OCH_3$, OH or hydrogen;
$R^4$ is $NH_2$, $NHCOCF_3$, 4-morpholinyl, 3-cyano-4-morpholinyl, 1-piperidinyl, 4-methoxy-1-piperdinyl, benzyl amine, dibenzyl amine, cyanomethyl amine or 1-cyano-2-methoxyethyl amine:
$R^5$ is OH, O-THP or hydrogen;
$R^6$ is OH or hydrogen, provided that $R^6$ is not OH when
$R^5$ is OH or O-THP; and
n is an integer from 1 to 10, inclusive; and

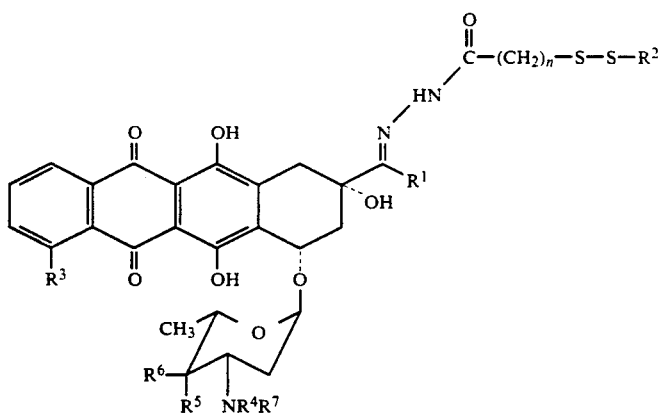

Formula III wherein:

$R^1$ is $CH_3$, $CH_2OH$, $CH_2OCO(CH_2)_3CH_3$, $CH_2OCOCH(OC_2H_5)_2$;

$R^2$ is

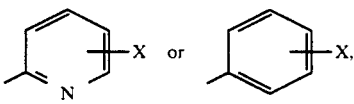

wherein
X = H, $NO_2$ or halogen $R^3$ is $OCH_3$, OH or hydrogen;

$R^4$ and $R^7$ are independently hydrogen, alkyl, substituted alkyl, cycloalkyl, substituted cycloalkyl, aryl, substituted aryl, aralkyl or substituted aralkyl; or $R^4$, $R^7$ and N together form a 4–7 membered ring, wherein said ring may be optionally substituted;

$R^5$ is OH, O-THP or hydrogen;

$R^6$ is OH or hydrogen, provided that $R^6$ is not OH when $R^5$ is OH or O-THP; and n is an integer from 1 to 10, inclusive The above-disclosed anthracycline acylhydrazones represent novel intermediates in the preparation of the conjugates of the invention and are exemplified by ADM-HZN and 13-{3-(mercaptopropionyl)}adriamycin hydrazone, respectively as described in the preferred embodiments discussed herein.

As can be seen from the above formulae, the acylhydrazone intermediates of the invention include hydrazones of any of a number of known anthracyclines such as adriamycin, daunomycin and carminomycin. In addition, the intermediates include acylhydrazones derivatized at specific sites on the anthracycline structure (e.g., 4'-THP-adriamycin hydrazone and 3'-deamino-3'-(3-cyano-4-morpholinyl)adriamycin hydrazone). These latter intermediates can be synthesized by first derivatizing the anthracycline to form a desired analog and then using that analog to prepare the hydrazone intermediate of the invention. Known anthracycline analogs include those described in U.S. Pat. Nos. 4,464,529 and 4,301,277 (3'-deamino-3'-(4-morpholinyl) or 3'-deamino-3'-(3-cyano-4-morpholinyl) anthracycline analogs), U.S. Pat. Nos. 4,202,967 and 4,314,054 (3'-deamino-3'-(1-piperdinyl) or 3'-deamino-3'-(4-methoxy-1-piperdinyl) anthracyline analogs), U.S. Pat. No. 4,250,303 (N-benzyl or N,N-dibenzyl anthracycline analogs), U.S. Pat. No. 4,591,637 (N-methoxymethyl or N-cyanomethyl anthracycline analogs) and U.S. Pat. No. 4,303,785 (acetal analogs of anthracyclines). Thus, these known anthracycline analogs can be reacted as described hereinabove (see FIG. 1) to produce novel acylhydrazones which can then be conjugated to an antibody or ligand of a desired specificity as described herein.

Alternatively, an underivatized acylhydrazone intermediate of this invention can first be produced as described herein from the underivatized anthracycline, such as adriamycin, daunomycin or carminomycin, and this novel intermediate then derivatized to produce a novel acylhydrazone substituted as desired. For example, ADM-HZN can be derivatized at its amino sugar moiety by reductive amination with 2,2'-oxydiacetaldehyde using the procedure described in U.S. Pat. No. 4,464,529, to produce 3'-deamino- 3'-(3-cyano-4-morpholinyl)adriamycin hydrazone. Similarly, ADM-HZN can be derivatized at the amino sugar moiety to produce novel acylhydrazone derivatives such as 3'-deamino-3'-(4-morpholinyl) ADM hydrazone (see U.S. Pat. No. 4,301,277), 3'-deamino-3'-(1-piperdinyl) ADM hydrazone (see U.S. Pat. No. 4,202,967), 3'-deamino-3'-(4-methoxy-1-piperdinyl) ADM hydrazone (see U.S. Pat. No. 4,314,054), N-benzyl ADM hydrazone and N,N-dibenzyl ADM hydrazone (see U.S. Pat. No. 4,250,303) or N-methyoxymethyl ADM hydrazone and N-cyanomethyl ADM hydrazone (see U.S. Pat. No. 4,591,637). In addition, ADM-HZN can be derivatized at the $R^5$ position of Formulae I-III as described in U.S. Pat. No. 4,303,785 to produce acetal derivatives of the hydrazone such as 4'-THP-ADM hydrazone.

It should be understood that these novel procedures for derivatizing the acylhydrazones of the invention can utilize as starting materials hydrazones of anthracyclines other than ADM, such as daunomycin or carminomycin, to produce novel compounds such as N-benzyl daunomycin hydrazone or 3'-deamino-3'-(4-morpholinyl)carminomycin hydrazone, which are also within the scope of this invention.

Evaluation of the anthracycline-antibody immunoconjugates prepared according to this invention showed that the immunoconjugates retained antibody binding activity and exhibited antibody-directed cell killing for both lymphoma and carcinoma cells under various assay conditions. Thus, cells possessing the antigen to which the antibody of the conjugate was directed were efficiently killed by the anthracycline whereas cells that did not possess the appropriate antigen were not killed. In fact, in several experiments, antibody-delivered anthracycline was found to be more potent than equivalent amounts of unconjugated anthracycline. Differences in uptake mechanisms into the tumor cell and intracellular transport mechanisms may be responsible for the potency differences observed between the free drug and the antibody-conjugated drug.

Furthermore, studies using human tumor xenografts in mice have demonstrated the ability of the immunoconjugates of this invention to inhibit tumor growth in vivo, leading in some cases to complete tumor regression. The immunoconjugates were shown to possess a greater potency and inhibited tumor growth to a greater extent than the unconjugated anthracycline. Furthermore, the immunoconjugates were tolerated by the animals to a much greater extent than the free drug, being at least 10 times less toxic than the unconjugated anthracycline alone.

The binding and cytotoxicity properties of the immunoconjugates of this invention appear to represent an improvement over immunoconjugates reported in the literature in which anthracyclines were directly linked to antibody through the amino sugar portion of the anthracycline. Those amino sugar-linked immunoconjugates often contained lower anthracycline to antibody molar ratios and exhibited reduced cytotoxicity relative to the free drug and reduced antibody binding properties [see, e.g., R. Arnon et al., *Immunological Rev.*, 62, supra; E. Hurwitz et al., *Cancer Res.*, 35, supra; and R. Yamamato et al., supra]. Furthermore, stability studies performed on the immunoconjugates of this invention indicated that the anthracycline was released from the immunoconjugates under reducing and acidic conditions similar to those found in a cellular environment. Thus, the retention of high cytotoxic drug activity observed with the immunoconjugates described herein may be explained by the fact that a relatively unmodified drug is delivered to the target cells.

In addition, we were able to optimize reaction conditions such that anthracycline:antibody molar ratios of approximately 4-10 were reached, using several antibodies of different isotypes. The amount of protein recovered after condensation with the ADM-HZN derivative dropped off dramatically when molar ratios greater than 10 were attempted. It appeared that the major limitation in obtaining immunoconjugates with molar ratios greater than 10 was due to the reduced solubility of the conjugates in aqueous solution and the physical association of anthracycline with protein.

In vitro studies have also demonstrated the ability of the anthracycline-ligand conjugates of this invention to kill target cells. For example, our studies have demonstrated that certain anthracycline-ligand conjugates of this invention retained their specific receptor binding activity while exhibiting cytotoxicity toward tumor cells. Thus, a cys-bombesin-ADM conjugate prepared as described herein demonstrated a binding activity to a bombesin receptor-positive cell line equivalent to that observed with unconjugated cys-bombesin and was highly cytotoxic to a transformed fibroblast cell line in vitro. In fact, the cys-bombesin-ADM conjugate was more potent then free ADM or ADM-HZN. In addition, an EGF-ADM conjugate as well as a transferrin-ADM conjugate were prepared as described herein.

Our in vivo studies showing the enhanced anti-tumor activity of the immunoconjugates of this invention over the free drug as well as their reduced systemic toxicity, indicate an increased therapeutic index for the conjugates. Thus, the present invention also encompasses pharmaceutical compositions, combinations and methods for treating diseases such as cancers and other tumors, non-cytocidal viral or other pathogenic infections, and autoimmune diseases. More particularly, the invention includes methods for treating disease in mammals wherein a pharmaceutically effective amount of at least one anthracycline-containing conjugate is administered in a pharmaceutically acceptable manner to the host mammal.

Alternative embodiments of the methods of this invention include the administration, either simultaneously or sequentially, of a number of different conjugates, i.e., bearing different anthracyclines or different antibodies or ligands, for use in methods of combination chemotherapy. For example, an embodiment of this invention may involve the use of a number of anthracycline-immunoconjugates wherein the specificity of the antibody component of the conjugate varies, i.e., a number of immunoconjugates are used, each one having an antibody that binds specifically to a different antigen or to different sites or epitopes on the same antigen present on the cell population of interest. The anthracycline component of these immunoconjugates may be the same or may vary. For example, this embodiment may be especially useful in the treatment of certain tumors where the amounts of the various antigens on the surface of a tumor is unknown or the tumor cell population is heterogenous in antigen expression and one wants to be certain that a sufficient amount of drug is targeted to all of the tumor cells at the tumor site. The use of a number of conjugates bearing different antigenic or epitope specificities for the tumor increases the likelihood of obtaining sufficient drug at the tumor site. Additionally, this embodiment is important for achieving a high degree of specificity for the tumor because the likelihood that normal tissue will possess all of the same tumor-associated antigens is small [cf., I. Hellstrom et al., "Monoclonal Antibodies To Two Determinants Of Melanoma-Antigen p97 Act Synergistically In Complement-Dependent Cytotoxicity", *J. Immunol.*, 127 (No. 1), pp. 157–60 (1981)].

Alternatively, a number of different immunoconjugates can be used, wherein only the anthracycline component of the conjugate varies. For example, a particular antibody can be linked to adriamycin to form one immunoconjugate and can be linked to daunomycin to form a second immunoconjugate. Both conjugates can then be administered to a host to be treated and will localize, due to the antibody specificity, at the site of the selected cell population sought to be eliminated. Both drugs will then be released at that site. This embodiment may be important where there is some uncertainty as to the drug resistance of a particular cell population such as a tumor because this method allows the release of a number of different drugs at the site of or within the target cells. An additional embodiment includes the conjugation of more than one anthracycline to a particular antibody to form an immunoconjugate bearing a variety of different anthracycline molecules along its surface—all linked to the antibody via a 13-keto acylhydrazone bond. Administration of the immunoconjugate of this embodiment results in the release of a number of different drugs at the site of or within the target cells. Furthermore, a combination of anthracycline-antibody and anthracycline-ligand conjugates can be used wherein the drug can be targeted to a cell population carrying a specific antigen as well as a receptor for a specific ligand on its surface. Again, one type of anthracycline or a number of different drugs can be used in this combination therapy.

The anthracycline conjugates of the invention can be administered in the form of pharmaceutical compositions using conventional modes of administration including, but not limited to, intravenous, intraperitoneal, oral, intralymphatic, or administration directly into the site of a selected cell population such as a tumor. Intravenous administration is preferred. In the case of the immunoconjugates, for in vivo treatment, it may be useful to use conjugates comprising antibody fragments such as Fab or F(ab')$_2$ or chimeric antibodies.

The pharmaceutical compositions of the invention—comprising the anthracycline conjugates—may be in a variety of dosage forms which include, but are not limited to, solid, semi-solid and liquid dosage forms such as tablets, pills, powders, liquid solutions or suspensions, suppositories, polymeric microcapsules or microvesicles, liposomes, and injectable or infusible solutions. The preferred form depends upon the mode of administration and the therapeutic application.

The pharmaceutical compositions may also include conventional pharmaceutically acceptable carriers known in the art such as serum proteins such as human serum albumin, buffer substances such as phosphates, water or salts or electrolytes.

The most effective mode of administration and dosage regimen for the conjugate compositions of this invention depends upon the severity and course of the disease, the patient's health and response to treatment and the judgment of the treating physician. Accordingly, the dosages of the conjugates and any accompanying compounds should be titrated to the individual patient. Nevertheless, an effective dose of the anthracycline immunoconjugate of this invention may be in the range of from about 1 to about 100 mg/m$^2$ anthracycline or from about 500–5000 mg/m$^2$ antibody. An effective dose of the anthracycline-ligand conjugates may be in the range of from about 1 to about 100 mg/m$^2$ anthracycline or from about 1 to about 100 mg/m$^2$ ligand.

In order that the invention described herein may be more fully understood, the following examples are set forth. It should be understood that these examples are for illustrative purposes only and are not to be construed as limiting the scope of this invention in any manner.

EXAMPLE 1

The following example demonstrates the production of a novel anthracycline immunoconjugate according to the present invention wherein the drug is linked directly to a monoclonal antibody via a hydrazone bond at the 13-keto position of the drug.

The particular embodiment described in this example involves the conjugation of ADM to a monoclonal antibody to form an immunoconjugate having a linker arm with an acylhydrazone bond as its point of attachment to the ADM molecule of the immunoconjugate, the linker additionally having a disulfide bond as part of its attachment to the antibody. This embodiment also provides a novel acylhydrazone derivative of ADM (ADM-HZN).

Synthesis Of An Adriamycin Hydrazone

As the initial step in the preparation of the immunoconjugate of this embodiment, an ADM-hydrazone derivative was first synthesized as follows: 0.3 ml of 1M hydrazine, i.e., NH$_2$NH$_2$, solution in isopropyl alcohol was added to a cooled solution of SPDP (70 mg, 0.22 mmol) in 3 ml of THF (tetrahydrofuran) After stirring 20 min at 0° C., the product was extracted with CH$_2$Cl$_2$, washed with brine and dried over K$_2$CO$_3$. The residue obtained after evaporation of the solvents was chromatographed on neutral alumina (5% MeOH, 95% CH$_2$Cl$_2$) to give 21 mg (41%) of 3-(2-pyridyldithio) propionyl hydrazide (compound 2 in FIG. 1). This hydrazide and adriamycin HCl (obtained from Sanraku Inc., Japan) (48 mg, 0.083 mmol) were dissolved in 5 ml of MeOH and then stirred in the dark at room temperature for 6 days. The reaction was followed by reverse phase thin layer chromatography (TLC) (MeOH:-H$_2$O=2:1, containing 3% w/v NH$_4$OAc). After this period, the solvent was evaporated and the residue was chromatographed on a C18 column (MeOH:H$_2$O=3:2, containing 3% w/v NH$_4$OAc). The fractions were combined and lyophilized and excess NH$_4$OAc was removed under reduced pressure. The residue was dissolved in MeOH and precipitated by addition of acetonitrile to give 45 mg (72%) of adriamycin 13-{3-(2-pyrityldithio) propionyl}-hydrazone hydrochloride, referred to hereinafter as ADM-HZN (compound 4 in FIG. 1). The ADM-HZN was characterized as follows: mp>125° darkens its color and not well-defined; NMR (acetone-d$_6$, δ) 1.25 (s,3H=J=6Hz), 1.77 (m,1H), 2.06 (m,1H), 2.30 (m,1H), 2.53 (d,1H,J=15Hz), 2.89–3.18 (m,6H), 3.71 (m,1H), 3.85 (m,1H), 3.97 (m,1H), 4.07 (s,3H), 4.78 (s,2H), 5.21 (m,1H), 5.58 (t,1H,J=7Hz), 7.12 (m,1H), 7.64 (d,1H,J=8Hz), 7.75 (m,2H), 7.90 (t,1H,J=8Hz), 7.98 (d,1H,J=8Hz), 8.37 (d,1H,J=4Hz), 10.50 (s,1H), 10.52 (s,1H), 14.19 (bs,1H); IR (KBr) 3438, 1674 1618, 1579, 1419, 1286, 1016, 988, 698 cm$^{-1}$; FABMS (glycerol) m/e 755 (M+1), 737, 645, 625, 609.

Thiolation Of Monoclonal Antibodies

Before reacting the ADM-HZN compound prepared as described above with a monoclonal antibody of interest, the antibody had to be thiolated, i.e., reactive sulfhydryl groups had to be introduced onto the antibody molecule.

The monoclonal antibodies utilized were: 1) 5E9, an IgG$_1$ antibody reactive with the transferrin receptor on all dividing human cells and cross-reactive with various histological types of cancer cells; 2) T33A1 (hereinafter referred to as "3A1"), an IgG$_1$ antibody reactive with the 40 Kd human T cell antigen and also found on a number of T cell leukemias; 3) G28.5, an IgG$_1$ antibody reactive with the 50 Kd human B cell antigen and also reactive with human B cell lymphomas; 4) G28.1, an IgG$_1$ antibody reactive with the 39 Kd human B cell antigen and also reactive with B cell lymphomas; and 5) L6, an IgG$_{2a}$ antibody reactive with a glycolipid antigen on human non-small cell lung carcinomas.

Hybridomas secreting the 5E9 and T33A1 monoclonal antibodies were obtained from the American Type Culture Collection (ATCC). The respective antibodies were purified from ascitic fluid produced in BALB/c mice according to the procedure of C. Bruck et al, "One-Step Purification Of Mouse Monoclonal Antibodies From Ascitic Fluid By DEAE-Affigel Blue Chromatography", *J. Immun. Methods.* 5b, pp. 313–19 (1982). Purified G28.5, G28.1, and L6 were provided by Drs. J. Ledbetter and I. Hellstrom (Oncogen, Seattle, Wash.). Hybridomas secreting the L6 and G28.5 monoclonal antibodies were deposited with the ATCC on Dec. 6, 1984 and May 22, 1986, respectively, under ATCC accession nos. HB 8677 and HB 9110. The G28.1 monoclonal antibody is one of a number of antibodies known in the art to be reactive with a major epitope of the CD37 antigen and has been characterized in A. J. Michael (ed.), *Leukocyte Typing III*, Oxford University Press (U.K. 1987). A number of these anti-CD37 antibodies are commercially available.

Thiolation of any of these antibodies with SPDP was carried out as follows: SPDP (Pierce Chemical Co., Ill.) (50 mM), dissolved in ethanol, was added to the monoclonal antibody of choice, e.g., 5E9 (5-10 mg/ml), in PBS (phosphate buffered saline, pH 7.2) to give a final concentration of between 5-10 mM. The reaction mixture was incubated for 30 min at 30° C. Unreacted SPDP was separated from SPDP-derivatized antibody by gel filtration chromatography using a PD-10 column (Pharmacia). The thiopyridyl protecting groups were removed by reduction with excess DTT. The reduced antibodies were passed through a PD-10 column and the free thiol-containing antibodies were used for condensation with the ADM-HZN derivative (see FIG. 2).

Reactive thiol groups were also introduced onto the antibody protein using 2-IT: the antibody (5-10 mg/ml in 50 mM triethylamine, 50 mM NaCl, 1 mM EDTA at pH 8.0) was mixed with 2-IT (Pierce Chemical Co., Ill.) at a final concentration of 5-10 mM. The reaction was allowed to proceed for 90 min at 4° C. and thiolated antibodies were separated on a PD-10 column equilibrated with 2M NaCl/PBS.

The number of reactive thiol groups incorporated onto the antibodies was determined using DTNB (5,5'-dithiobis(2-nitrobenzoic acid) ($E_{412}=14150$), according to the procedure of G. L. Ellman, *Arch. Biochem. Biophys.*, 82, pp. 70-77 (1959).

Conjugation Of Thiolated Monoclonal Antibodies With ADM-HZN

A number of conjugations were next performed wherein monoclonal antibodies thiolated as described above were each linked to ADM-HZN (see FIG. 2).

ADM-HZN was dissolved in methanol and added to SPDP-thiolated antibodies in PBS or to 2-IT-thiolated antibodies in 2M NaCl/PBS. In a typical experiment, 10 equivalents of ADM-HZN were added to monoclonal antibodies containing 10-20 reactive thiol groups. The conjugation reaction was allowed to incubate overnight at 4° C. The reaction mixture was centrifuged at 10,000×g and conjugated ADM was then separated from unreacted ADM by passage through a PD-10 column. The amount of conjugated anthracycline bound to antibody was determined by absorbance at 495 nm ($E_{495}=8030$). The amount of antibody protein was determined by absorbance at 280 nm (1 mg/ml=1.4 OD units). To correct for the overlap of ADM absorbance at 280 nm, the following formula was used:

$$\text{Antibody (mg/ml)} = \frac{A_{280} - (0.72 \times A_{495})}{1.4}$$

Immunoconjugates were analyzed for the presence of unconjugated ADM or ADM derivatives using HPLC analysis. HPLC was done using a Phenomenex column packed with 5 micron IB-SIL C18 beads. Unconjugated ADM-HCl, ADM-HZN (0.1 μmoles), or immunoconjugates containing 0.5-5 μmoles drug equivalents were applied to the column and eluted with methanol and 10 mM ammonium phosphate, pH 4.5 (70:30) at 1.5 ml/min. All of the immunoconjugates produced contained no significant amount (<1%) of unconjugated drug by HPLC analysis.

Characterization Of The Immunoconjugates Of The Invention

The immunoconjugates so produced were comprised of ADM molecules conjugated at the 13-keto position to a linker arm that formed a bridge between the drug and the respective monoclonal antibody. Furthermore, the addition of the monoclonal antibody with free thiol groups to the ADM-HZN derivative which contained a thiopyridyl protected disulfide bond led to the formation of a disulfide bond in the linker joining ADM to the antibodies (see FIG. 2). Immunoconjugates produced according to this embodiment include, but are not limited to, 5E9-ADM-7.5, 3A1-ADM-7.0, L6-ADM-9.0 and G28.1-ADM-9.0, wherein the first part of the designation represents the monoclonal antibody used to form the conjugate, the second part of the designation represents the anthracycline linked to the antibody and the numeral in the designation represents the molar ratio of ADM/antibody in the particular immunoconjugate.

Figure 3:
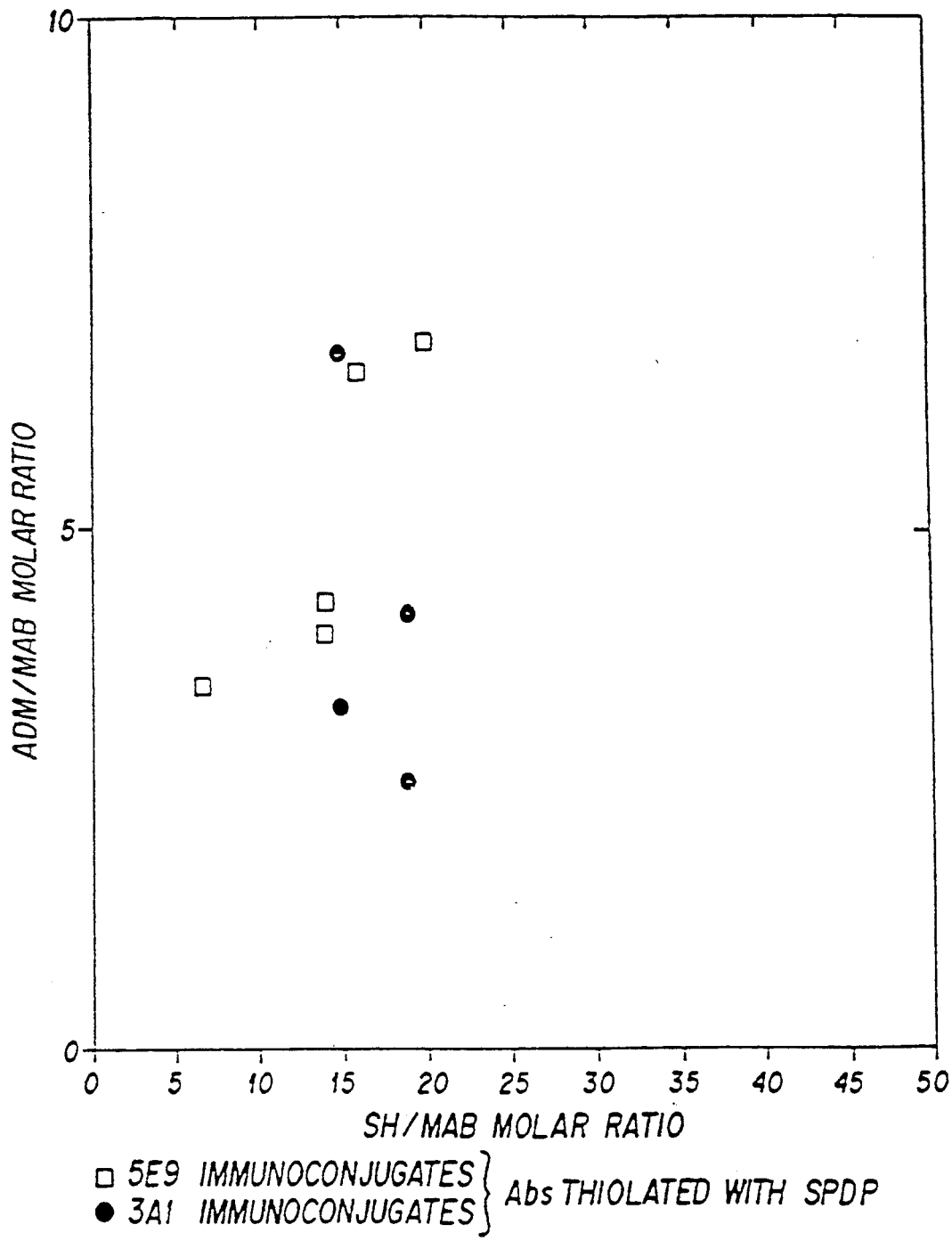
FIG. 3 depicts a scattergram that compares the number of reactive thiol groups substituted on the monoclonal antibody (SH/MAB ratio) to the final ADM-/MAB molar ratio achieved in immunoconjugates produced by the condensation of the SPDP-thiolated 5E9 and 3A1 monoclonal antibodies with ADM-HZN.
Figure 4:
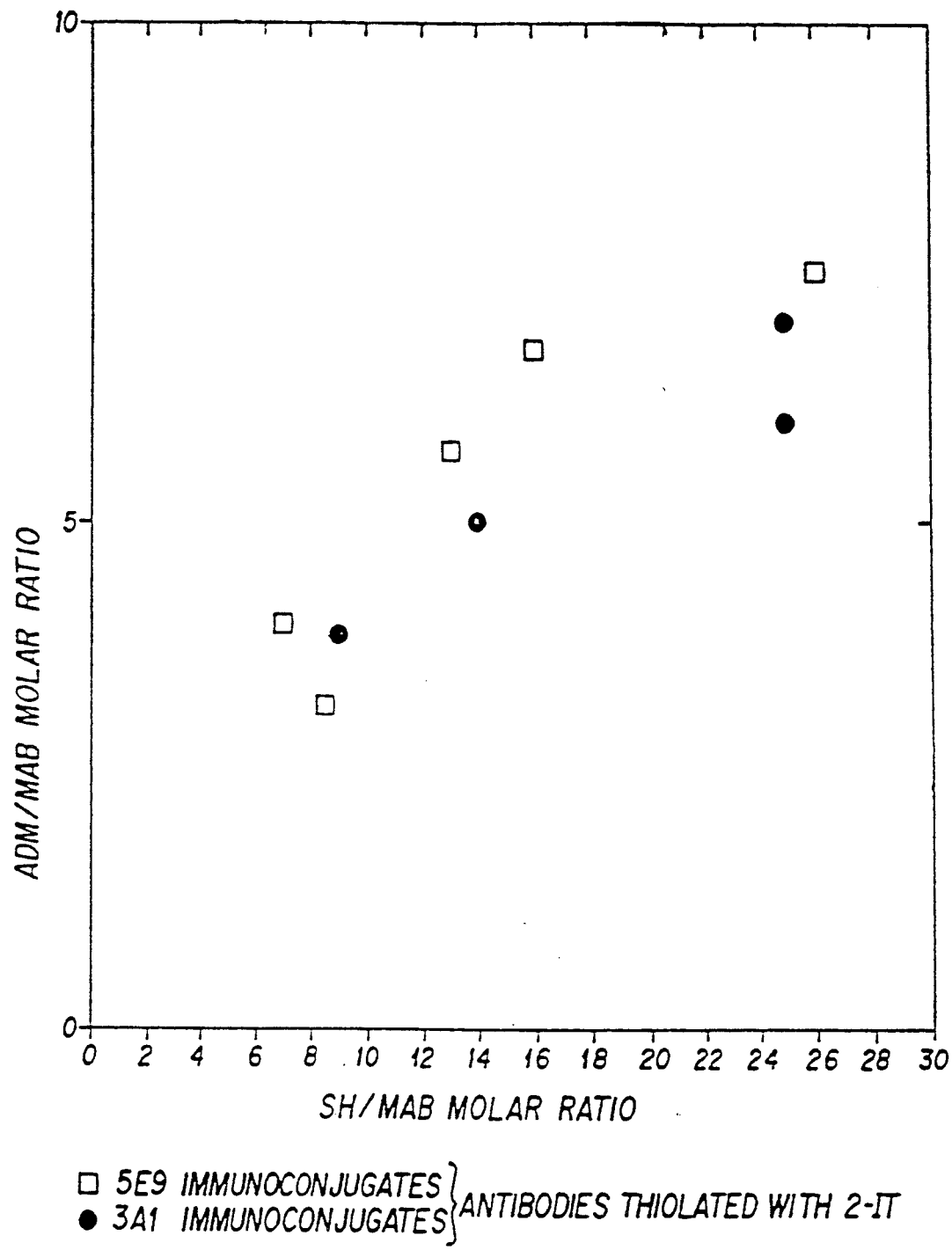
FIG. 4 depicts a scattergram comparing the SH/MAB ratio with the final ADM/MAB molar ratio achieved in immunoconjugates produced by the reaction of 2-IT-thiolated 5E9 and 3A1 antibodies with ADM-HZN.
Figure 5:
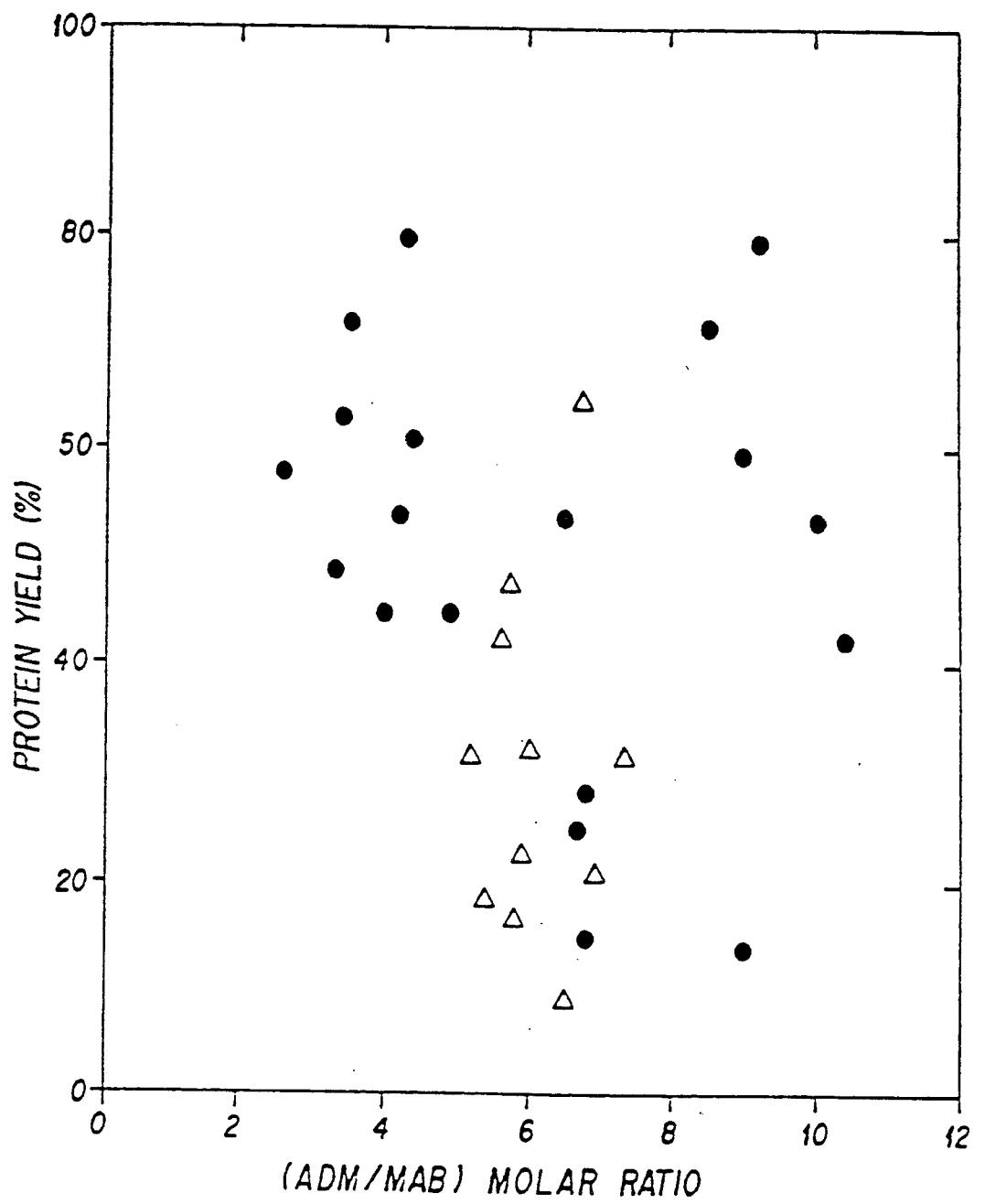
FIG. 5 depicts a scattergram showing the relationship between ADM/MAB molar ratio and the protein yield of immunoconjugates of the invention prepared using either SPDP-thiolated antibodies or 2-IT-thiolated antibodies.
Figure 6:
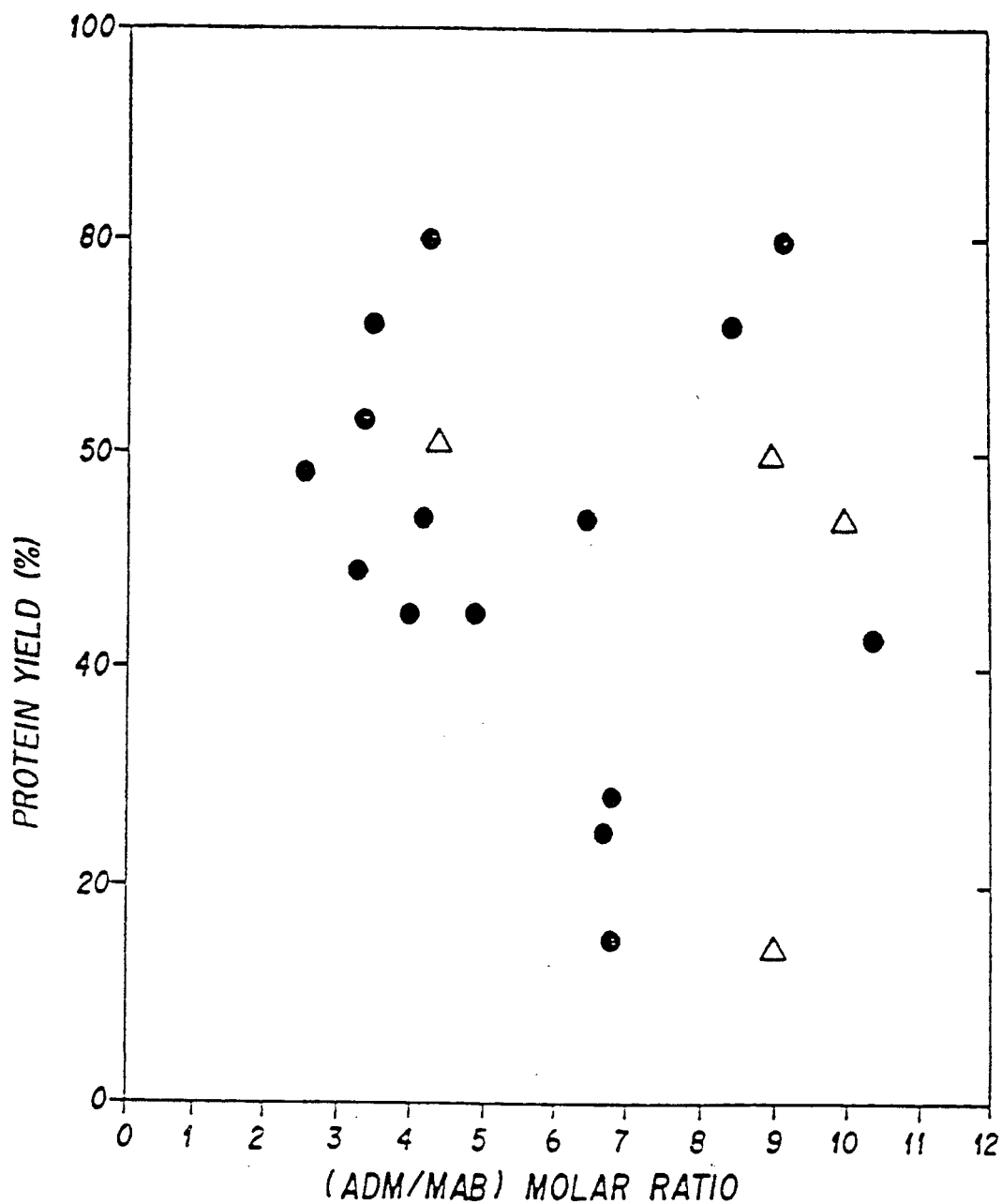
FIG. 6 depicts a scattergram comparing the ADM/MAB molar ratio vs. protein yield obtained in immunoconjugate preparations using monoclonal antibodies of either the $IgG_1$ isotype (e.g., 5E9 and 3A1) or the $IgG_2$ isotype (e.g., L6). These antibodies had been thiolated with SPDP.
Figure 7:
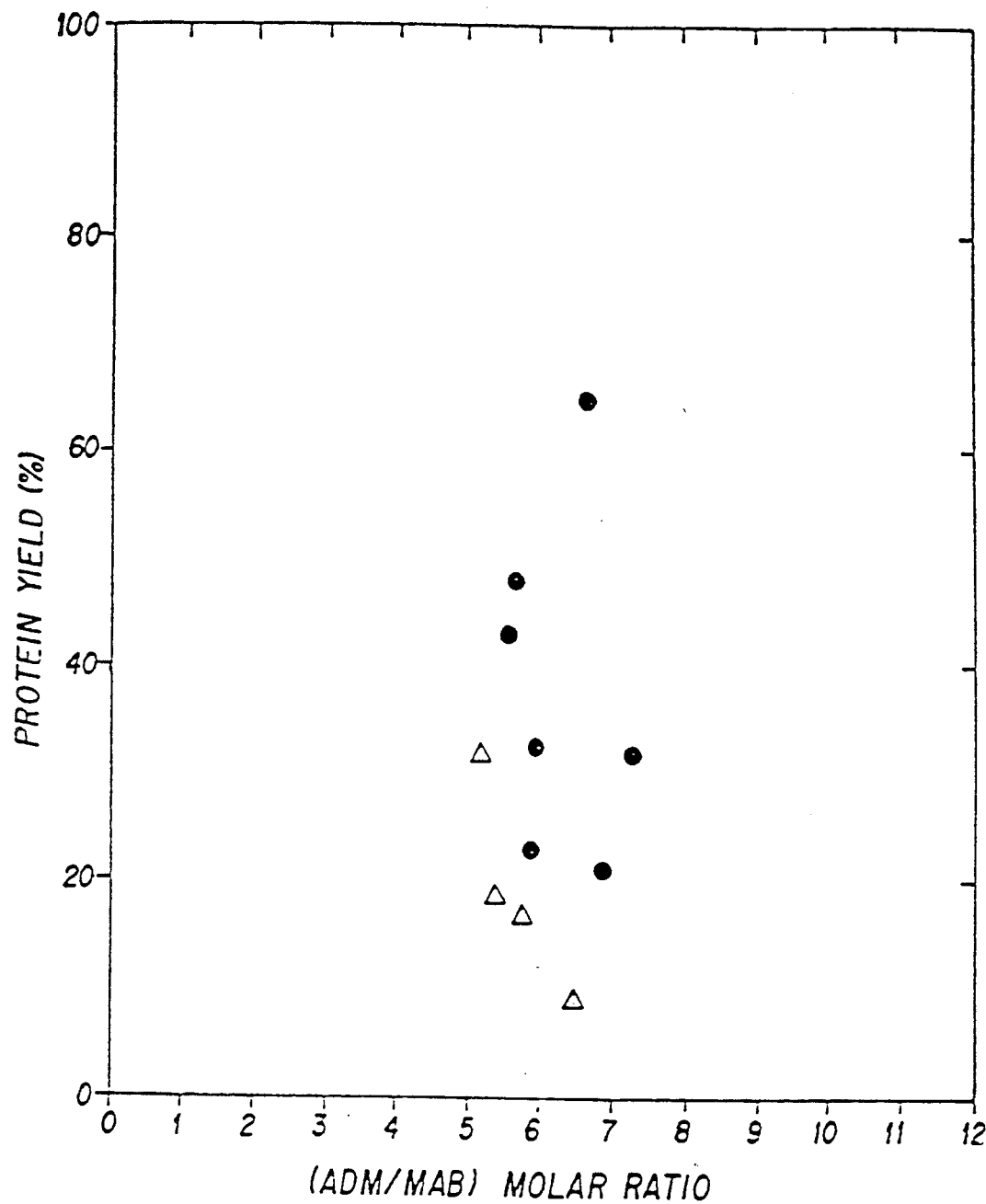
FIG. 7 also depicts a scattergram comparing the ADM/MAB molar ratio vs. protein yield of immunoconjugates having antibodies of the $IgG_1$ vs. $IgG_2$ isotypes (as in FIG. 6) except that these antibodies had been thiolated using 2-IT.

The ADM/antibody molar ratios achieved according to this embodiment depended upon the number of thiol groups introduced onto the monoclonal antibody and the amount of ADM-HZN derivative added to the thiolated antibody. The scattergrams in FIGS. 3 and 4 show that ADM/antibody ratios of 3-4 were achieved when ADM-HZN was condensed with either the 5E9 or 3A1 monoclonal antibody containing approximately eight thiol groups. Typically, a 10-fold molar excess of ADM-HZN to protein was added in these reactions. ADM/antibody ratios increased to 8-10 when those antibodies having 18-25 thiol groups were used. No significant differences in the ADM/antibody ratios were observed when using SPDP vs. 2-IT to thiolate the monoclonal antibody (compare FIGS. 3 and 4). However, final protein yields following conjugation of drug to antibody appeared to be somewhat higher with SPDP-thiolated antibodies as compared to 2-IT-thiolated antibodies (see FIG. 5). Protein yields of 50-80% were commonly obtained for SPDP-thiolated antibodies such as 5E9 and 3A1 whereas yields of 20-50% were obtained for the same antibodies thiolated using 2-IT. Additionally, somewhat better immunoconjugate yields were obtained using monoclonal antibodies of the IgG1 isotype such as 5E9 and 3A1 for conjugations carried out with SPDP or 2-IT (see FIGS. 6 and 7).

The binding activity of the immunoconjugates of the invention was determined using a competition assay involving the use of $^{125}$I-labeled antibody. Respective antigen-positive and antigen-negative cells ($1 \times 10^6$) were suspended in 0.1 ml of RPMI 1640 containing 2% FBS and mixed with 0.1 ml of 2-fold serially diluted unconjugated monoclonal antibody or immunoconjugate at concentrations starting at 50 μg/ml. The cell suspensions, in duplicate, were incubated while mixing at 4° C. for 1 hour. The cells were then washed two times and suspended in 0.1 ml containing 5 μg/ml of $^{125}$I-labeled homologous antibody (specific activity from $1-50 \times 10^4$ cpm/μg antibody protein). Samples were incubated at 4° C. for 1 hour and overlaid onto 0.15 ml 1:1 mixture of dibutyl:dinonyl phthalate that was cooled to 4° C. The samples were centrifuged at 10,000×g for 1 min at 4° C. and the cell-bound counts (pellet) determined using an LKB gamma counter.

The retention of binding activity by the immunoconjugates of this invention is demonstrated in Table 1 below.

TABLE 1

Relative Binding Affinity Estimates After ADM-HZN Conjugation

| Inhibitor | Molar Ratio | Trace | $[I_t]^a \times 10^{-9}$ M | $[T_t]^b \times 10^{-9}$ M | $\simeq K_{conj}{}^c \times 10^7$ L/M |
|---|---|---|---|---|---|
| — | — | 5E9-$^{125}$I | — | — | 3.2 |
| — | — | 3A1-$^{125}$I | — | — | 5.1 |
| SPDP Linker | | | | | |
| 5E9-ADM | 3.5 | 5E9-$^{125}$I | 4.2 | 3.4 | 2.6 |
|  | 4.0 |  | 6.7 | 2.1 | 1.0 |
|  | 4.9 |  | 4.2 | 4.0 | 3.0 |
|  | 6.8 |  | 4.2 | 2.1 | 1.6 |
|  | 8.5 |  | 10.0 | 2.1 | 0.7 |
| 3A1-ADM | 2.6 | 3A1-$^{125}$I | 4.2 | 1.3 | 1.5 |
|  | 3.3 |  | 1.3 | 1.3 | 5.1 |
|  | 4.2 |  | 8.3 | 1.3 | 0.8 |
|  | 6.7 |  | 7.3 | 1.3 | 0.9 |
| 2-IT Linker | | | | | |
| 5E9-ADM | 5.6 | 5E9-$^{125}$I | 4.1 | 4.0 | 3.1 |
|  | 6.7 |  | 4.7 | 4.0 | 2.7 |
| 3A1-ADM | 6.0 | 3A1-$^{125}$I | 4.0 | 1.3 | 1.6 |

$^a[I_t]$ = Molar concentration of antibody conjugate giving 50% inhibition of tracer antibody.
$^b[T_t]$ = Molar concentration of antibody giving 50% inhibition of tracer antibody.
$^cK_{conj}$ = Relative (K) affinities were calculated using the formula:

$$K_{conj} = \frac{[T_t]K_{Ab}}{[I_t]}$$

$K_{Ab}$ is the equilibrium constant of the unconjugated MAb as determined by Scatchard analysis.

As shown in the table, the 5E9 immunoconjugates prepared using SPDP and having molar ratios ranging between 3.5 and 8.5 retained over 80% of their original binding activity as compared to unconjugated 5E9. 5E9 immunoconjugates prepared using 2-IT also retained high binding activities. 3A1 immunoconjugates prepared using SPDP showed some loss in antibody binding activity. In general, conjugation of ADM to these and other antibodies resulted in loss of relatively small degrees of antibody binding activity.

Figure 8A:
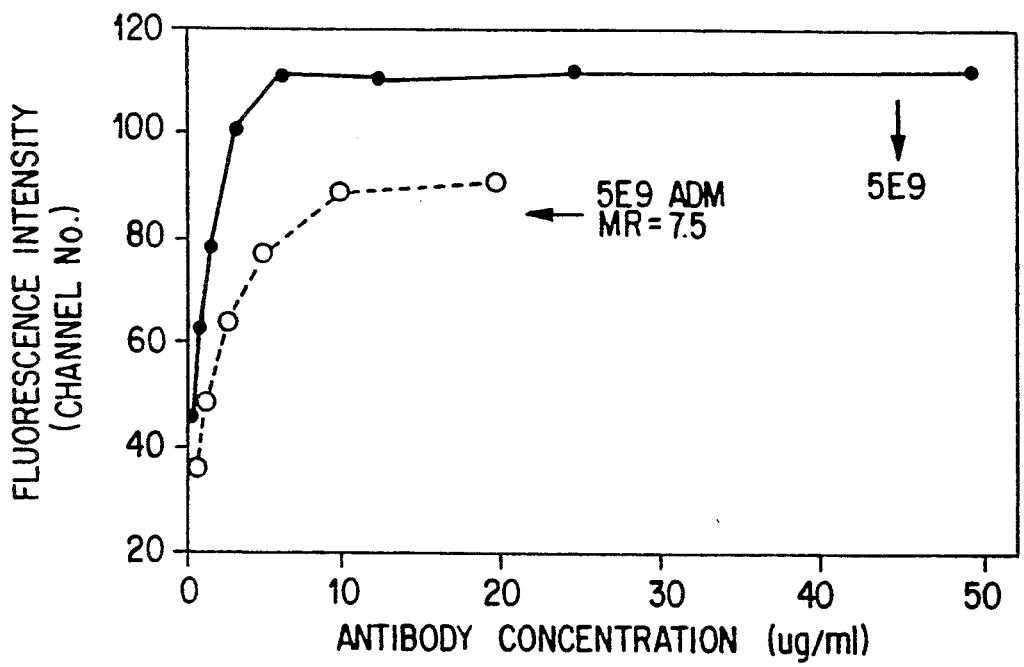
FIGS. 8A and 8B depict in graph form the binding curves of two immunoconjugates of the invention compared to the binding curves of the respective unconjugated monoclonal antibodies.
Figure 8B:
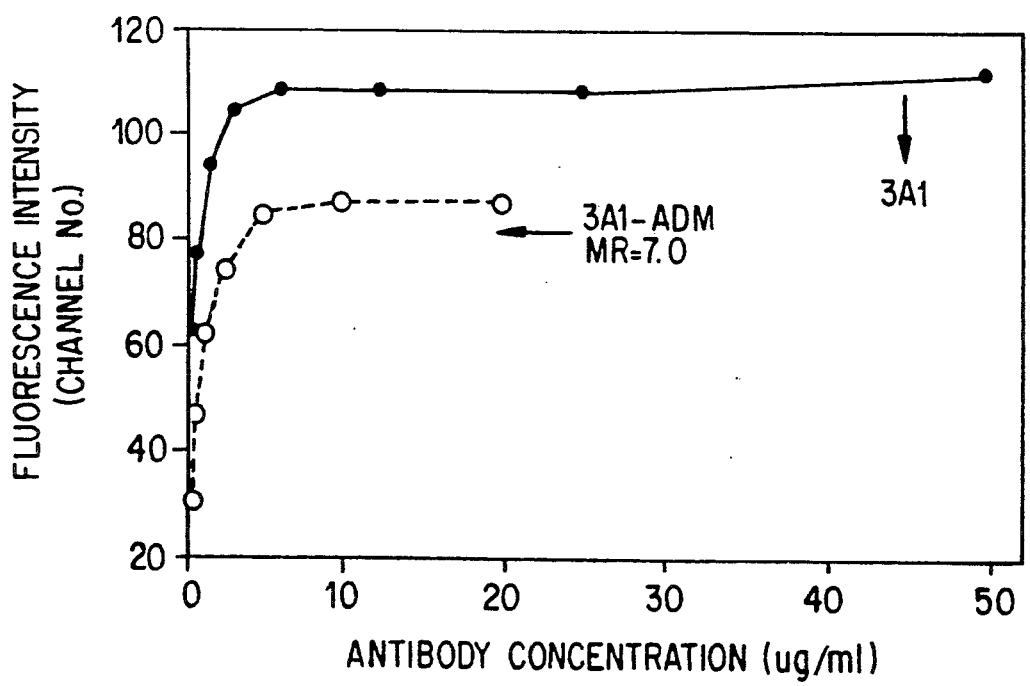

FIG. 8 shows the binding curves of two immunoconjugates of the invention, 5E9-ADM-7.5 and 3A1-ADM-7.0, compared to the binding curves of the unconjugated 5E9 and 3A1 monoclonal antibodies. To obtain these curves, the immunoconjugates were incubated at 4° C. in 0.1 ml complete growth medium containing $1 \times 10^6$ antigen-positive HSB-2 target cells. After 1 hour, the cells were washed twice in the medium and incubated for an additional 30 min in 0.1 ml of medium containing 1:40 dilution of FITC-labeled goat anti-mouse IgG (Boehringer-Mannheim). The cells were analyzed on a Coulter Epics V fluorescence cell analyzer. Cell surface fluorescence was compared to the fluorescence obtained using similarly diluted unconjugated monoclonal antibody. As the figure indicates, the binding activity of each of the immunoconjugates was preserved as demonstrated by the fact that the concentration of immunoconjugate that was required to saturate the antigen-positive cells was at most one doubling dilution greater than the concentration required for the unconjugated antibody. The differences in the plateau levels of fluorescence intensity between unconjugated antibodies and the immunoconjugates was found to be due to reduced binding of the secondary FITC-goat anti-mouse reagent to the immunoconjugate as compared to the unconjugated antibody.

The stability of an immunoconjugate of this embodiment—an L6-ADM conjugate—at various pH's, ranging from 4.0 to 7.0, was studied using HPLC analysis. The L6-ADM-9.0 conjugate was incubated in phosphate buffers at each of the indicated pHs for 24 hours at 37°. Each solution was then applied to an HPLC column and the amount of unconjugated drug was determined. As shown in FIG. 9, the single product detected after 24 hour incubation at the different pH's had a column retention time similar to that of the ADM-HCl standard. The amount of material released from the immunoconjugate after 24 hours increased as the pH was lowered from 7 to 4. The "untreated" control represents the chromatograph of the conjugate stored at $-20°$ in pH 7.4 phosphate buffer. It thus appears that the immunoconjugate has an acid-sensitive linkage group which resulted in the release of ADM from the antibody protein. These results are consistent with the existence of a hydrazone bond joining the ADM to the linker arm as described in FIG. 2.

Figure 10:
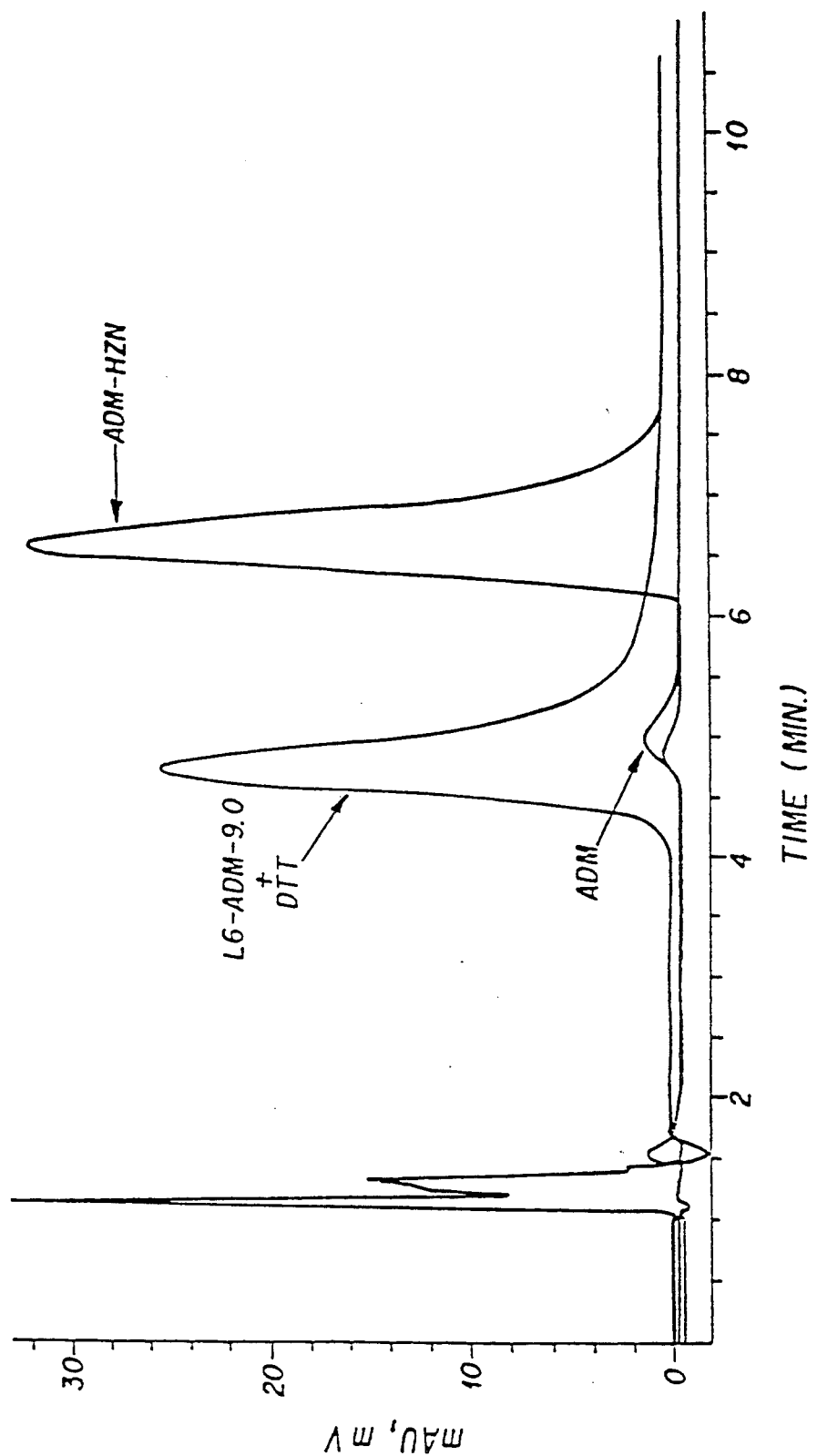
FIG. 10 is an HPLC chromatograph showing the release of an ADM moiety from an immunoconjugate of this invention after treatment with DTT.

According to the embodiment of this example, ADM was attached to the antibody through a linker arm that also contained a disulfide bond (see FIG. 2). It should thus be possible to release an ADM moiety by reduction of an immunoconjugate of this embodiment with DTT. Therefore, the L6-ADM conjugate, L6-ADM-9.0, was treated with a 10-fold excess DTT, incubated at room temperature for 15 min and applied to an HPLC column. ADM-HCl and ADM-HZN standards were run at the same time and the peaks from the chromatographs are indicated in FIG. 10. L6-ADM-9.0 had no detectable peak of unconjugated drug prior to the addition of DTT. HPLC analysis showed the appearance of a single peak that had a column retention time similar to that of ADM-HCl rather than the ADM-HZN derivative (see FIG. 10). The amount of ADM released after DTT treatment was approximately 99% of the starting ADM equivalents bound to the antibody. The experimental data of FIGS. 9 and 10 demonstrate that an ADM-like moiety is released from the immunoconjugates of this invention under "physiologic" conditions, i.e., acidic ant reducing conditions, typical of the cellular environment.

Cytotoxic Activity Of The Immunoconjugates Of The Invention

The immunoconjugates of the invention were tested in vitro for cytotoxicity using a number of assay systems. According to a soft agar colony formation assay, Daudi (Burkitt's lymphoma) cells (phenotype: 5E9+, 3A1−) obtained from the ATCC were grown in complete medium [RPMI 1640 medium plus 10% fetal calf serum]. $1 \times 10^5$ cells in 1 ml of medium were exposed for 1.5 hours to serially diluted 5E9-ADM or 3A1-ADM immunoconjugates or unconjugated ADM. Triplicate determinations were done for each dilution. Controls consisted of similarly treated cells not exposed to drugs. The cells were then washed and suspended in RPMI 1640 medium containing 15% FBS and 0.3% agarose (Marine Colloid). One ml of the cell suspension ($1 \times 10^3$ cells) was then overlayed onto a 0.4% agarose layer in 6-well microtiter plates (Costar). Samples were incubated for 7–10 days at 37° and the resulting colonies stained with 0.5 ml of 1 mg/ml of p-iodonitrotetrazolium violet (Sigma) for 48 hours. Colonies were counted using an Optimax 40-10 image analyzer and the inhibition of colony formation determined by comparing drug-treated or immunoconjugate-treated cells to the untreated control.

Figure 11:
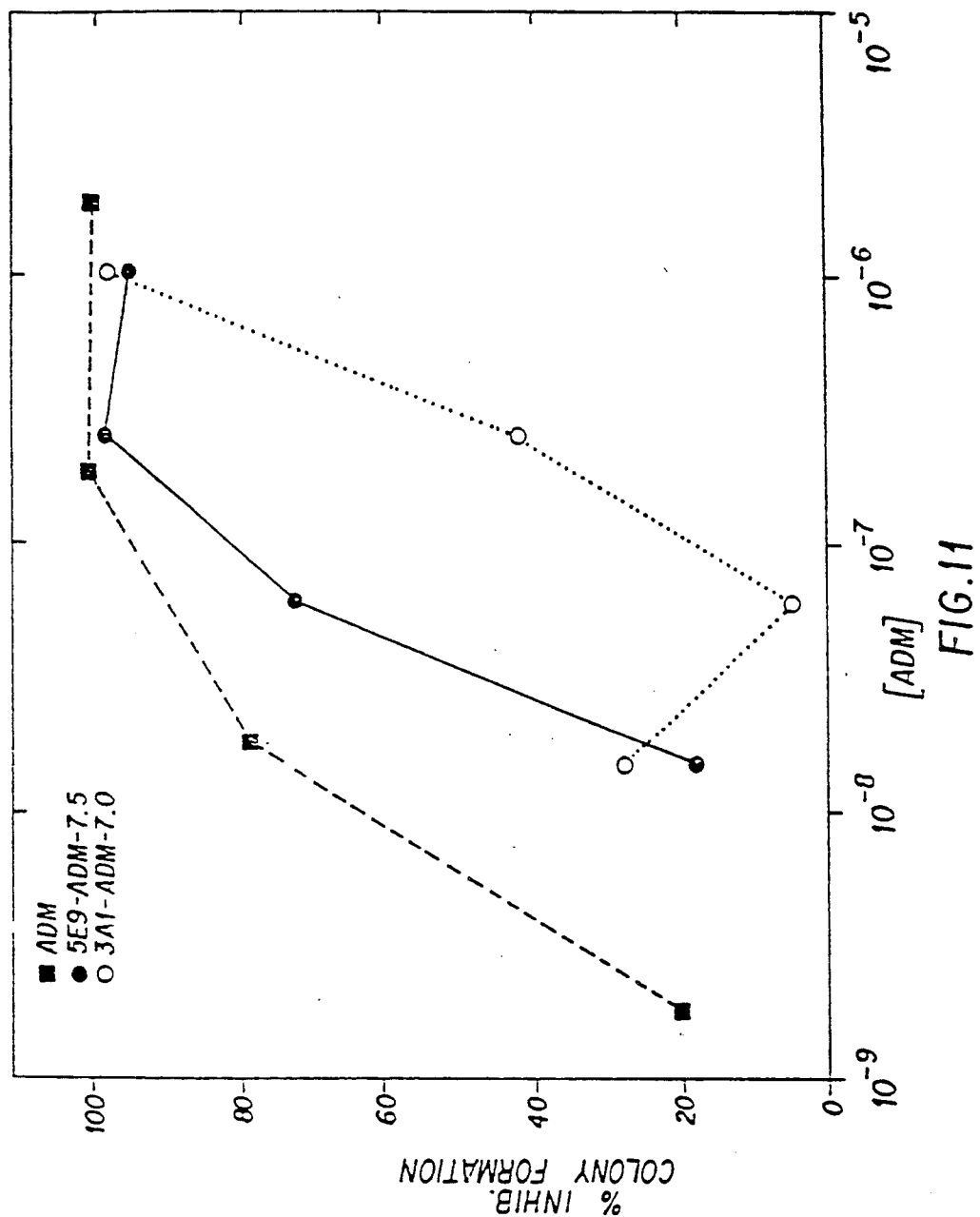
FIG. 11 depicts in graph form the selective cytotoxicity of immunoconjugates of this invention toward the Daudi cell line using a soft agar colony formation assay. These immunoconjugates had been prepared using 2-IT-thiolated antibodies.

FIG. 11 compares the cytotoxic activity of the 5E9-ADM conjugate, 5E9-ADM-7.5, and the 3A1-ADM conjugate, 3A1-ADM-7.0, after 1.5 hours exposure on the 5E9 antigen-positive and 3A1 antigen-negative Burkitt's lymphoma cell line, Daudi. Both of these immunoconjugates had been prepared via thiolation with 2-IT. Comparison of the dose response curves shows that the 5E9-ADM-7.5 conjugate which retained 93% of the original binding activity for antigen-bearing target cells (see FIG. 8) was significantly more potent than 3A1-ADM-7.0, the non-binding control conjugate.

A limiting dilution assay, which provides a measure of the log cell kill, was used to test for the cytotoxic drug activity of the above-mentioned two immunoconjugates, using a longer exposure format (24 hours). This assay was performed using Namalwa cells (phenotype: 5E9+, 3A1−) essentially as described by M. Colombatti et al., "Selective Killing Of Target Cells By Antibody-Ricin A Chain Or Antibody-Gelonin Hybrid Molecules: Comparison Of Cytotoxic Potency And Use In Immunoselection Procedures", *J. Immunol.*, 131, pp. 3091-95 (1983). The cells, obtained from the ATCC, were incubated with the immunoconjugates for 22 hours, washed and log cell kill was determined. Log cell kill was calculated based on the plating efficiencies that were estimated by the portion of wells without growth at limiting cell concentrations.

Figure 12:
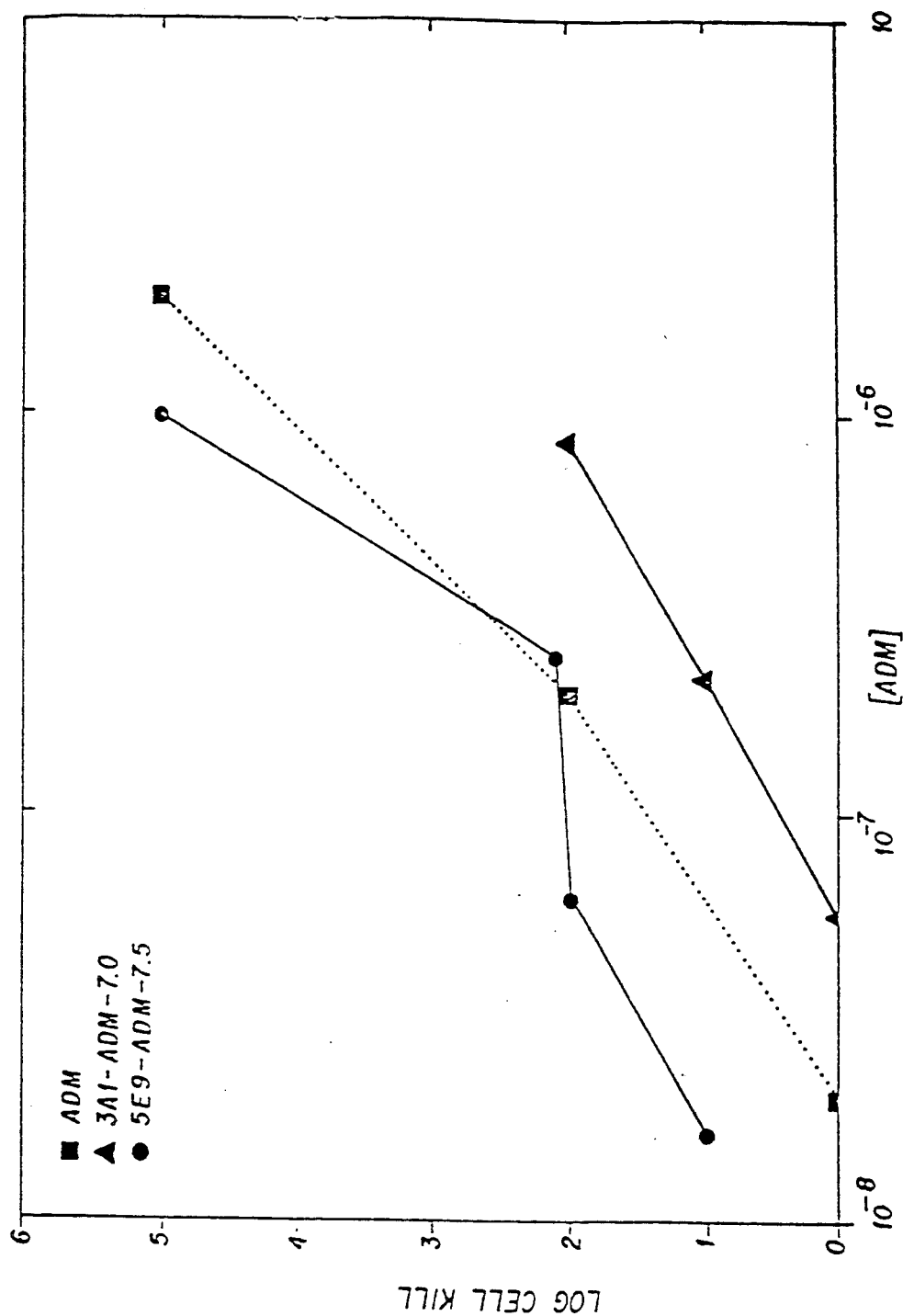
FIG. 12 depicts in graph form the selective cytotoxicity of immunoconjugates of this invention toward Namalwa cells and the increased potency of the immunoconjugates compared to free ADM, using a limiting dilution assay.

As shown in FIG. 12, 5E9-ADM-7.5 produced 1-2 logs greater cell kill at concentrations tested as compared with the non-binding 3A1-ADM-7.0 conjugate. Up to 5 logs of cell kill was measured at the highest dose of 5E9-ADM-7.5. Additionally, while cytotoxic activity for the non-binding 3A1 immunoconjugate was detected, the level of cytotoxicity was less than an equivalent amount of unconjugated ADM. However, the activity of the 5E9 immunoconjugate was, at several concentrations, greater than an equivalent dose of free ADM.

Figure 13:
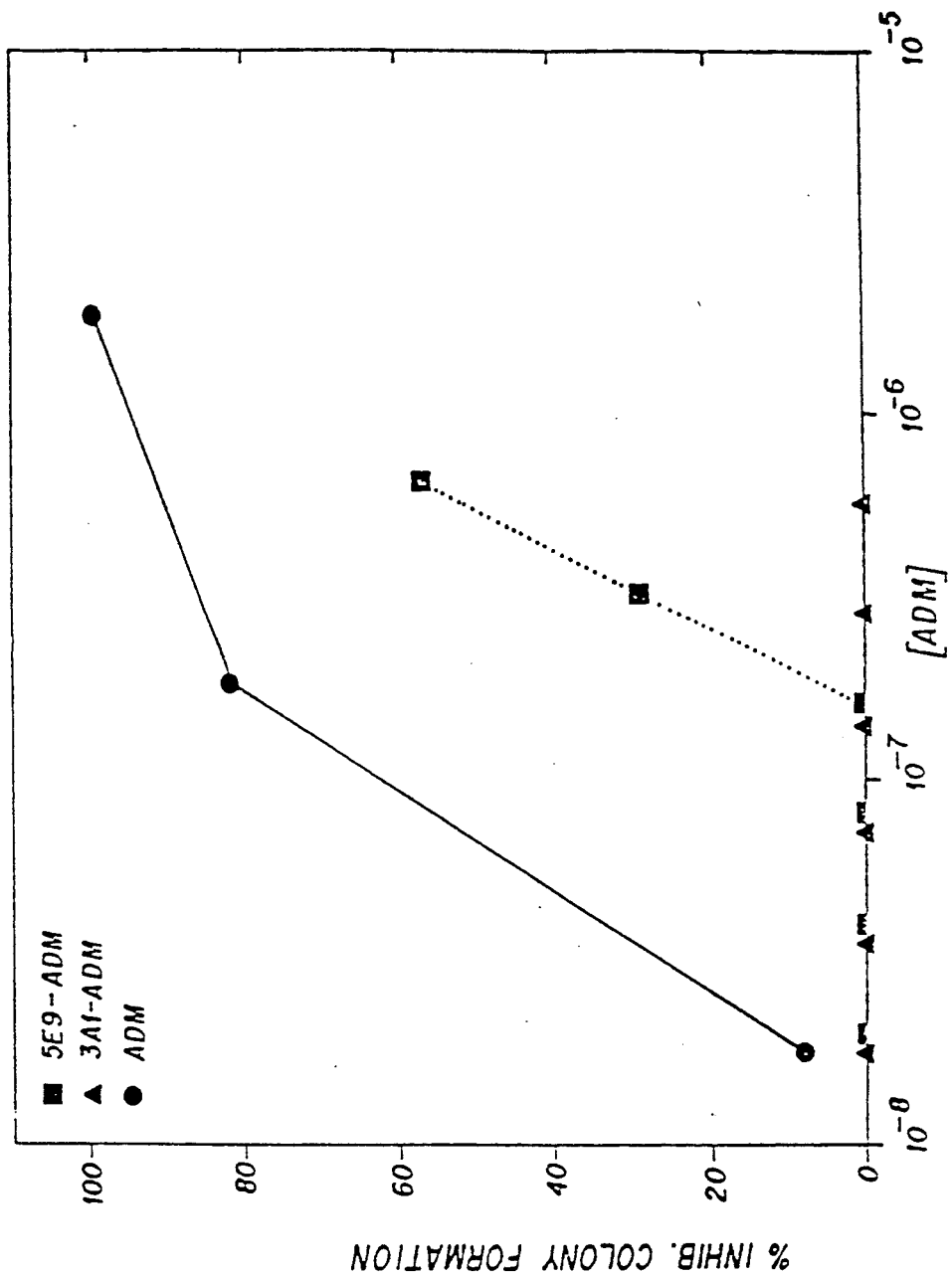
FIG. 13 depicts in graph form the selective cytotoxicity of immunoconjugates of the invention toward Daudi cells using a soft agar colony formation assay. In this instance, the immunoconjugates had been prepared using SPDP-thiolated antibodies.
Figure 14:
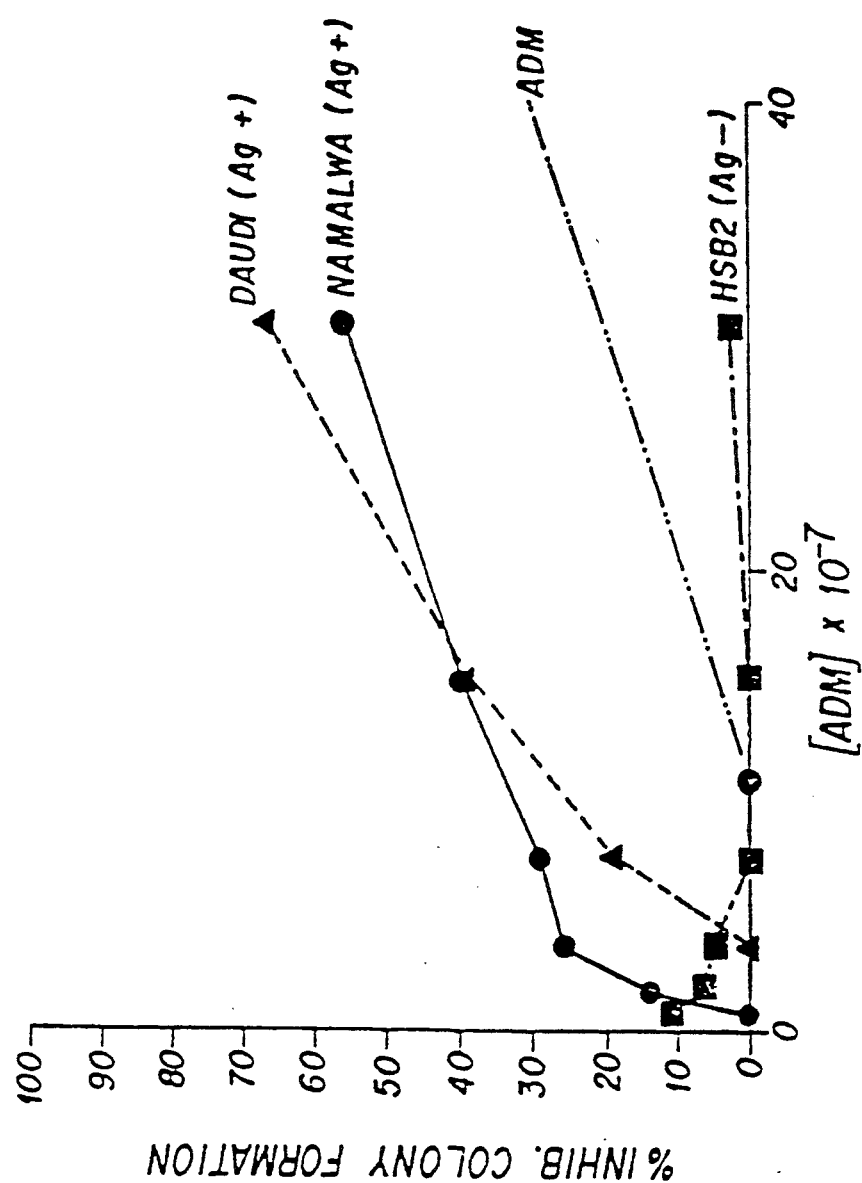
FIG. 14 depicts in graph form the selective cytotoxicity of another immunoconjugate of this invention prepared with SPDP as the thiolating agent. This immunoconjugate was cytotoxic toward antigen-positive Daudi and Namalwa cells, but not antigen-negative HSB-2 cells, using the soft agar colony formation assay.

As stated above, the 5E9-ADM-7.5 and 3A1-ADM-7.0 immunoconjugates were synthesized using 2-IT as the thiolating agent. Immunospecific cytotoxicity was also observed with immunoconjugates that were prepared using SPDP as the thiolating agent. FIG. 13 shows selective cytotoxic activity of 5E9-ADM and 3A1-ADM immunoconjugates, made using SPDP as the thiolating agent, on Daudi cells using the soft agar colony formation assay described above. Further evidence for selective cytotoxicity of immunoconjugates prepared using SPDP is shown in FIG. 14, where the G28.1-ADM-9.0 immunoconjugate was tested on two G28.1 antigen-positive cell lines, Daudi and Namalwa, and on one G28.1 antigen-negative human T cell leukemia cell line, HSB-2, using the soft agar colony formation assay. The HSB-2 cells were obtained from the ATCC. As shown in the figure, the immunoconjugate was cytotoxic toward the two antigen-positive cell lines but not toward the antigen-negative cell line.

Preferential killing of antigen-positive cells by the immunoconjugate, 5E9-ADM-7.5, was also observed in a colony formation assay using the anchorage-dependent human colon carcinoma cell line, HCT116, obtained as a gift from Dr. M. Brattain [Bristol-Baylor Labs, Houston, Tex.].

Figure 15:
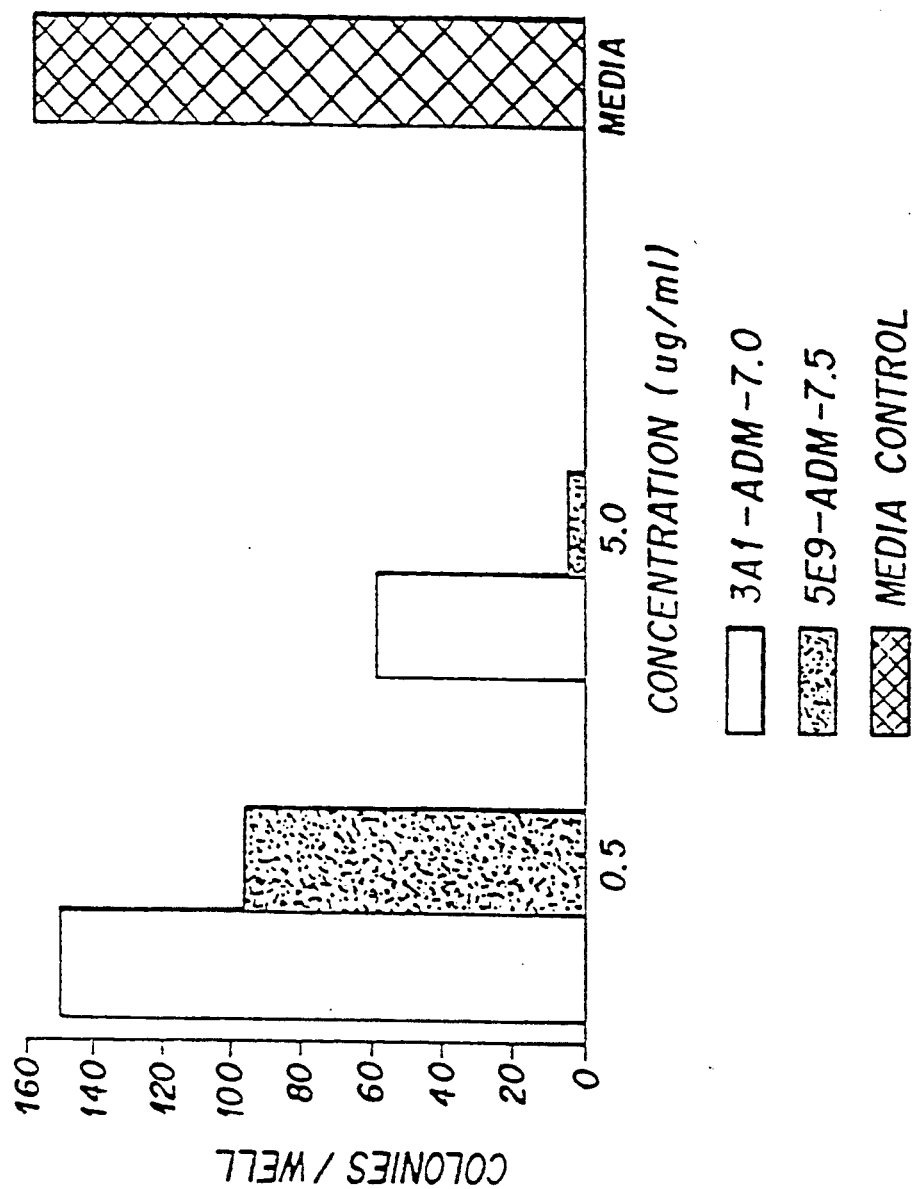
FIG. 15 depicts the selective cytotoxicity of 5Eg and 3A1 immunoconjugates of this invention toward a human colon carcinoma cell line (5E9+, 3A1−), using a colony formation assay.

Monolayer cultures of the carcinoma cells were removed from culture flasks with trypsin-EDTA (GIBCO), washed and passed through a 22-gauge needle to obtain a single cell suspension. 5E9-ADM-7.5, 3A1-ADM-7.0 or unconjugated ADM was serially diluted in 0.2 ml of medium containing $1 \times 10^5$ carcinoma cells. Each dilution was done in triplicate. Controls included untreated or antibody-treated cells. Cells were incubated for 3 hours, washed one time in medium and $1 \times 10$ cells in one ml were plated in 12-well microtiter plates (Costar). Plates were incubated for 7-10 days at 37° and fixed with absolute methanol for ten min. The colonies were stained with crystal violet and counted on an Optimax 40-10 image analyzer. As shown in FIG. 15, greater cytotoxicity was observed when the carcinoma cells were exposed to 5E9-ADM-7.5 than when they were exposed to 3A1-ADM-7.0.

Figure 16:
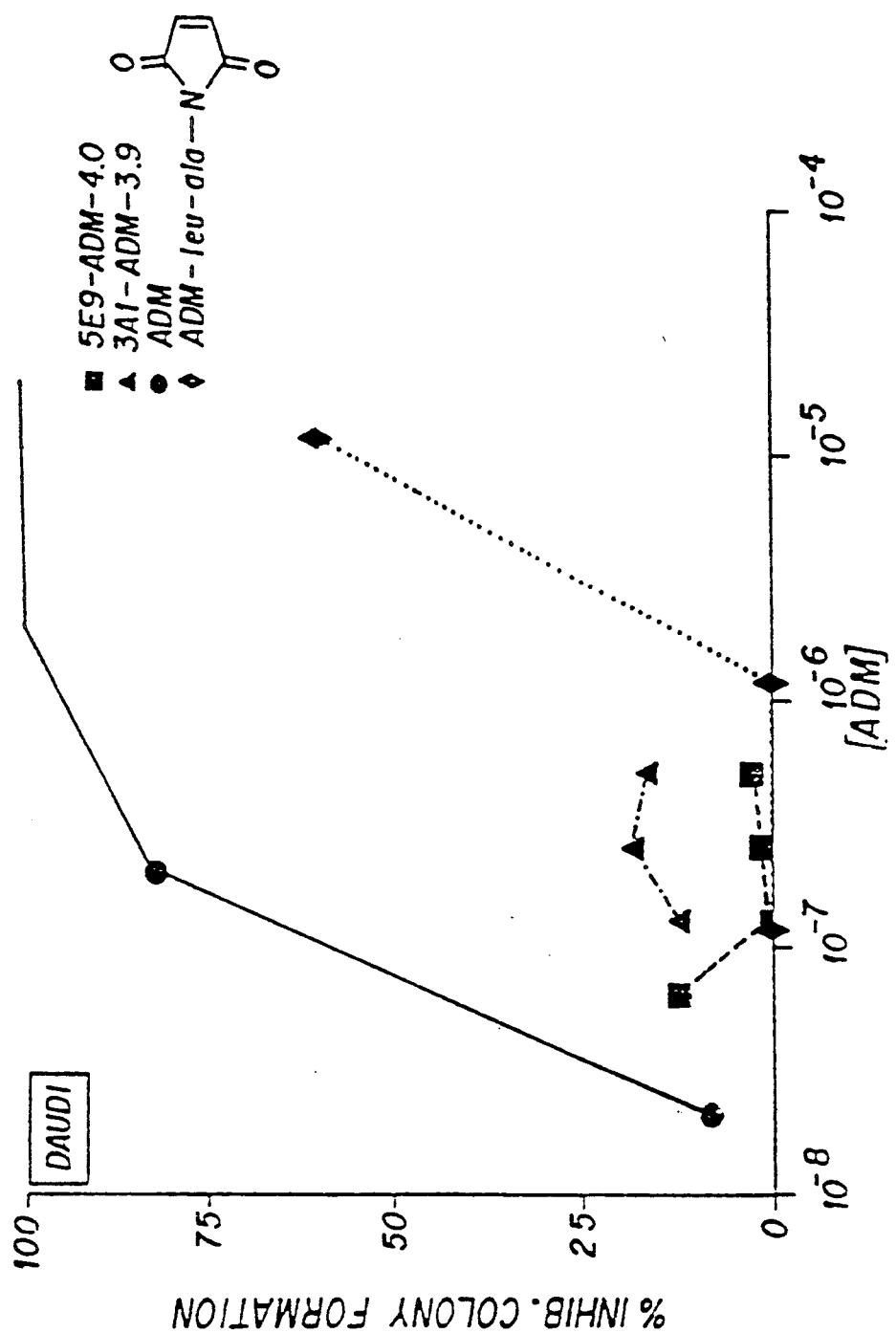
FIG. 16 depicts in graph form the lack of cytotoxicity towards Daudi cells of immunoconjugates prepared by attaching ADM to monoclonal antibodies at the amino sugar residue of the ADM through a leu-ala dipeptide linker.

Because many reports have shown that ADM linked to antibody at the amino sugar of the drug resulted in immunoconjugates showing a significant loss of drug activity, we tested the cytotoxicity of immunoconjugates prepared by attaching ADM to the antibody at the amino sugar of the drug thru a leu-ala dipeptide linker, using our soft agar colony formation assay system. As shown in FIG. 16, neither the 5E9-ADM-4.0 nor 3A1-ADM-3.9 peptide-linked conjugates were cytotoxic on Daudi cells. The ADM-leu-ala derivative used to make conjugates was about 2 logs less potent than equivalent amounts of unconjugated ADM.

EXAMPLE 2

This example describes the preparation of an anthracycline immunoconjugate according to the present invention wherein ADM is conjugated to a monoclonal antibody via a linker arm having an acylhydrazone bond as its site of attachment to the ADM molecule and additionally having a thioether linkage as part of its attachment to the antibody. This embodiment also provides a novel acylhydrazide derivative of ADM.

Preparation Of Immunoconjugates Having A Thioether Bond Within The Linker Arm

Monoclonal antibody, 5E9, (2.5 mg in 2.5 ml phosphate buffered saline) was reacted with SMPB (succinimidyl-4-(p-maleimidophenyl)butyrate) (59.5 µg in 100 µl tetrahydrofuran) at 30° for 30 min. The pH was adjusted to 6.0 with sodium citrate buffer. The mixture was passed through a PD-10 gel filtration column (Pharmacia) to separate maleimide-containing antibody from unreacted materials. The ADM-HZN derivative (1 mg) prepared as described in Example 1 was then dissolved in 1 ml MeOH/H$_2$O (9:1) and 0.5 µmoles of the ADM-HEN was reacted with 0.5 µmoles of tri-n-butylphosphine in 4:1 acetone:H$_2$O to prepare a novel reduced ADM-HZN (see FIG. 17). After 10 min, 0.1M sulfur in toluene was added to destroy remaining phosphine. The reduced ADM-HZN was then mixed with the 5E9 maleimide-containing antibody. Immunoconjugates so produced were purified by passage through a PD-10 gel filtration column. In some instances, when removal of toluene solvent had not been complete, an organic solvent layer separated, floating some protein from the reaction mixture. A gentle stream of air was used to remove the solvent and the denatured protein was removed by spinning of the mixture for 2 min at 16,000×g. The clear supernatant containing the immunoconjugates was then gel filtered and analyzed in PBS at pH 7.4. The ADM/antibody molar ratio was determined spectrophotometrically using OD$_{280}$ and OD$_{495}$ as described in Example 1. A typical reaction yielded immunoconjugates with molar ratios of between 3 and 4.

Cytotoxic Activity Of Immunoconjugates Having A Thioether Linkage

A number of immunoconjugates prepared according to the embodiment of this example were tested for cytotoxicity toward antigen-positive vs. antigen-negative tumor cell lines using a $^3$H-thymidine incorporation assay which measures inhibition of DNA synthesis. According to this assay, dilutions of the immunoconjugates or unconjugated ADM were made in complete medium and 100 μl of each dilution was added to wells in 96-well microtiter plates. Each dilution was done in triplicate. Tumor cells were suspended in medium and 100 μl containing $1 \times 10^5$ cells were then added to each well. Cells were incubated for 24 hours at 37° C. in a 5% $CO_2$ humid atmosphere. Fifty microliters containing 1 μCi[6-$^3$H]-thymidine (New England Nuclear, 15 Ci/mmole) was added to each well and incubated for four hours at 37° C. Cells were transferred to Millititer sv plates (Millipore) and precipitated with 25% cold trichloroacetic acid (TCA). The precipitates were washed ten times with 5% cold TCA. Filters were dried, punched and counted in Eronofluor liquid scintillation fluid (New England Nuclear). All counts were corrected by subtraction of background counts.

Figure 18:
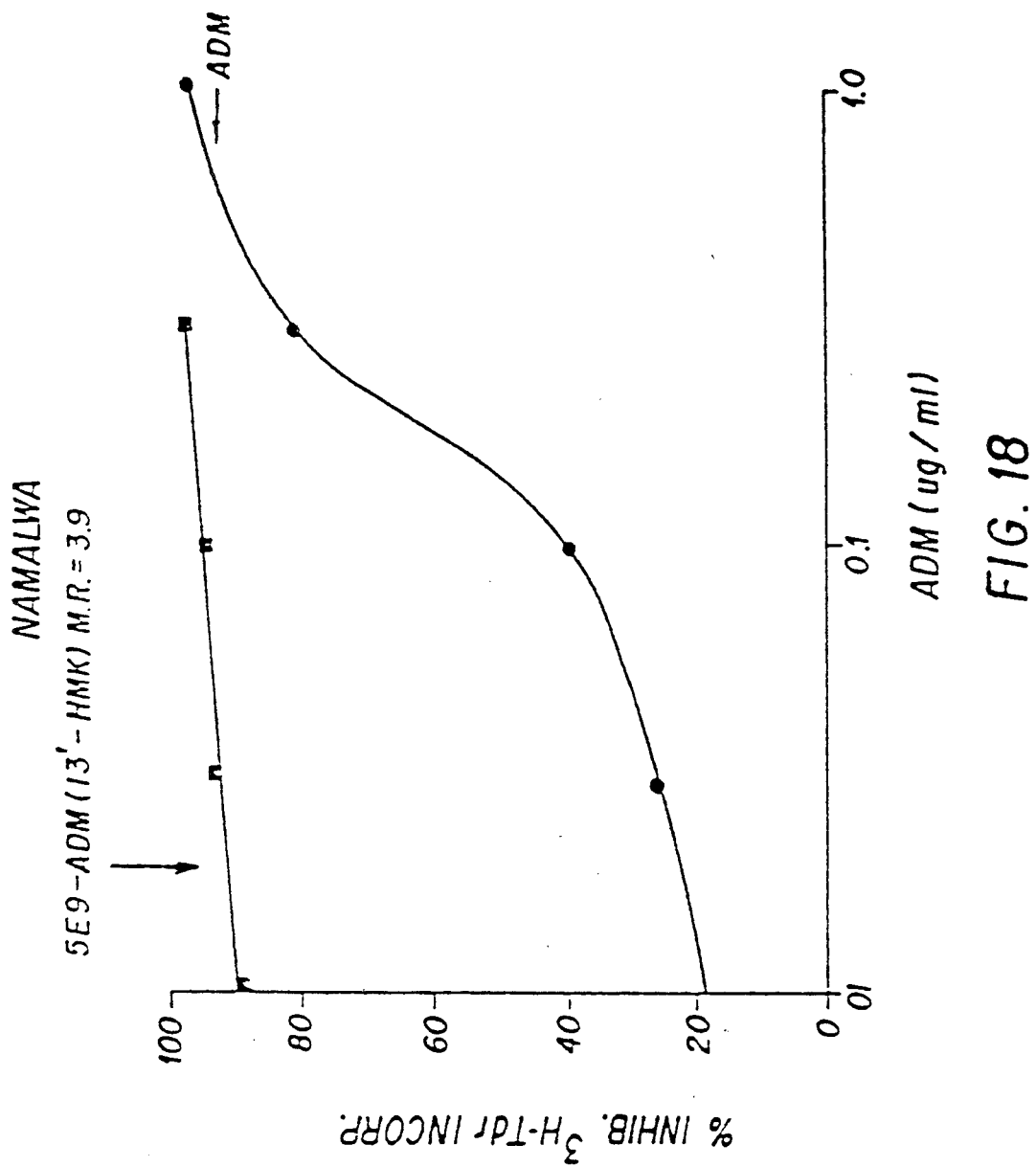
FIG. 18 depicts in graph form the cytotoxicity of an immunoconjugate of the invention having, additional to the 13-keto acylhydrazone linkage, a thioether bond within its linker arm. The immunoconjugate showed greater potency relative to free ADM toward Namalwa cells, using a $^3$H-thymidine incorporation assay.
Figure 19:
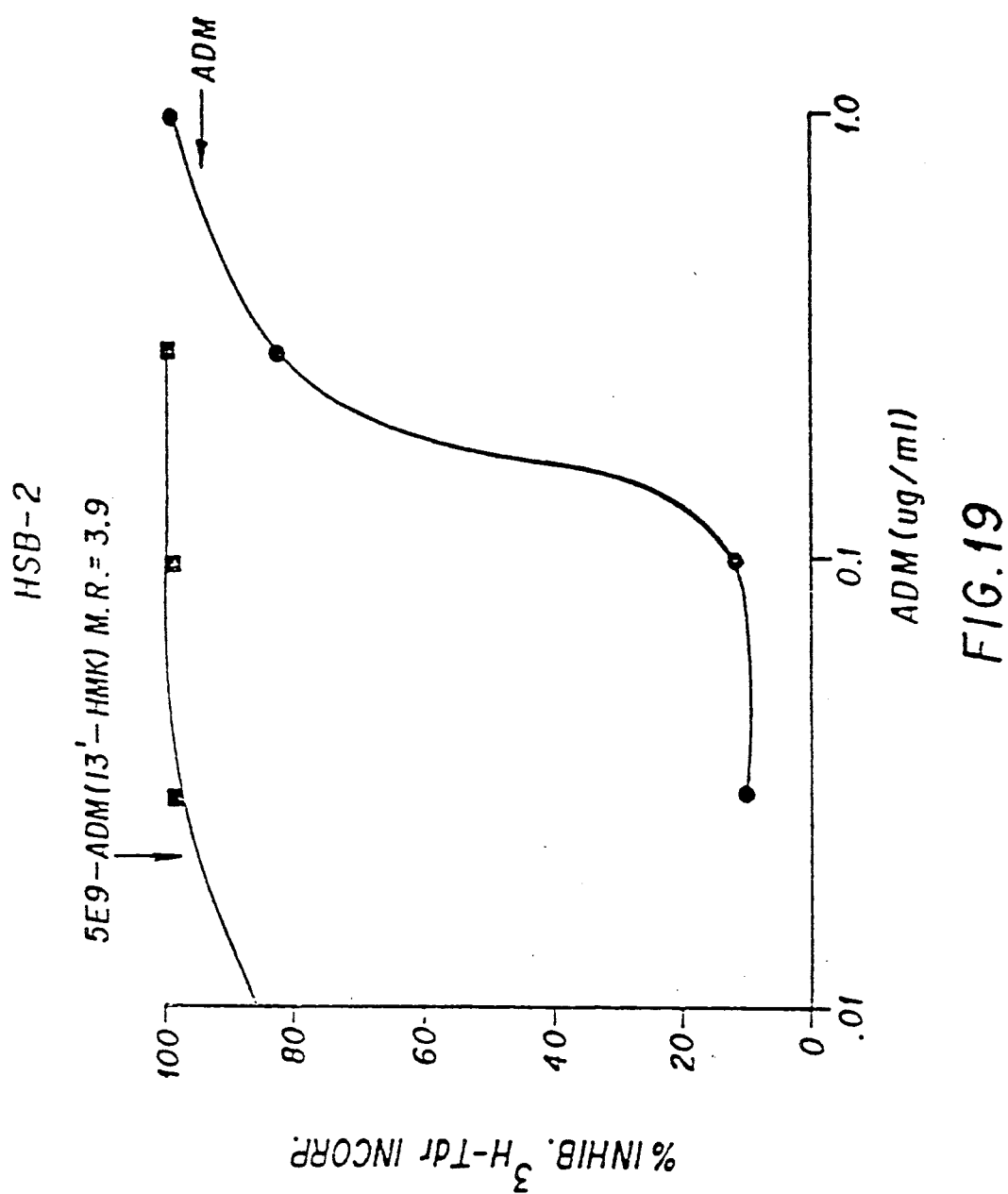
FIG. 19 depicts in graph form the cytotoxicity toward HSB-2 cells of the immunoconjugate of FIG. 18, using the same $^3$H-thymidine incorporation assay.
Figure 20:
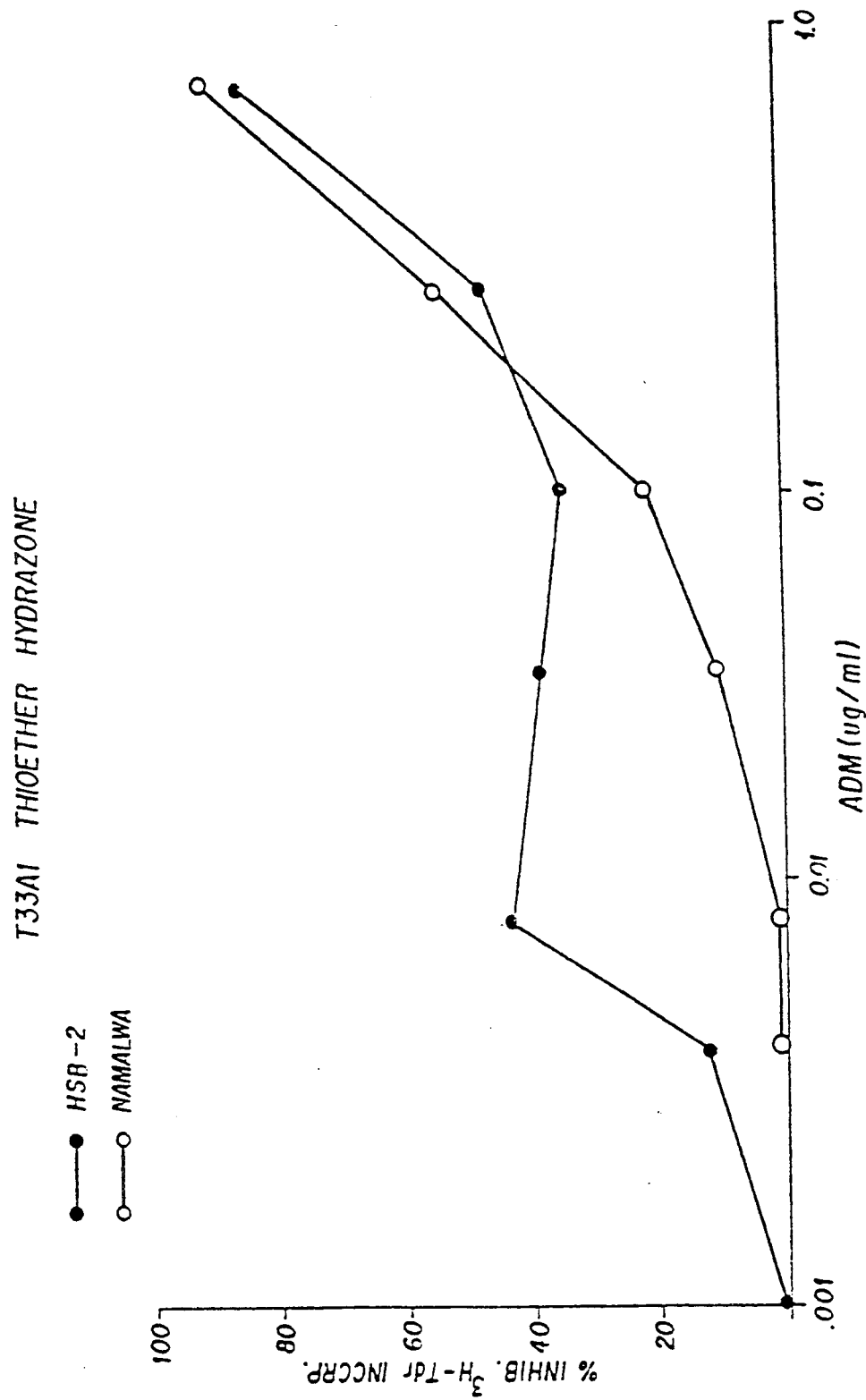
FIG. 20 depicts in graph form the selective cytotoxicity of an immunoconjugate of the invention toward antigen-positive cells vs. antigen-negative cells using the $^3$H-thymidine incorporation assay, the immunoconjugate having, additional to the 13-keto acylhydrazone linkage, a thioether bond within its linker arm.

An immunoconjugate according to this embodiment—5E9-ADM-3.9—was highly cytotoxic toward 5E9 antigen-positive Namalwa and HSB-2 cells (see FIG. 18). The immunoconjugate was more potent than equivalent concentrations of unconjugated ADM. In another experiment, a 3A1-ADM-6.0 immunoconjugate at concentrations below 0.1 μg/ml ADM was found to be cytotoxic toward 3A1-antigen-positive HSB-2 cells but not toward 3A1-antigen-negative Namalwa cells (see FIG. 20). At higher concentrations, the cytotoxicity of the immunoconjugate was about the same toward both cell lines.

EXAMPLE 3

In Vivo Anti-Tumor Activity Of The Immunoconjugates Of The Invention

Immunoconjugates of the invention were next tested for their anti-tumor activity in vivo. More particularly, the immunoconjugates were tested for their ability to inhibit the growth of human B lymphoma tumors in mice.

Primary Daudi and Ramos (Burkitt's lymphoma) solid tumors were established in BALB/c nude mice by subcutaneous (s.c.) inoculation of tissue culture-maintained lymphoid cells. The Ramos cell line is available from the ATCC. The Daudi and Ramos tumors were then serially passaged in vivo in 4-6 week old female BALB/c (nu/nu) mice weighing from 20-25 gm (Harlan Sprague-Dawley), using $1 \times 10^7$ tumor cells/0.1 ml in PBS for implantation subcutaneously into the flank of the mice. Both tumor lines showed a linear growth rate between 200 and 4000 mm$^3$. The median tumor volume doubling time during exponential growth was 6.9±0.8 days for Daudi tumors and 4.4±0.6 days for Ramos tumors. Tumor volumes (V) were calculated using the formula:

$$V = \frac{L \times W^2}{2}$$

where L=length (mm) and W=width (mm).

When tumor volumes reached 400-600 mm$^3$ for Daudi tumors and 250-400 mm$^3$ for Ramos tumors, the mice were randomized into groups of 5-10 animals for treatment with ADM-HCl (i.e., free drug), ADM-immunoconjugates of the invention, unconjugated monoclonal antibody or a mixture of the monoclonal antibody plus ADM. Specificity of cell killing was demonstrated by comparing the anti-tumor activity obtained with the tested immunoconjugates (i.e., whose antibody component is reactive with the tumor cells to be killed) vs. that obtained using non-binding conjugates (i.e., conjugates that are not reactive with that tumor population). The mixture of antibody plus free drug was a control demonstrating the need for a covalent coupling of drug to antibody.

Results were expressed as inhibition of tumor growth (T-C) or tumor doubling delay (TDD) which were estimated from the delay in the tumor volume doubling time (TVDT) when growth curves from treated groups were compared to uninoculated controls. TDD was calculated using the formula $$TDD = \frac{T - C}{TVDT \times 3.3}$$

where T=time (days for the tumors in a treated group to reach 3000 mm$^3$, C=time (days) for tumors in a control group to reach 3000 mm$^3$, and TVDT (tumor volume doubling time)=time (days) for the tumor volume in control (non-treated) mice to increase from 1500-3000 mm$^3$. Each point represents the median tumor volume in the experimental group.

In these studies, the anti-tumor activity of the ADM-immunoconjugates on Daudi or Ramos tumors was compared to: a) that obtained using free drug at an equivalent dose, route of administration, and schedule and b) the activity obtained using the free drug given at its optimal dose, route and schedule.

In all of the studies described herein, drug treatment with ADM-HCl was performed by adding 50-100λ DMSO to the powdered drug, diluting the dissolved drug in PBS to a particular dosage of mg/kg/inj on the day of injection and inoculating it into the tumor-bearing mice either intravenously (i.v., tail vein) or intraperitoneally (i.p.). The ADM-immunoconjugates used in these studies were prepared as described in Example 1 and all retained greater than 90% of the original antibody binding activity. Specifically, the monoclonal antibodies 5E9 and G28.1 were used as the antibody component of the immunoconjugates in these studies. The ADM-immunoconjugates were stored at 4° C. in PBS and used no later than two weeks after their preparation. All of the immunoconjugates tested as well as unconjugated antibody controls were administered i.p.

Furthermore, as used in this application, the treatment schedule notation "Q7Dx3" connotes a treatment schedule wherein each mouse in that drug group was given 3 injections, each injection spaced 7 days apart, i.e., an injection weekly for three weeks. Likewise, "Q5Dx2" refers to a treatment schedule wherein the mice in that group were given a total of 2 injections of drug or conjugate spaced 5 days apart. Q1Dx1 refers to a single injection. Thus, the treatment schedule notations are defined wherein the first numeral of the notation represents the spacing (in days) of injections and the last numeral represents the total number of injections per schedule.

The anti-tumor activity of the ADM-immunoconjugates of the invention was therefore first evaluated as compared to the free ADM-HCl drug at a matching or equivalent dose, route of administration, and schedule. The anti-tumor activity on Daudi tumors of a 5E9-ADM immunoconjugate, 5E9-ADM-1.8 (mole ratio=MR=1.8 ADM molecules/MAB), was compared to the activity of a) unconjugated ADM-HCl at a matching drug dose (4.1 mg/kg/inj), b) the 5E9 monoclonal antibody at a matching antibody dose (630 mg/kg/inj), c) a mixture of the 5E9 antibody plus ADM-HCl (4.1 mg ADM+630 mg 5E9), and d) a non-binding immunoconjugate, L6-ADM-8.6 (4.1 mg/kg/inj ADM) as a control.

Mice (5 mice/group) were dosed, i.p., on days 20 and 25 after tumor implantation (i.e., a Q5Dx2 schedule) when initial tumor sizes ranged from between 800 to 1100 mm$^3$. The dose used in this experiment represented the maximum tolerated dose (MTD), i.p., for free drug, that is, the dose of the drug administered via any given route or schedule that results in an LD$_{10}$ (death of 10% of the animals) (see Table 1 below).

Figure 21:
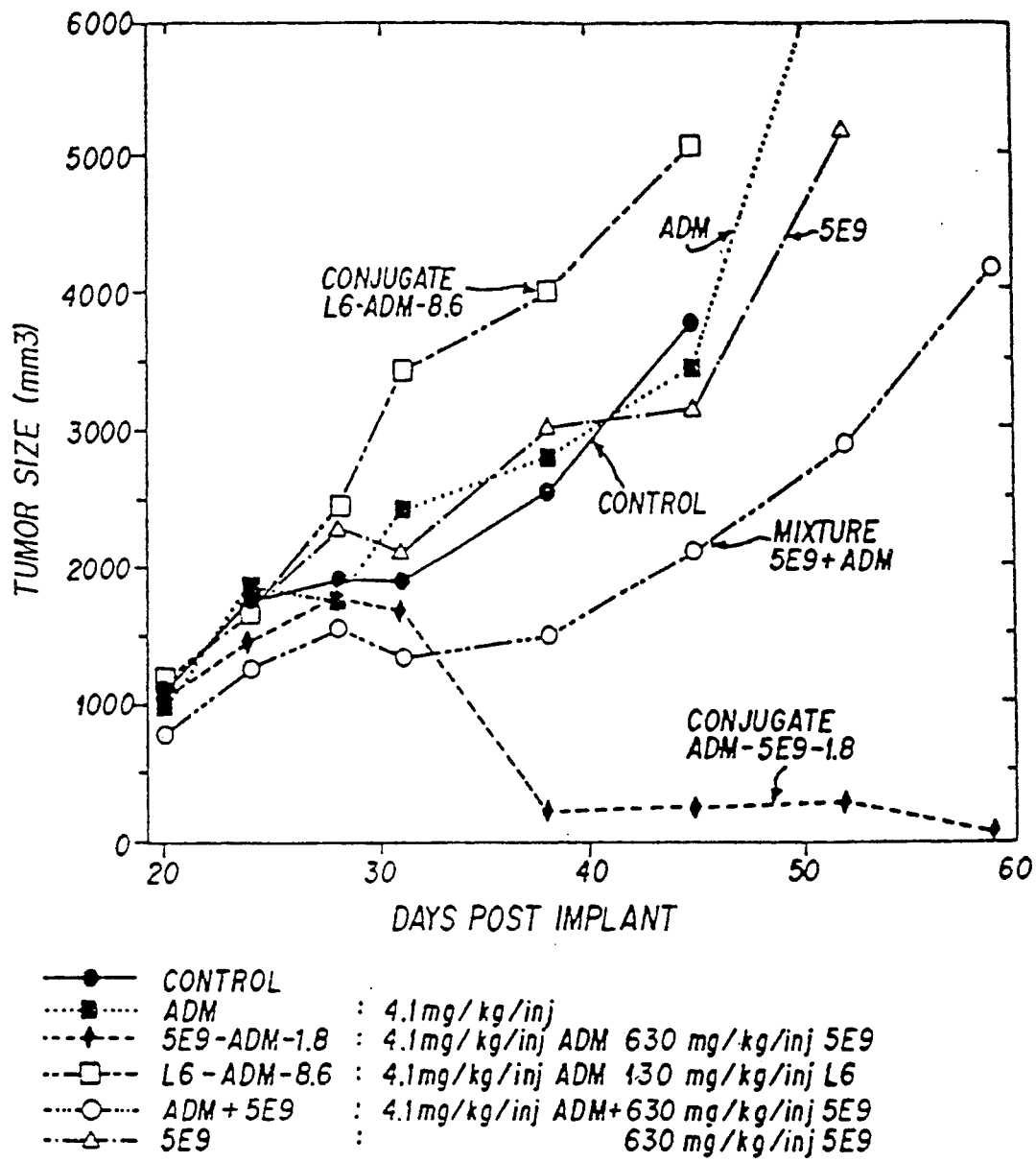
FIG. 21 depicts in graph form the in vivo anti-tumor activity of an immunoconjugate of the invention on human Daudi tumor xenografts in mice. The immunoconjugate showed a greater anti-tumor activity than that seen using an equivalent dose of free ADM.

As FIG. 21 indicates, significant anti-tumor activity was obtained with the 5Eg-ADM conjugate. Furthermore, this anti-tumor activity was greater than that observed at an equivalent dose of free drug. And, as plus monoclonal antibody were inactive. However, as FIG. 21 makes clear, even at this low dose, the ADM immunoconjugate was still active in inhibiting tumor growth.

Next, we sought to determine the anti-tumor activity of the ADM-immunoconjugates on Daudi tumors as compared to the anti-tumor activity obtained using the unconjugated drug given at its optimal dose, route of administration, and schedule. Initially therefore, we had to determine the dose, route, and schedule of free ADM-HCl that led to a maximal anti-tumor activity on Daudi cells. For this optimization study, mice were treated with ADM-HCl using different routes of administration, dosages and schedules. The spacing of inoculations was dependent on the treatment schedule employed. TDD values were then determined as described above.

The results of this optimization study are summarized in Table 2 below. As can be seen from Table 2, the Q7Dx3 schedule, given i.v., gave an optimal anti-tumor response, both in terms of tumor growth delay and in tumor regression rates at a dose of 11 mg/kg/inj, which was also the MTD for the drug using the Q7Dx3 schedule, i.v.

TABLE 2

| | Anti-Tumor Activity Of ADM-HCl on Daudi Tumor Xenografts | | | | | | | |
|---|---|---|---|---|---|---|---|---|
| | Dose (mg/kg)$^a$ | | Tumor Inhibition$^b$ | | | | Toxicity$^c$ | |
| Schedule | inj | cum | T-C | CR | Cures | TDD | D/T | (%) |
| A) i.v. Route | | | | | | | | |
| Q1D × 1 | 20 | 20 | — | — | — | — | 7/7 | (100) |
| | 18 | 18 | — | — | — | — | 6/8 | (75) |
| | 15 | 15 | — | — | — | — | 7/7 | (100) |
| | 12 | 12 | — | — | — | — | 7/7 | (100) |
| Q7D × 3 | 12 | 36 | >62 | 1 | 3 | >2.0 | 4/8 | (50) |
| | 11 | 33 | 28 | 0 | 3 | 1.1 | 2/8 | (25) |
| | 11 | 33 | >42 | 0 | 4 | >1.3 | 2/10 | (20) |
| | 11 | 33 | 21 | 1 | 0 | 0.7 | 0/8 | |
| | 10 | 30 | 18 | 0 | 1 | 0.7 | 0/8 | |
| | 10 | 30 | 13 | 0 | 1 | 0.8 | 0/8 | |
| | 10 | 30 | 27 | 0 | 3 | 0.8 | 0/7 | |
| | 9 | 27 | 23 | 0 | 1 | 0.9 | 0/10 | |
| | 5 | 15 | 6.2 | 2 | 0 | 0.18 | 1/9 | (11) |
| B) i.p. Route | | | | | | | | |
| Q5D × 2 | 4.5 | 9 | | 0 | 0 | 0 | 0/5 | |
| | 4.1 | 8.2 | 0 | 0 | 0 | 0 | 1/5 | |
| | 4.5 | 9 | 2.2 | 0 | 0 | .1 | 0/8 | |
| | 5.5 | 11 | 2.2 | 0 | 0 | .1 | 0/8 | |
| Q8D × 2 | 13 | 26 | — | — | — | — | 7/7 | (100) |
| | 10 | 20 | — | — | — | — | 8/8 | |
| | 5 | 10 | — | — | — | — | 3/8 | (37) |
| Q4D × 3 | 5 | 15 | — | — | — | — | 6/9 | (67) |
| Q7D × 3 | 10 | 30 | — | — | — | — | 8/8 | (100) |
| | 5 | 15 | — | — | — | — | 6/9 | (67) |

$^a$Results from individual drug groups.
$^b$T-C: represents the time delay in days for the drug-treated group (T) to reach 3000 mm$^3$ as compared to untreated controls (C).
Complete Regressions (CR): temporary reduction in tumor volume below palpable tumor size.
Cures: complete regression with no evidence of tumor regrowth.
$^c$D/T: number of deaths over total number of animals within a group. Drug deaths were recorded up to 55 days after the last drug dose.

Table 4 below indicates, three of the five mice treated with the conjugate had complete tumor regressions (cures), which corresponded to a >1.5 TDD. In contrast, ADM-HCl and unconjugated 5E9 as well as the L6-ADM non-binding conjugate exhibited no anti-tumor activity. Some tumor growth inhibition was observed using the ADM-HCl plus 5E9 mixture, but this effect was transitory and represented only a statistically insignificant 0.2 TDD.

Figure 22:
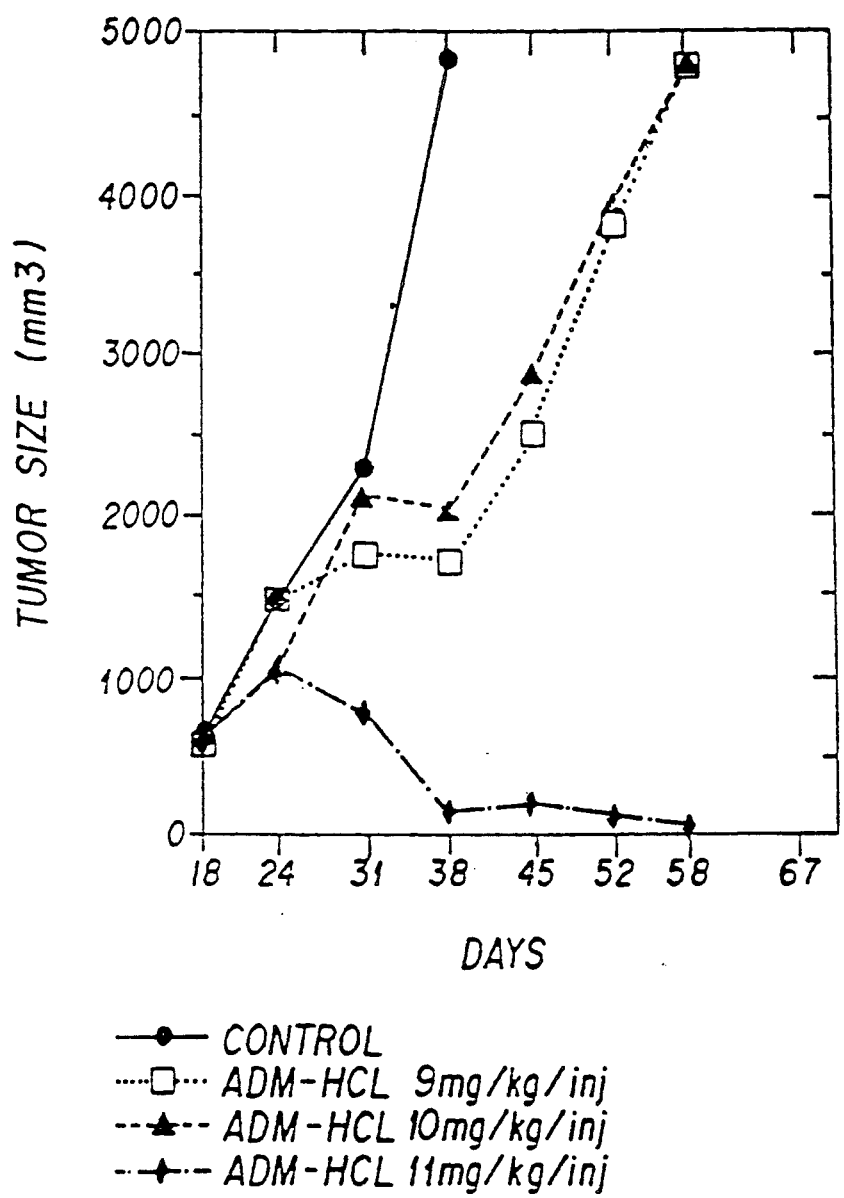
FIG. 22 depicts in graph form the in vivo anti-tumor activity of ADM on human Daudi tumor xenografts in mice over time and at varying dosages of ADM, using a Q7Dx3 treatment schedule and i.v. administration.

In this experiment, the free drug was dosed at 4.1 mg/kg/inj due to the toxicity associated with i.p.-administered free drug at doses above 4–5 mg/kg. At these low doses, both free ADM and mixtures of ADM The anti-tumor activity of free drug on Daudi tumor cells is further depicted in FIG. 22. Using the Q7Dx3 schedule, given i.v., the growth of Daudi tumor xenografts was significantly inhibited in a dose dependent fashion at 9, 10 or 11 mg/kg/injection, respectively, after treatment with ADM-HCl. Control mice were untreated. Inhibition of tumor growth (T-C) at the MTD, which was 11 mg/kg/inj, was 28 days which corresponded to a 1.1 TDD.

Various schedules using i.p. administration were also tested. As discussed above, the MTD of ADM-HCl, i.p., was determined to be between 4-5 mg/kg/inj. As ran be seen from Table 2B, the free drug is inactive on Daudi cells at its MTD via the i.p route. Thus, we determined that optimal anti-tumor activity for the free drug is obtainable via i.v. administration where the MTD is 11 mg/kg/inj, a drug dose that shows growth inhibition of Daudi tumor cells.

From these experiments, therefore, it was determined that the optimal ADM-HCl dosage for anti-tumor activity on Daudi tumors was approximately 11 mg/kg/inj, the optimal schedule was Q7Dx3 and the optimal route of administration was i.v.

Figure 23:
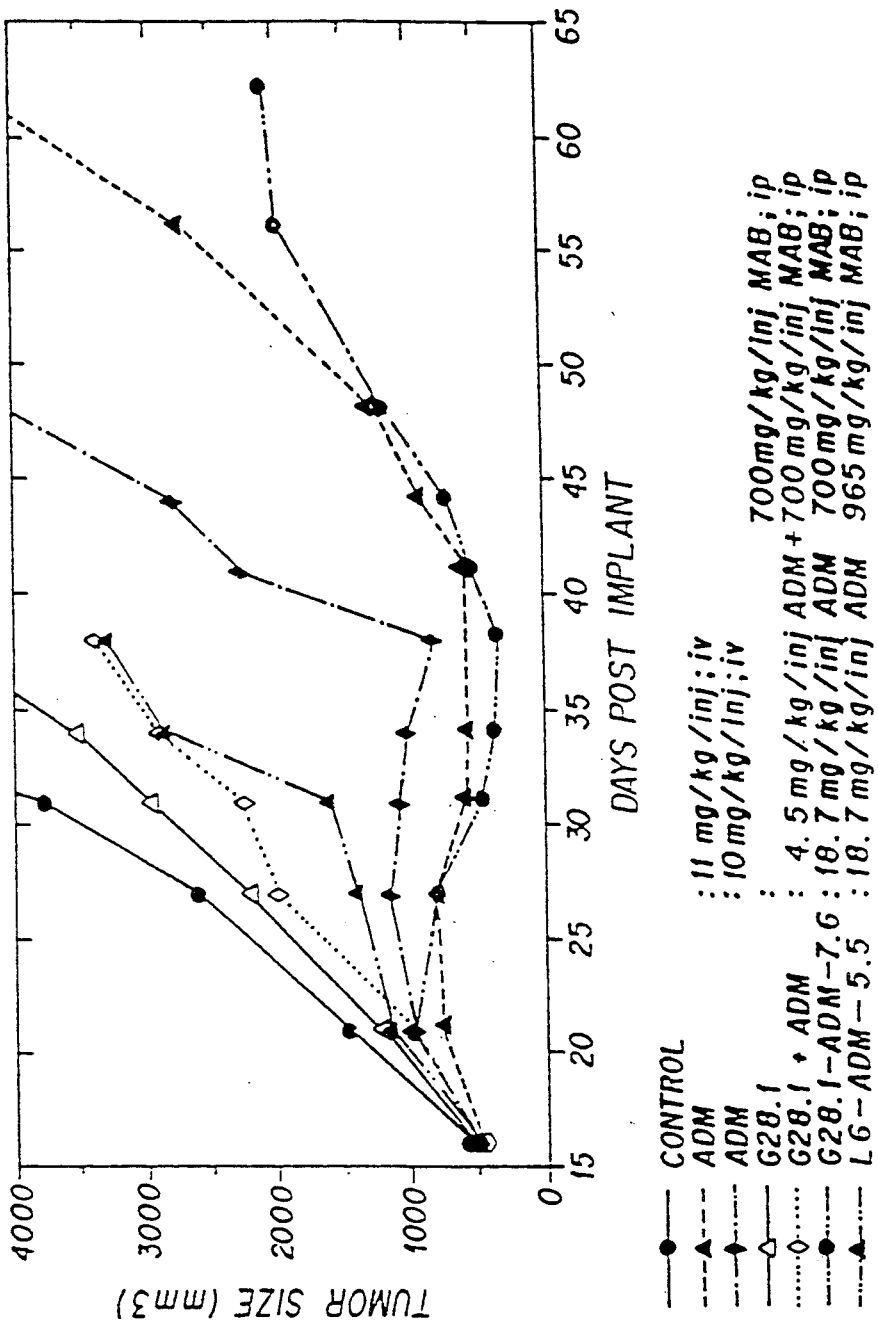
FIG. 23 depicts in graph form the in vivo anti-tumor activity of an immunoconjugate of the invention on human Daudi tumor xenografts in mice compared to the anti-tumor activity of optimized free ADM (given i.v. on a Q7Dx3 treatment schedule at a dose of 10-11 mg/kg/inj). The immunoconjugate showed a greater anti-tumor activity.

We next compared the anti-tumor activity on Daudi tumors of the ADM-immunoconjugates of this invention to the anti-tumor activity of the free ADM-HCl drug given under optimal conditions as determined above. A G23.1-ADM immunoconjugate, G28.1-ADM-7.6 (MR=7.6 drugs/MAB), dosed using a Q5Dx2 schedule, i.p., was compared to ADM-HCl dosed at 10, 11 and 12 mg/kg/inj on a Q7Dx3 schedule, i.v., schedule. As shown in FIG. 23 and Table 3 below, the free drug was active, giving a 28 day delay in tumor growth at 11 mg/kg (its MTD) with two of eight mice showing complete tumor regression (cures). The immunoconjugate at the highest tested dose (18.7 mg ADM, Q5Dx2, i.p.) was well tolerated (no deaths, no weight loss) and gave an anti-tumor activity somewhat higher than the free drug with three of the eight treated animals showing complete tumor regression. Again, there was no anti-tumor activity associated with non-binding L6-immunoconjugate, unconjugated G28.1 or a mixture of unconjugated G28.1 plus ADM-HCl. Thus, we determined that the ADM-immunoconjugates inhibited tumor growth to a greater extent than could be achieved using the unconjugated drug at its optimal dose and schedule, i.v. or i.p.

TABLE 3*

Anti-Tumor Activity
Of MAB Conjugated ADM (Q5D × 2; i.p.)
Compared To Optimized ADM-HCl (Q7D × 3; i.v.)
On Daudi Tumor Xenografts

| Dose (mg/kg)$^a$ | | Tumor Inhibition$^b$ | | | | Toxicity$^c$ | |
|---|---|---|---|---|---|---|---|
| ADM | MAB | T-C | CR | Cures | TDD | D/T | (%) |
| | | ADM-HCl | | Q7D × 3; i.v. | | | |
| 12 | | >33 | 3 | 3 | >1.5 | 2/8 | |
| 11 | | 28 | 0 | 2 | >1.1 | 0/8 | |
| 10 | | 18 | 0 | 1 | 0.8 | 0/8 | |
| | | G28.1-ADM (7.6) | | Q5D × 2; i.p. | | | |
| 18.7 | 700 | >31 | 0 | 3 | >1.5 | 0/8 | |
| 8.1 | 300 | 3 | 0 | 0 | 0.1 | 0/8 | |
| 4.4 | 165 | 1 | 0 | 0 | 0 | 0/8 | |
| | | L6-ADM (5.5) | | Q5D × 2; i.p. | | | |
| 18.7 | 965 | 7 | 0 | 0 | 0.3 | 0/8 | |
| 8.1 | 415 | 0 | 0 | 0 | 0 | 0/8 | |
| | | G28.1 + ADM | | Q5D × 2; i.p. | | | |
| 4.5 | 700 | 6 | 0 | 0 | 0.2 | 0/8 | |
| | | G28.1 | | Q5D × 2; i.p. | | | |

TABLE 3*-continued

Anti-Tumor Activity
Of MAB Conjugated ADM (Q5D × 2; i.p.)
Compared To Optimized ADM-HCl (Q7D × 3; i.v.)
On Daudi Tumor Xenografts

| Dose (mg/kg)$^a$ | | Tumor Inhibition$^b$ | | | | Toxicity$^c$ | |
|---|---|---|---|---|---|---|---|
| ADM | MAB | T-C | CR | Cures | TDD | D/T | (%) |
| | 700 | 2 | 0 | 0 | 0.1 | 0/8 | |

*See Table 2 for legend.

Table 4 summarizes the anti-tumor activity obtained using different preparations of 5E9 and G28.1 immunoconjugates on Daudi tumor xenografts in athymic mice. The highest response rate was consistently obtained at antibody doses of 500 mg/kg or greater. At these doses, anti-tumor activity was obtained using conjugates having molar ratios of 1.8 to 8.6. The anti-tumor activity appeared to be dependent upon the antibody dose rather than the conjugated drug dose as evidenced by the fact that as the monoclonal antibody dose increased, there was a corresponding increase in both TDD, i.e., inhibition of tumor growth and tumor regression rates. In all experiments, no anti-tumor activity was observed with the non-binding L6-ADM conjugates that were tested in parallel at equivalent antibody and conjugated drug doses (results not shown). In addition, this table illustrates the increased potency of the immunoconjugates of the invention as compared to free drug, which was inactive at equivalent drug doses (compare Table 2 above).

TABLE 4

Anti-Tumor Activity Of ADM-Immunoconjugates On Daudi Tumor Xenografts$^a$

| | Cum. Dose (mg/kg) | | T-C$^b$ | | |
|---|---|---|---|---|---|
| Conjugate - MR | MAB | ADM | (Days) | Cures | TDD |
| 5E9-ADM-4.2$^d$ | 200 | 4 | 10 | 0/7 | 0.5 |
| 5E9-ADM-8.6 | 260 | 8.2 | 8 | 0/5 | 0.3 |
| 5E9-ADM-4.2$^d$ | 500 | 5 | 17 | 1/7 | 0.8 |
| 5E9-ADM-5.4 | 1110 | 22.8 | 31 | 2/5 | 1.4 |
| 5E9-ADM-4.2$^d$ | 1200 | 18.3 | >61 | 2/7 | >1.5$^f$ |
| 5E9-ADM-1.8 | 1260 | 8.2 | >39 | 3/5 | >1.5 |
| G28.1-ADM-4.9 | 200 | 4 | 8 | 0/7 | 0.4 |
| G28.1-ADM-7.6$^e$ | 330 | 8.8 | 1 | 0/7 | 0 |
| G28.1-ADM-7.6$^e$ | 600 | 16 | 3 | 0/7 | 0.1 |
| G28.1-ADM-4.2 | 1110 | 16.8 | >37 | 2/3 | >1.7 |
| G28.1-ADM-4.9 | 1200 | 21.4 | >56 | 2/7 | >1.5$^f$ |
| G28.1-ADM-7.6$^e$ | 1400 | 37.4 | 31 | 3/8 | 1.3 |

$^a$Schedule: Q5D × 2  Route: i.p.  MR: mole ratio of drug molecules/MAB
$^b$T-C: represents the time delay in days for the drug-treated group (T) to reach 3000 mm$^3$ as compared to untreated controls (C).
$^c$Cures: cures/number of animals treated.
$^d$5E9-ADM-4.2 tested at three doses.
$^e$G28.1-ADM-7.6 tested at three doses.
$^f$Death in control group.

Table 5 below demonstrates the reduced toxicity achieved using the ADM-immunoconjugates of the invention vs. the unconjugated drug. As can be seen, the immunoconjugates were at least 10 times less toxic than free ADM dosed i.p.

TABLE 5

Toxicity of Free ADM and MAB-ADM in Tumor-Bearing Nude Mice$^a$

| | | | | ADM (mg/kg)$^c$ | | | % |
|---|---|---|---|---|---|---|---|
| Compound | N$^b$ | Schedule | Route | inj | Cumulative | D/T | Deaths |
| ADM | 4 | Q1D × 1 | i.v. | 18 | 18 | 14/32 | 44 |
| ADM | 3 | Q1D × 1 | i.v. | 16 | 16 | 3/31 | 10 |
| ADM | 1 | Q1D × 1 | i.v. | 14 | 14 | 0/8 | 0 |
| ADM | 1 | Q2D × 2 | i.v. | 15 | 30 | 7/7 | 100 |
| ADM | 2 | Q2D × 2 | i.v. | 12 | 24 | 10/12 | 83 |
| ADM | 1 | Q2D × 2 | i.v. | 10 | 20 | 3/5 | 60 |
| ADM | 1 | Q2D × 2 | i.v. | 8 | 16 | 1/5 | 20 |

TABLE 5-continued

Toxicity of Free ADM and MAB-ADM in Tumor-Bearing Nude Mice[a]

| Compound | N[b] | Schedule | Route | ADM (mg/kg)[c] inj | ADM (mg/kg)[c] Cumulative | D/T | % Deaths |
|---|---|---|---|---|---|---|---|
| ADM | 1 | Q3D × 2 | i.v. | 16 | 32 | 8/8 | 100 |
| ADM | 1 | Q3D × 2 | i.v. | 14 | 28 | 7/8 | 88 |
| ADM | 1 | Q3D × 2 | i.v. | 12 | 24 | 6/8 | 75 |
| ADM | 1 | Q4D × 2 | i.v. | 14 | 28 | 6/7 | 86 |
| ADM | 2 | Q4D × 2 | i.v. | 12 | 24 | 7/15 | 47 |
| ADM | 1 | Q4D × 2 | i.v. | 10 | 20 | 2/8 | 25 |
| ADM | 1 | Q7D × 3 | i.v. | 12 | 36 | 4/8 | 50 |
| ADM | 3 | Q7D × 3 | i.v. | 11 | 33 | 4/26 | 15 |
| ADM | 3 | Q7D × 3 | i.v. | 10 | 30 | 0/24 | 0 |
| ADM | 1 | Q8D × 2 | i.p. | 13 | 26 | 7/7 | 100 |
| ADM | 1 | Q8D × 2 | i.p. | 10 | 20 | 8/8 | 100 |
| ADM | 1 | Q8D × 2 | i.p. | 5 | 10 | 3/8 | 38 |
| ADM | 1 | Q4D × 3 | i.p. | 5 | 15 | 6/9 | 67 |
| ADM | 1 | Q5D × 2 | i.p. | 5.5 | 11 | 0/8 | 0 |
| ADM | 1 | Q5D × 2 | i.p. | 4.1 | 8.2 | 1/5 | 20 |
| G28.1-ADM | 1 | Q1D × 4 | i.p. | 27.2 | 55.4 | 0/8 | 0 |
|  | 1 | Q5D × 2 | i.p. | 18.7 | 37.4 | 0/8 | 0 |
| G28.1-ADM | 1 | Q1D × 4 | i.p. | 24 | 96 | 3/8 | 38 |
|  | 1 | Q1D × 4 | i.p. | 14 | 64 | 0/8 | 0 |
| G28.1-ADM | 1 | Q1D × 4 | i.p. | 10.5 | 42 | 0/5 | 0 |
| L6-ADM | 1 | Q1D × 4 | i.p. | 31 | 124 | 1/8 | 13 |
|  | 1 | Q1D × 4 | i.p. | 18.6 | 74 | 0/8 | 0 |

Figure 25:
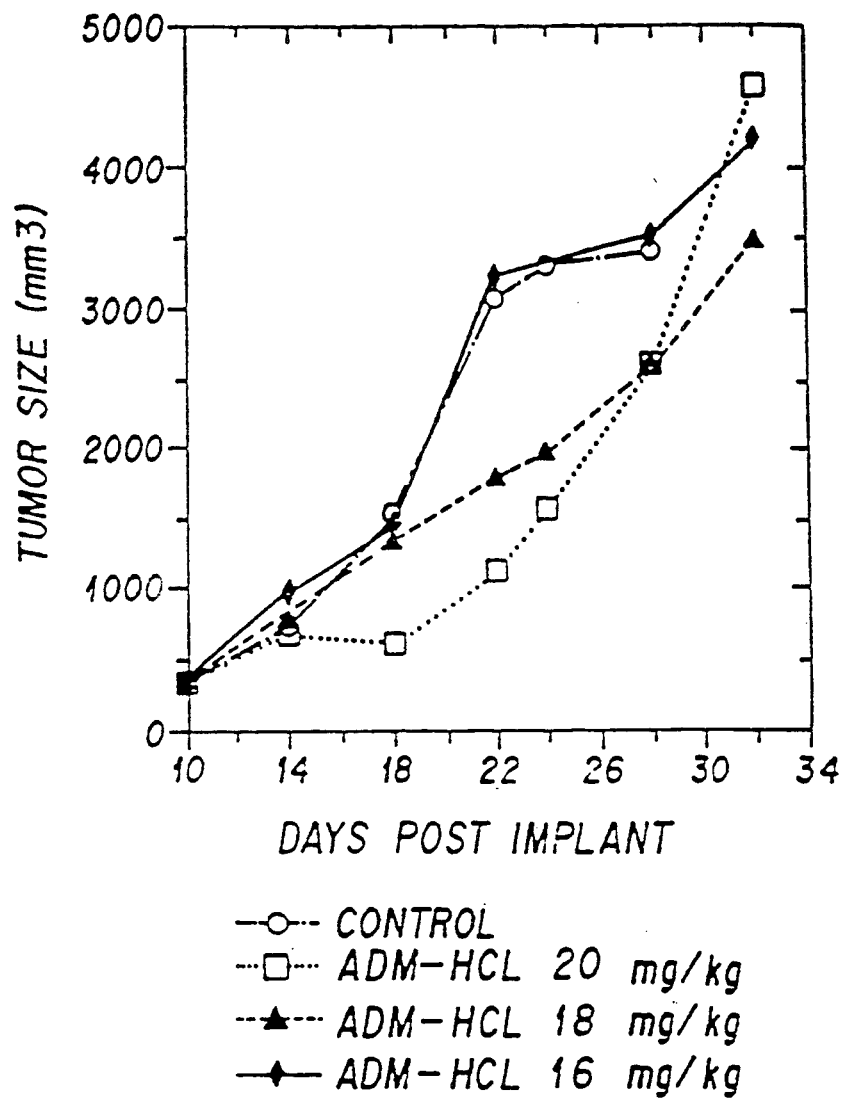
FIG. 25 depicts in graph form the in vivo anti-tumor activity of ADM on human Ramos tumor xenografts in mice over time and at varying dosages of ADM, using a single injection treatment schedule and i.v. administration.

[a] Mice Bearing Daudi or Ramos Tumors
[b] N = Number of Experiments
[c] ADM = Amount Given Free or Conjugated to MAB
[d] D/T = # Deaths/Total Treated Finally, FIG. 26A and Table 6 depict the anti-tumor activity of G28.1-ADM conjugates on human Ramos tumors. Again, the anti-tumor effect of the immunoconjugates on Ramos tumors was compared to that observed using free ADM-HCl under conditions which gave optimal results, which was previously determined to be a single dose injection at a dosage of 16-18 mg/kg/inj (see FIGS. 24 and 25). At the highest immunoconjugate dose tested (10.6 mg/kg), the anti-tumor activity of the conjugate was superior to the activity obtained using free drug at 18 mg/kg (25% lethality) by 0.5 TDD and to the activity of ADM-HCl at 16 mg/kg (12% lethality) by 1.C TDD. The conjugate at this dose was well tolerated with all of the treated animals showing no weight loss or deaths. The anti-tumor activity of G28.1-ADM was also found to be dose dependent as shown in FIG. 26B. Thus, decreasing the conjugate dose resulted in decreases in the TDD and number of complete regressions. The L6-ADM (non-binding) conjugate at a comparable dose (10.6 mg/kg) was inactive.

TABLE 6

Anti-Tumor Activity Of MAB Conjugated ADM (Q1D × 4; i.p.) To Optimized ADM-HCl (Q1D × 1; i.v.) Using Ramos Tumor Xenografts

| Dose (mg/kg)[a] ADM | Dose (mg/kg)[a] MAB | Tumor Inhibition[b] T-C | Tumor Inhibition[b] CR | Tumor Inhibition[b] Cures | Tumor Inhibition[b] TDD | Toxicity[c] D/T | Toxicity[c] (%) |
|---|---|---|---|---|---|---|---|
| ADM-HCl Q7D × 3; i.v. | | | | | | | |
| 18 |  | 8 | 0 | 0 | 0.5 | 2/8 | (25) |
| 16 |  | 5 | 0 | 0 | 0.3 | 1/8 | (12) |
| G28.1-ADM (4.8) Q1D × 4; i.p. | | | | | | | |
| 10.6 | 600 | 10.5 | 0 | 1 | 1.1 | 0/5 |  |
| 5.3 | 300 | 5 | 0 | 0 | 0.5 | 0/5 |  |
| 2.6 | 150 | 3.5 | 0 | 1 | 0.4 | 0/5 |  |
| L6-ADM (7.9) Q1D × 4; i.p. | | | | | | | |
| 18.2 | 600 | — | — | — | — | 2/5 | (40) |
| 10.6 | 360 | 0 | 0 | 1 | 0 | 0/5 |  |

[a] Dose per injection.
[b] See Table 2 for legend.

The above examples therefore demonstrate the preparation of novel anthracycline immunoconjugates in which a cytotoxic anthracycline drug is conjugated to an antibody via a novel acid-sensitive acylhydrazone linkage. The immunoconjugates retain both antibody binding activity (i.e., target cell specifity) and cytotoxic drug activity and allow the release of free unmodified drug under acidic and reducing conditions typical of the cellular environment of the target cells. The anti-tumor activity of these conjugates has been demonstrated both in vitro and in vivo and has been shown to be greater than the activity obtained with the free unconjugated anthracycline. Furthermore, the immunoconjugates were tolerated in vivo to a much greater extent than the unconjugated drug. Thus, the immunoconjugates of this invention show an enhanced therapeutic index (of anti-tumor activity vs. toxicity) and are therefore particularly useful in delivering cytotoxic drugs to a selected cell population for the preferential killing of those cells in the treatment of diseases such as cancers and other tumors, non-cytocidal viral or other pathogenic infections and autoimmune disorders.

EXAMPLE 4

The following example demonstrates the preparation of a novel anthracycline-ligand conjugate wherein adriamycin is linked to the peptide ligand, bombesin, via an acylhydrazone bond at the 13-keto position of the drug.

Preparation Of A Bombesin-ADM Conjugate

Crude cys-bombesin with the amino acid sequence: Cys-Glu-Gln-Lys-Leu-Gly-Asn-Gln-Trp-Ala-Val-Gly-His-Leu-Met-NH$_2$, was prepared by Vega Biotechnologies (Tuscon, Ariz.). Alternatively, we have synthesized cys-bombesin on a Milligen 9050 peptide synthesizer using activated pentafluoro esters of Fmoc protected amino acids. The synthesized peptide was cleaved from the resin, and side chain protecting groups removed by incubation in 92.5% Trifluoroacetic acid, 2.5% thiophenol and 5% phenol for 2 h at 25° C.

Cys-bombesin was then purified from the crude peptide mixture by C18 reverse phase HPLC (Perkin Elmer 410 Bio HPLC) followed by ion-exchange HPLC. In a typical preparation, 10 mg of crude peptide and 20 mg dithiothreitol (DTT) were dissolved in 10% acetonitrile in 0.01M ammonium acetate, pH 6.0, and separated using a 10–50% acetonitrile gradient in 0.01M ammonium acetate, pH 6.0. Eluates were monitored at $OD_{280}$. Fractions (1 ml) were collected and fractions containing reactive thiol groups were identified by reaction with DTNB as described earlier in Example 1.

These fractions containing reactive thiol groups were also tested for bombesin immunoreactivity in an Elisa assay with an anti-bombesin monoclonal antibody that binds to the region of the bombesin peptide that is known to interact with the bombesin receptor. The assay was performed as follows: The bombesin peptide (100 ng–1 μg) was absorbed onto Immulon II Elisa plates for 2 h at 37° C. The plates were blocked with 3% gelatin for 2 h at 37° C., washed five times with PBS containing 0.05% Tween 20, incubated with mouse anti-bombesin antibody (Boehringer Mannheim) for 1 h at 37° C., and then washed five times with PBS Tween 20. The plates were then incubated with peroxidase-labeled rabbit anti-mouse Ig (Boehringer Mannheim), prior to being developed with TMB substrate according to the manufacturer's instructions (Kirkegaard and Perry).

Fractions from several runs containing free sulfhydryl groups and displaying bombesin immunoreactivity were pooled and further purified by ion-exchange HPLC (Aquapore CX-300 10 μm column from Rainin) using a 2–50% salt gradient (500 mM ammonium acetate, pH 6.0) in 10% acetonitrile. Eluates were monitored at $OD_{280}$ and 1 ml fractions were tested for free thiol groups by the DTNB method and for bombesin immunoreactivity by Elisa assay as described above. Fractions were pooled, concentrated using a Savant speed-vac and rechromatographed by HPLC on a C18 column as described above. The final cys-bombesin product displayed a single peak in the HPLC chromatograph (see FIG. 28).

The purified cys-bombesin was then used for reaction with ADM-HZN as follows: The purified cys-bombesin was made to about 5–8 mg/4 ml in 10 mM ammonium acetate (1.25–2 mg/ml) based on the $A_{280}$ of 2.08 for 1 mg/ml purified Lys[3]-bombesin. The pH was adjusted to 7.0 with 7M NH4OH and then 2.5–4 mg of ADM-HZN, in 400 μl methanol, was added. The solution was vortexed and left for 1 h at 20° C. and then 12 h at 4° C. with intermittent mixing. The cys-bombesin-ADM conjugate was separated from free drug by ion-exchange HPLC using the conditions outlined above for free peptide with the exception that the acetonitrile concentration was maintained at 40% throughout the separation. Fractions containing the conjugate were pooled, dried down on a Savant speed-vac, and dissolved in the starting buffer for the reverse phase HPLC separation, as outlined earlier. Free peptide was then separated from the peptide-drug conjugate by reverse phase HPLC chromatography (as described earlier for purification of free peptide). The column was monitored at 280 nm and 495 nm. Fractions containing the conjugate were pooled, dried down and stored at −20° C. for further characterization.

Alternatively, a bombesin-ADM conjugate was prepared wherein ADM was linked to the bombesin peptide at the lysine residue (Lys[3]) of the peptide. According to this bombesin (also termed Lys[3]-bombesin) was incubated with a 3 mole excess of SPDP at pH 8.5 for 1 h at 25° C. The bombesin was separated from excess SPDP by C18 reverse phase HPLC, reduced with excess DIT and then rechromatographed by C18 reverse phase HPLC as described above. The reduced peptide was then incubated with a 2 mole excess of ADM-HZN for 1 h at 25° C., followed by 14 h at 4° C. Attempts, however, to separate the peptide-drug conjugate from the drug were problematic for two reasons: 1) on C18 chromatography as described for the preparation of cys-bombesin above, the peptide-drug conjugate (detected by Elisa assay as described above) was hydrophobic and behaved very similarly to the ADM-HZN alone but different from the reduced peptide and 2) modification of the bombesin through the lysine[3] residue alters the charge on the peptide, making it more difficult to separate from free drug by ion exchange chromatography. Coupling through a cys-bombesin peptide was therefore favored.

Characterization Of The Bombesin-ADM Conjugate

Figure 29A:
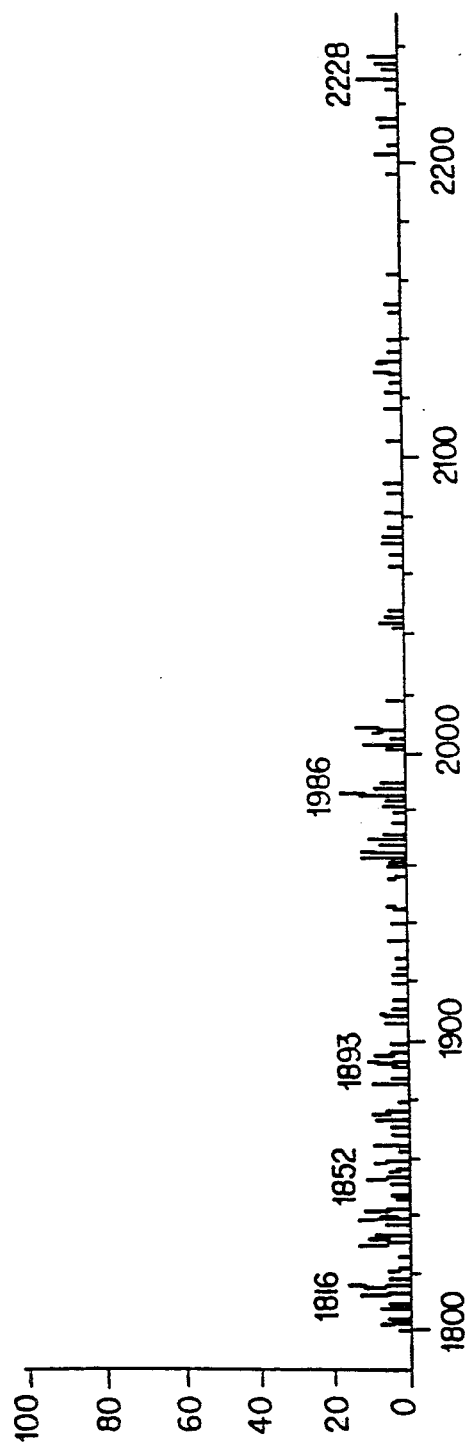
FIGS. 29A and 29B depict a mass spectrum of the cys-bombesin-ADM conjugate of the invention.
Figure 29B:
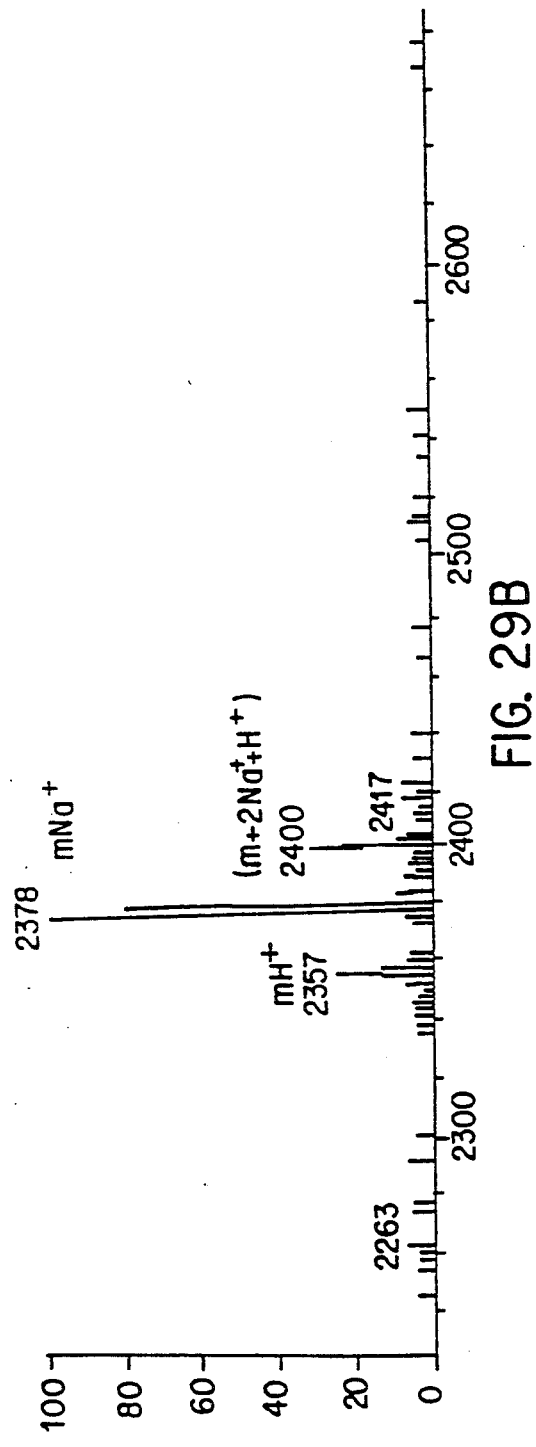

The bombesin-ADM conjugate prepared from cys-bombesin as described above has the structure illustrated in FIG. 27, the ADM being conjugated to a linker arm at the 13-keto position via an acylhydrazone bond. The linker, bridging the peptide and the drug, contained a disulfide bond within its structure. FIG. 29 depicts a mass spectrum of the cys-bombesin-ADM conjugate. This analysis shows a molecular ion of 2357 which corresponds to the 1:1 adduct of cys-bombesin and ADM.

The cys-bombesin-ADM conjugate was tested for its ability to bind to bombesin receptors on the Swiss 3T3 cell line, a normal mouse fibroblast cell line obtained from the ATCC. Binding was measured using a competition assay involving the use of $^{125}$I-labeled gastrin-releasing peptide (GRP). GRP, like bombesin, binds to the bombesin receptor on the surface of receptor-positive cells such as Swiss 3T3 cells. Thus, $^{125}$I-labeled GRP was incubated with increasing concentrations of cys-bombesin, GRP or the cys-bombesin-ADM conjugate and specifically bound radioactivity was quantitated. In this way, inhibition of $^{125}$I-GRP binding was measured.

The assay was carried out as follows: The Swiss 3T3 cells were allowed to grow to confluence (5–7 days) in 150 cm[2] T-flasks in MEM medium supplemented with 10% fetal bovine serum, penicillin (100 units/ml) and streptomycin (100 μg/ml) (complete medium) After the cells reached confluency, the medium was replaced with MEM complete medium supplemented with insulin (5 μg/ml), transferrin (5 μg/ml) and sodium selenite (5 ng/ml). The cells were incubated for an additional 24 h and harvested by scraping with a rubber policeman into RPMI/HITS [RPMI 1640 containing BSA (5 mg/ml), HEPES (4.7 mg/ml), insulin (5 μg/ml), transferrin (5 μg/ml) and sodium selenite (5 ng/ml)]. The cells were washed one time and passaged 3 times through a 22 gauge needle to obtain a single cell suspension. Next, 10 μl of cys-bombesin, GRP or the bombesin-ADM conjugate at various dilutions (in triplicate) were added to tubes containing $5 \times 10^5$ cells to which was also added 150 μl of $^{125}$I-GRP (2 ng/ml, 2000 Ci/mmol). The tubes were mixed and incubated for 1 h at room temperature on a shaking platform. Cell-bound $^{125}$I-GRP was separated by centrifugation at $12,000 \times g$ over a layer of 1:1 dibutylphthalate:dioctylphthalate in a microfuge tube. The tubes were frozen on dry ice, and cell pellets cut off and counted in a LKB 1275 gamma counter.

Figure 30:
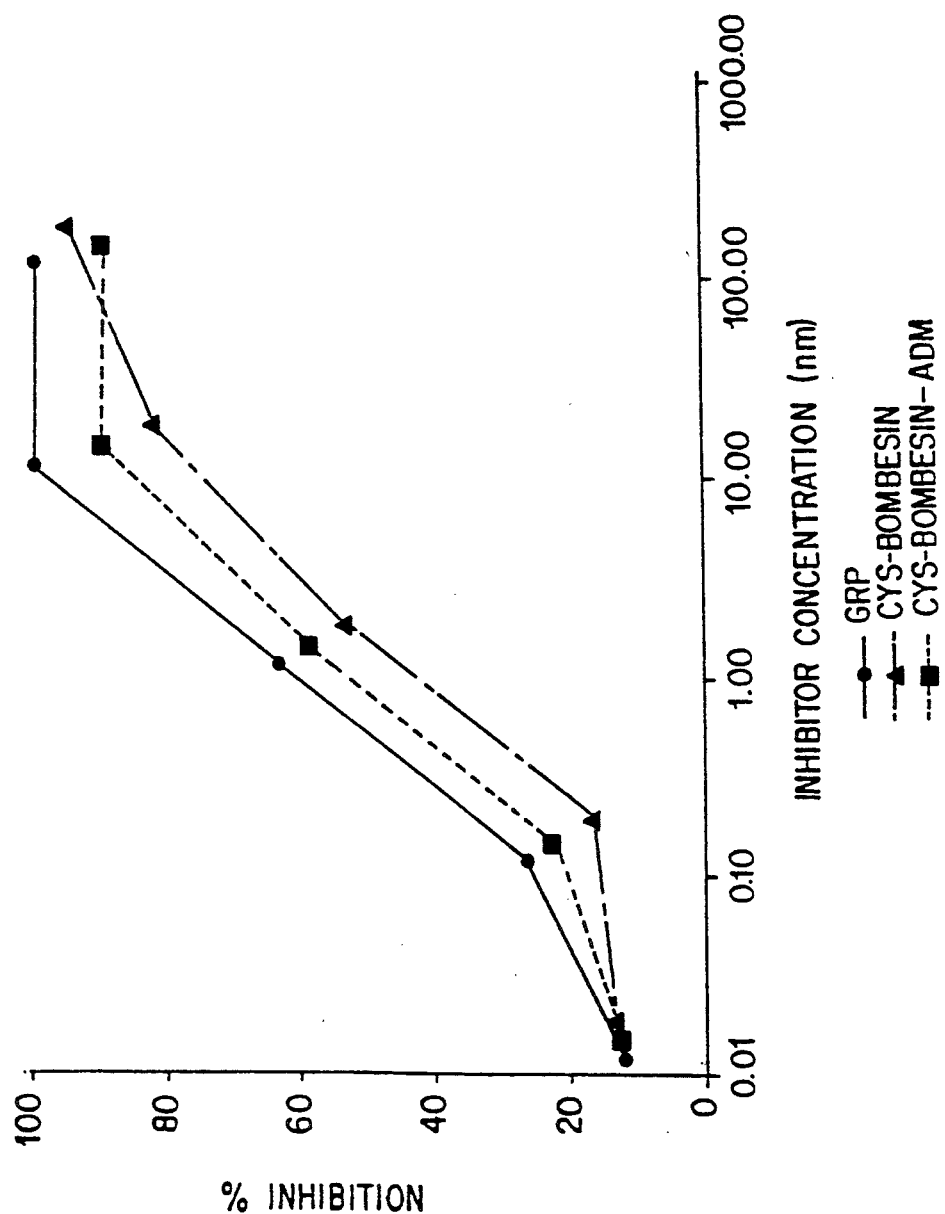
FIG. 30 depicts in graph form a competitive binding assay on Swiss 3T3 cells, wherein $^{125}$I-GRP was incubated with increasing concentrations of a cys-bombesin-ADM conjugate of the invention, cys-bombesin or GRP, and inhibition of $^{125}$I-GRP binding to the cells was measured. This assay demonstrated the retention of binding activity by the cys-bombesin-ADM conjugate for bombesin receptors on the cells.

As demonstrated in FIG. 30, there was specific competition of $^{125}$I-labeled GRP binding to the 3T3 cells by GRP, cys-bombesin and the cys-bombesin-ADM conjugate. More importantly, there was no significant difference in the competition curves of the three molecules indicating that they display similar affinities for the bombesin receptor. Thus, the conjugation of ADM to bombesin does not disturb the binding activity of the peptide, the conjugate retaining the ability to bind to bombesin receptor-positive cells. Other studies performed in our labs have confirmed that cys-bombesin and bombesin display equivalent binding activities on receptor-positive cells.

Cytotoxic Activity Of The Bombesin-ADM Conjugate

The cytotoxic activity of the cys-bombesin-ADM conjugate was determined using a $^3$H-thymidine uptake assay. According to this assay, cells of various types that carry the bombesin receptor on their cell surfaces, were added to 96-well microtiter plates (5000 cells/well) and grown for 24 h at 37° C. in MEM medium. These cells included the Swiss 3T3 fibroblast cell line described earlier, the SVT2 cell line, a transformed fibroblast cell line obtained from the ATCC, and the HCT116 cell line, a colon carcinoma cell line described in Example 1. Dilutions were made of the cys-bombesin-ADM conjugate, ADM, ADM-HZN, or a mixture of cys-bombesin-ADM plus 20 μg/ml bombesin, in HITS medium containing RPMI 1640 medium, bovine serum albumin (5 mg/ml), HEPES (0.02M), insulin (5 μg/ml), transferrin (5 μg/ml) and sodium selenite (5 ng/ml). Fifty μl of each dilution (in triplicate) of conjugate, drug or mixture were added to the wells containing the cells and incubated at 37° C. for a minimum of 1 h. Control wells were maintained to which only medium was added. The cells were then washed, 200 μl of fresh medium was added and the wells were incubated for an additional 38-44 h in HITS medium at 37° C. in a humid, 5% CO$_2$ atmosphere. One μCi of $^3$H-thymidine (New England Nuclear) in 50 μl medium was added to each well and incubated for 4 h at 37° C. A solution of trypsin (0.05%) in EDTA (0.53 nM) was added for 15 min and the cells were harvested in a mash harvester. Filters were placed in RPI 3a70B scintillation fluid and counted in a Beckman LS5801 scintillation counter. Cytotoxicity was determined using the formula:

% Inhibition $^3$H-TdR =

$$\frac{\text{Control (cpm)} - \text{Experimental (cpm)}}{\text{Control (cpm)}} \times 100$$

Figure 31:
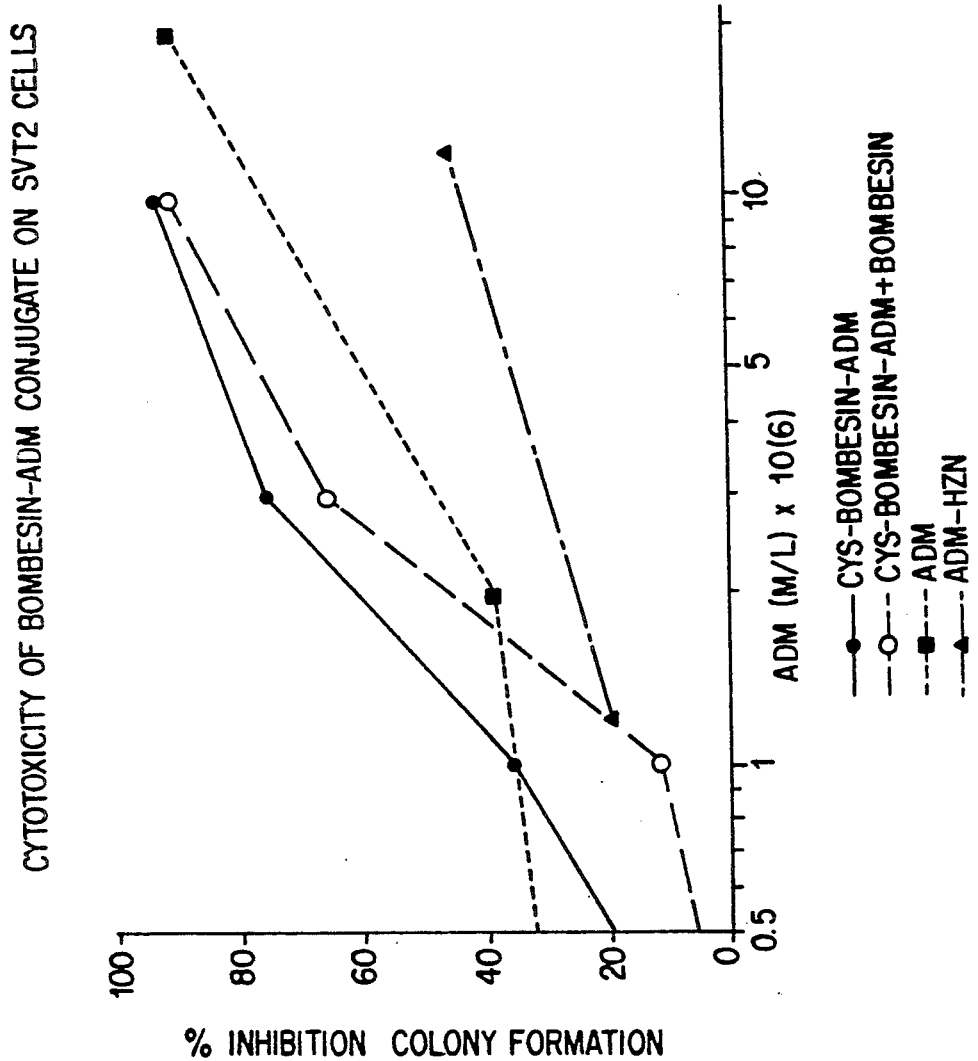
FIG. 31 depicts in graph form the cytotoxicity of a cys-bombesin-ADM conjugate of the invention toward SVT2 cells, using a $^3$H-thymidine incorporation assay. The conjugate showed a greater potency relative to free ADM or ADM-HZN toward the cells.
Figure 32:
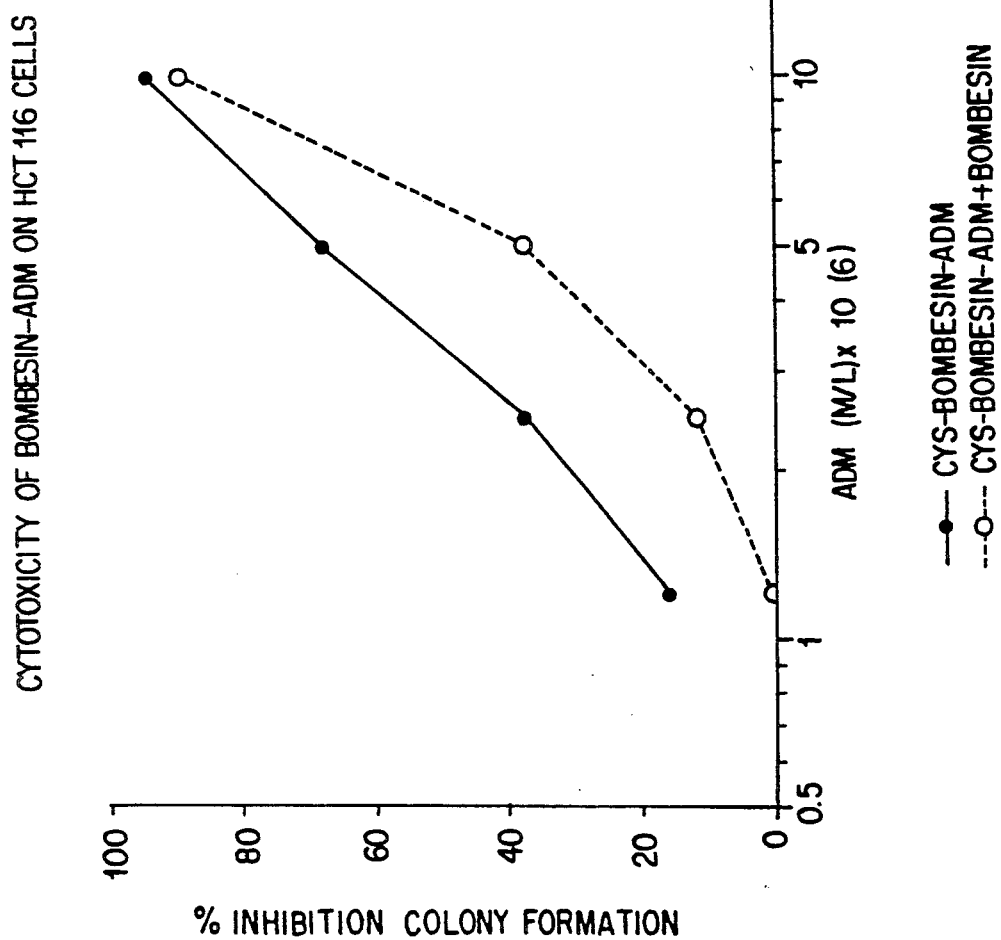
FIG. 32 depicts in graph form the cytotoxicity of a cys-bombesin-ADM conjugate of the invention toward HCT116 cells, using a $^3$H-thymidine incorporation assay.
Figure 33:
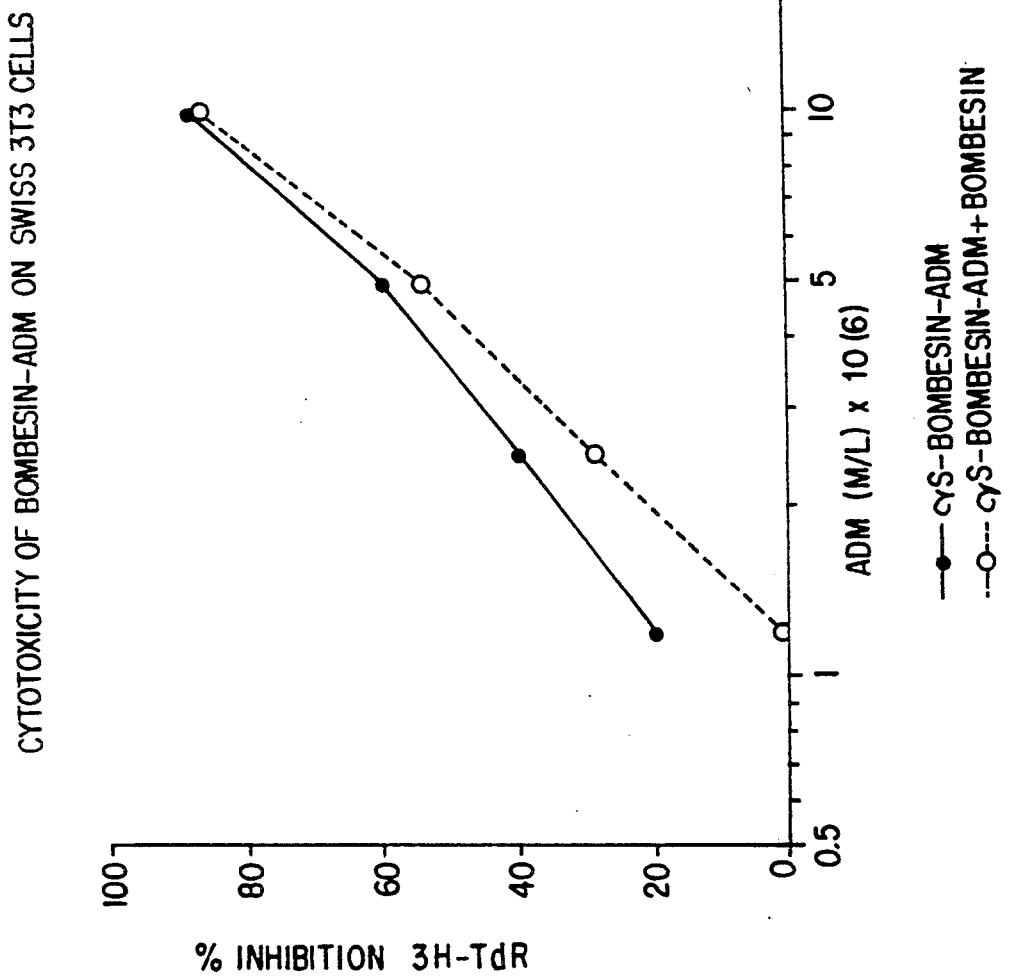
FIG. 33 depicts in graph form the cytotoxicity of a cys-bombesin-ADM conjugate of the invention toward Swiss 3T3 cells, using a $^3$H-thymidine incorporation assay.
Figure 34A:
FIGS. 34A to 34D show an HPLC chromatographs demonstrating the purity of an EGF-ADM conjugate preparation of the invention.
Figure 34B:
Figure 34C:
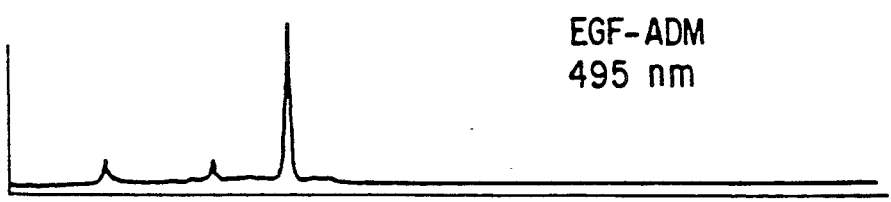
Figure 34D:

We thus measured the inhibition of $^3$H-thymidine incorporation into the DNA of the bombesin-receptor-positive cell lines in the presence of the conjugate of the invention and therefore, the cytotoxic effect of the conjugate on the cells. As shown in FIG. 31, the cys-bombesin-ADM conjugate was highly cytotoxic toward SVT2 cells and in fact, was more potent than free ADM or ADM-HZN. A portion of the cytotoxic activity of the cys-bombesin-ADM conjugate was blocked by excess bombesin (i.e., the mixture of the conjugate plus bombesin), indicating that the conjugate's cytotoxic effect was due at least in part to specific binding of the conjugate to the bombesin receptor. As shown in FIGS. 32 and 33, the conjugate was also specifically cytotoxic (after a 2 h exposure) toward HCT116 and Swiss 3T3 cells.

EXAMPLE 5

The following example describes the preparation of another anthracycline-ligand conjugate of the invention, wherein ADM is conjugated to the polypeptide ligand, EGF, via a linker that is attached to the ADM by a 13-keto acylhydrazone bond.

Preparation Of An EGF-ADM Conjugate

According to this embodiment of the invention, ADM was conjugated to a murine EGF purchased from Biomedical Technologies, Inc. (Staughton, Mass.). The EGF was obtained from mouse submaxillary glands, purified by a modification of the procedure of Cohen, J.B.C., 237, pp. 1555-62 (1962) and purchased as a sterile lyophilized powder (cat #: BT-201) at 0.1 mg/amp. See also Savage et al., J. Biol. Chem., 22, p. 7669 (1973). The peptide was then thiolated using SPDP to introduce a reactive thiol group onto the peptide. In the case of murine EGF, however, there are no internal lysine residues for attachment of SPDP and therefore, the only site for attachment of SPDP is at the amino-terminal amino acid, giving rise to a compound having at least one reactive sulfhydryl group per EGF molecule (after reduction with DTT). Thiolation of human EGF should theoretically result in a greater degree of substitution, since the molecule does have internal lysine molecules.

Thus, EGF was first dissolved in 0.1 ml PBS to give a final concentration of 1.0 mg/ml. To this solution, 0.01 ml of SPDP (final concentration: 10 mM) (purchased and diluted as described in Example 1, for antibody thiolation) was added. The reaction mixture was incubated for 30 min at 30° C. after which 0.02 ml of DTT (50 mM) was added to remove the thiopyridyl protecting group. Excess DTT and SPDP were removed from the thiolated EGF by microdialysis against PBS using dialysis membranes of 3,500 molecular weight cutoff (Spectrum Medical Industries Inc., cat #: 132723).

The thiolated murine EGF was then reacted with a 5-6 fold excess of ADM-HZN prepared and diluted as described in Example 1 above. For this example, 0.01 ml cf ADM-HZN (1.2×10$^2$M) was added to 0.1 mg SPDP-thiolated EGF in a final volume of 0.2 ml PBS, cooled to 4° C. The reaction mixture was incubated overnight at 4° C., and dialyzed against PBS, as described above for SPDP removal, to remove any unreacted drug from the conjugate.

Purity of the conjugate was determined by HPLC (see FIG. 34). The HPLC was done on a Brownlee column packed with 5 micron RP18 beads. The EGF-ADM conjugate was compared to unconjugated murine EGF (same source and lot #) and unconjugated ADM. Samples were eluted with an ammonium formate (pH 2.8)/acetonitrile gradient at 1.0 ml/min. As shown in FIG. 34, when the conjugated EGF, i.e., the EGF-ADM conjugate of this invention, was compared to unconjugated EGF, there was a homogeneous shift in retention time of the protein to a new protein peak. Similarly, when the conjugate was compared to unconjugated ALM, a similar shift in retention time of the conjugated drug peak from free ADM was observed. This HPLC chromatograph illustrates that there was less than 1% free drug (as detected at 495 nm) or free ligand (as detected at 280 nm) in the final conjugate preparation.

Purity of the conjugate was also determined by SDS-PAGE analysis on a non-reducing SDS-PAGE gel (8-25% gradient gel) (data not shown). Individual protein bands were resolved by staining with silver stain (Pharmacia Phastgel silver stain kit; cat #: 17-0617-01). The EGF-ADM conjugate (at approximately 0.1 and 0.05 mg/ml) was compared to three dilutions of unconjugated murine EGF (1, 0.1, and.01 mg/ml). There was no evidence of any protein bands in the EGF-ADM preparation that corresponded to unconjugated EGF protein. This experiment supported the conclusion of FIG. 34 that there was no evidence of unconjugated EGF in the EGF-ADM conjugate preparation.

Retention Of Binding Activity Of The EGF-ADM Conjugate

The retention of EGF binding activity after chemical coupling of ADM-HZN to EGF was determined by a competition radioisotope assay, using the A431 cell line. This cell line was derived from a human lung carcinoma and in our laboratory can bind between $1-4 \times 10^7$ molecules of EGF (results not shown). Cells, diluted in RPMI 1640 growth medium containing 10% FCS, were plated in 96-well microtiter plates ($5 \times 10^5$ cells/well) 24 h before the assay. On the day of the assay, the A431 cells, which grow as an adherent cell population, were washed in DMEM containing 2% bovine serum albumin (hereafter referred to as buffer A). Cells (in triplicate) were incubated with 0.05 ml of 2-fold serially diluted EGF or EGF-ADM, and 0.05 ml of $^{125}$I-labeled EGF (50 ng/ml) diluted in buffer A (final volume: 0.1 ml/well). The cells were incubated at 4° C. for 4 h, and then washed 3 times with buffer A. The cells were removed from the 96-well plastic plates by solubilization with 1.0M NaOH, and the amount of cell-bound $^{125}$I-EGF was determined by counting on a LKB model 1272 gamma counter.

Figure 35:
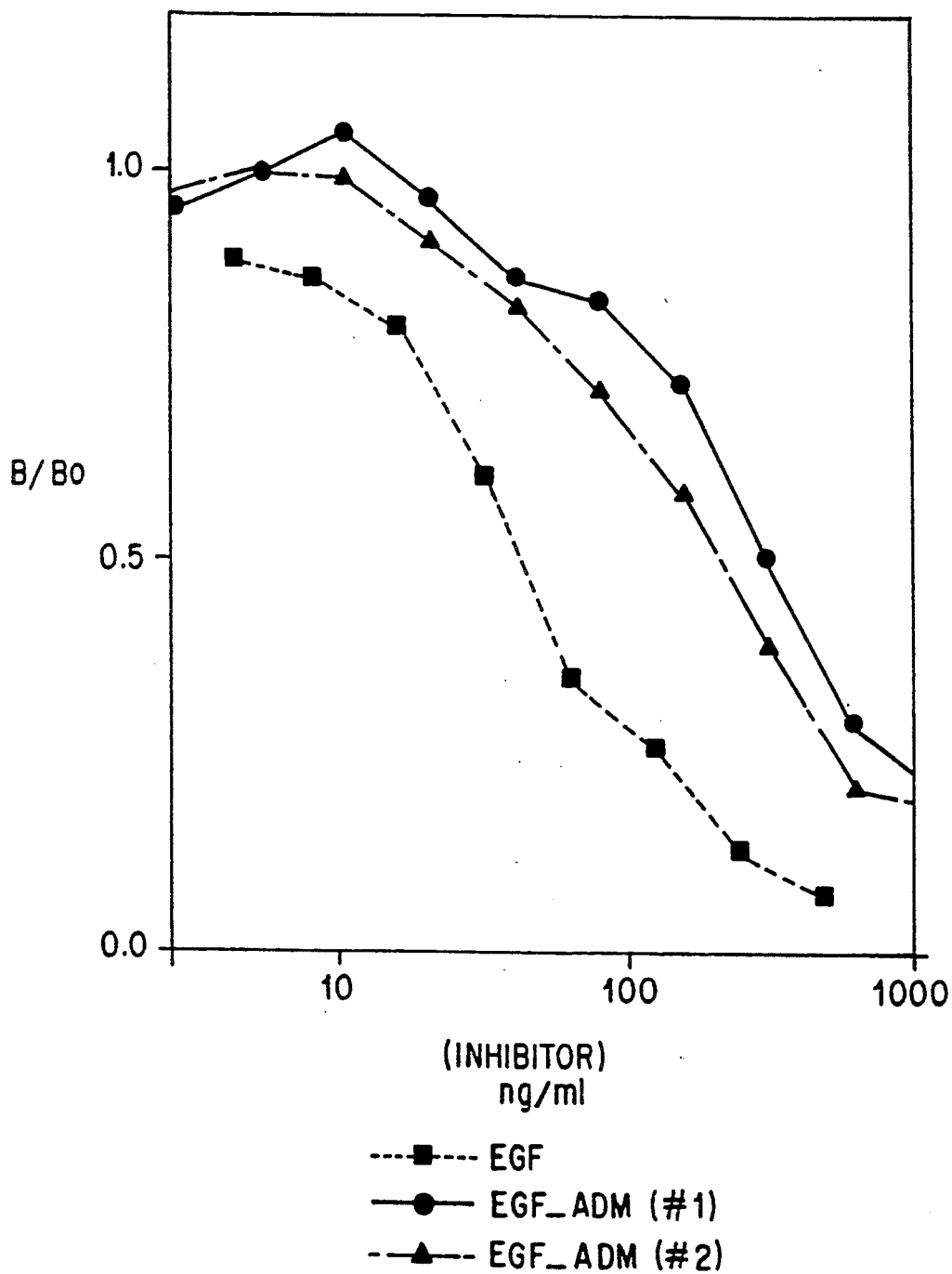
FIG. 35 depicts in graph form a competitive binding assay on A431 cells, wherein $^{125}$I-EGF was incubated with increasing concentrations of an EGF-ADM conjugate of the invention or EGF, and inhibition of $^{125}$I-EGF binding to the cells was measured. This assay demonstrated the retention of binding activity by the EGF-ADM conjugate for EGF receptors on the cells.

The binding activity of the EGF-ADM conjugate for its receptor on A431 cells is demonstrated in FIG. 35, which compares the ability of increasing concentrations of EGF-ADM to inhibit the binding of $^{125}$I-labeled EGF. The data is presented as inhibition of $^{125}$I-EGF binding (B/Bo) where B represents the cell bound radioactive counts at various concentrations of inhibitor (B) divided by the cell bound counts without any inhibitor (Bo). Two separate EGF-ADM conjugate preparations were compared to unconjugated EGF. Both conjugate preparations showed similar binding activities. When compared to unconjugated EGF, the EGF-ADM conjugates showed only a small loss in binding activity for the EGF receptor on A431 tumor target cells.

EXAMPLE 6

Figure 27A:
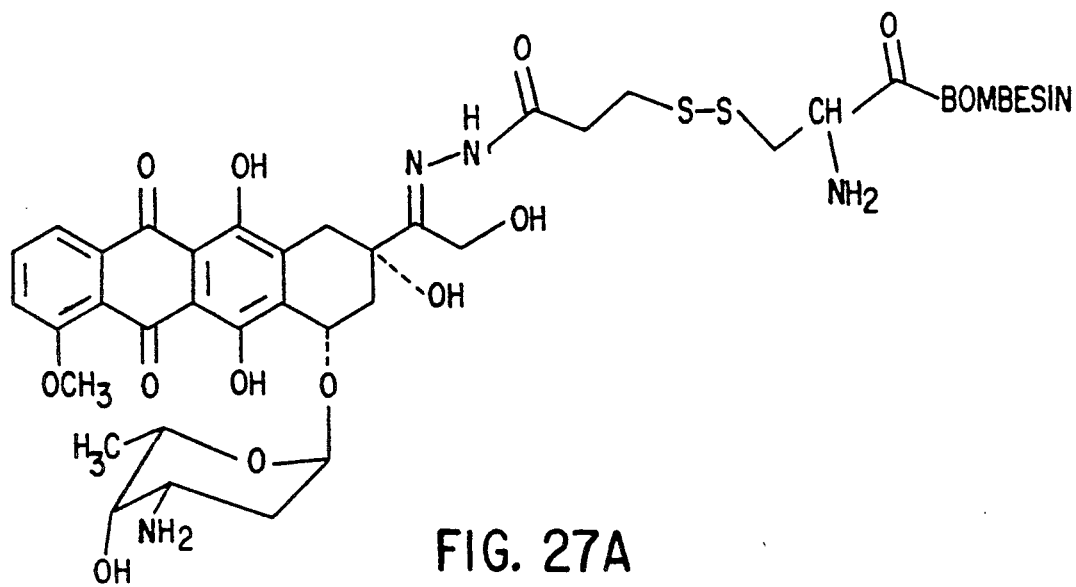
FIG. 27A depicts the chemical structure of a bombesin-ADM conjugate of the invention.
Figure 27B:
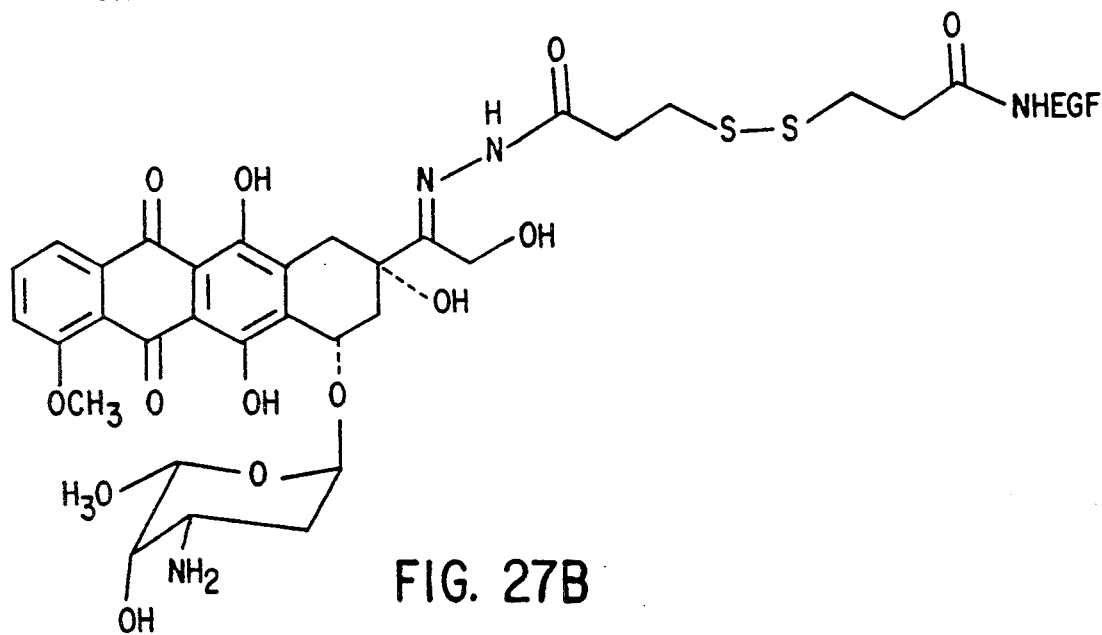
FIG. 27B depicts the chemical structure of an EGF-ADM conjugate of the invention.
Figure 27C:
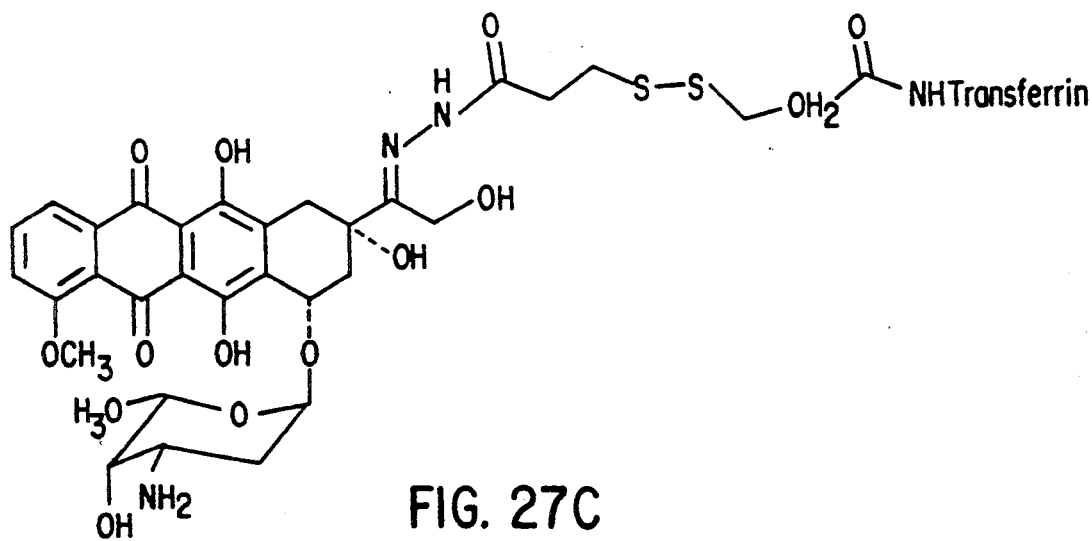
FIG. 27C depicts the chemical structure of a transferrin-ADM conjugate of the invention.
Figure 28A:
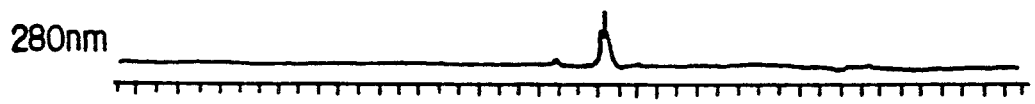
FIGS. 28A and 28B depict two HPLC chromatographs of cys-bombesin, chromatographed on a reverse phase C-18 column and an ion-exchange CX-300 column, respectively. Each chromatograph was run at 220 and 280 nm. These figures demonstrate the purity of the cys-bombesin preparation used to construct a bombesin-ADM conjugate of the invention.
Figure 28B:
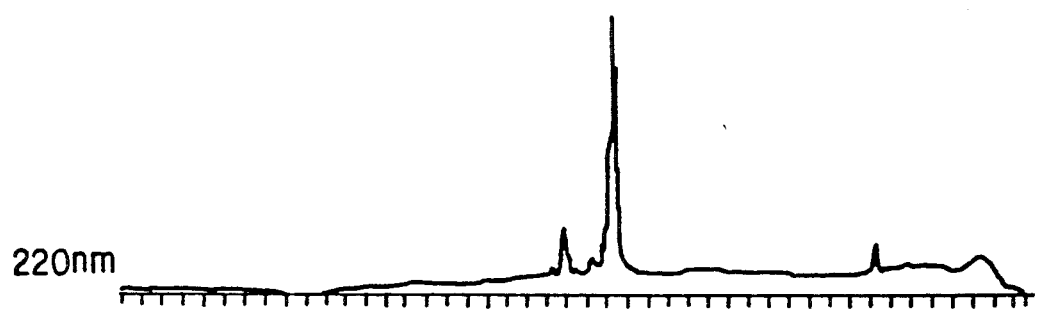
Figure 28C:
Figure 28D:

Yet another example of the conjugates of the present invention is the preparation of the anthracycline-ligand conjugate, wherein ADM is conjugated to the protein ligand, transferrin, again via a linker attached to the drug through a 13-keto acylhydrazone bond (see FIG. 27).

Preparation Of A Transferrin-ADM Conjugate 5.1 mg of human holo-transferrin, 100% iron-substituted (Sigma), was dissolved in 2 ml of a buffer containing 50 mM triethanolamine, 50 mM NaCl and 1 mM EDTA, pH 8.0. 40 µl of 2-IT (50 mM) was then added and the mixture incubated for 3 h at 37° C. The thiolated peptide was then separated on a PD-10 column (Pharmacia) as described earlier in Example 1. Next, 135 µl of ADM-HZN (2.1 mM) was added to 2.7 ml of thiolated transferrin in PBS buffer and the reaction mixture was incubated overnight at 4° C. The reaction mixture was then centrifuged at 2000 rpm for 10 min and the transferrin-ADM conjugate was separated from unreacted ADM by passage through a PD-10 column. The void volume containing the conjugate was collected and the molar ratio of ADM/transferrin was 4.6, using the $A_{280}$ of 1 for 1 mg/ml transferrin.

Examples 4–6 demonstrate therefore the preparation of anthracycline-ligand conjugates wherein a cytotoxic anthracycline drug is linked to a ligand reactive with receptors associated with a selected cell population sought to be killed. The anthracycline is linked to the ligand via a novel acid-sensitive acylhdrazone linkage. The conjugates described herein retain both the capacity of the ligand to bind to its receptors as well as the cytotoxicity of the anthracycline toward the cell population targeted via the ligand.

While we have hereinbefore presented a number of embodiments of this invention, it is apparent that our basic construction can be altered to provide other embodiments which utilize the immunoconjugates and methods of this invention. Therefore, it will be appreciated that the scope of this invention is to be defined by the claims appended hereto rather than by the specific embodiments which have been presented hereinbefore by way of example.

We claim:

1. An anthracycline-ligand conjugate comprising at least one anthracyline molecule linked to a ligand reactive with a selected cell population to be killed, the anthracycline having a keto group at the C-13 position and being attached to the ligand via a linker arm, the linker arm being covalently bound to the anthracycline by an acylhydrazone linkage at the 13-keto position of the anthracycline, and the linker arm additionally contains a disulfide or thioether bond.

2. The conjugate of claim 1 wherein the ligand is a protein, polypeptide or peptide molecule.

3. The conjugate of claim 2, wherein the ligand is selected from the group consisting of bombesin, EGF transferrin, gastrin, gastrin-releasing peptide, platelet-derived growth factor IL-2, IL-6, TGF-α, VGF, TGF-β, insulin and insulin-like growth factors I and II.

4. The conjugate of claim 1, wherein the ligand is a non-peptidyl ligand.

5. The conjugate of claim 4, wherein the ligand is selected from the group consisting of carbohydrates, steroids and lectins.

6. The conjugate of claim 1, wherein the anthracycline is selected from the group consisting of adriamycin, daunomycin, detorubicin, carminomycin, idarubicin, epirubicin, esorubicin, 4'-THP-adriamycin, AD-32 and 3'-deamino-3'-(3-cyano-4-morpholinyl)-doxorubicin.

7. The conjugate of claim 1, wherein the ligand is bombesin and the anthracycline is adriamycin.

8. The conjugate of claim 1, wherein the ligand is EGF and the anthracycline is adriamycin.

9. The conjugate of claim 1, wherein the ligand is transferrin and the anthracycline is adriamycin.

10. An adriamycin-bombesin conjugate comprising at least one adriamycin molecule linked to bombesin, the adriamycin being attached to the bombesin via a linker arm, the linker arm being covalently bound to the adriamycin by an acylhydrazone linkage at the 13-keto position of the adriamycin.

11. A pharmaceutically acceptable composition useful in the treatment of disease which comprises a pharmaceutically effective amount of at least one anthracycline-ligand conjugate according to claim 1 and a pharmaceutically acceptable carrier.

12. The composition of claim 11, wherein the disease to be treated is selected from the group consisting of cancers, non-malignant tumors, non-cytocidal viral or pathogenic infections, and autoimmune disorders.

* * * * *